United States Patent
Jiang et al.

(10) Patent No.: US 8,895,596 B2
(45) Date of Patent: Nov. 25, 2014

(54) CYCLIC BENZIMIDAZOLE DERIVATIVES USEFUL AS ANTI-DIABETIC AGENTS

(75) Inventors: Jinlong Jiang, Scotch Plains, NJ (US); Andrew J. Kassick, Scotch Plains, NJ (US); Ahmet Kekec, Jersey City, NJ (US); Iyassu K. Sebhat, Jersey City, NJ (US)

(73) Assignee: Merck Sharp & Dohme Corp, Rahway, NJ (US)

( * ) Notice: Subject to any disclaimer, the term of this patent is extended or adjusted under 35 U.S.C. 154(b) by 0 days.

(21) Appl. No.: 13/578,302

(22) PCT Filed: Feb. 21, 2011

(86) PCT No.: PCT/US2011/025585
§ 371 (c)(1),
(2), (4) Date: Aug. 10, 2012

(87) PCT Pub. No.: WO2011/106273
PCT Pub. Date: Sep. 1, 2011

(65) Prior Publication Data
US 2012/0309736 A1    Dec. 6, 2012

Related U.S. Application Data

(60) Provisional application No. 61/307,909, filed on Feb. 25, 2010.

(51) Int. Cl.
| | | |
|---|---|---|
| C07D 235/06 | (2006.01) |
| C07D 235/26 | (2006.01) |
| C07D 235/28 | (2006.01) |
| C07D 235/30 | (2006.01) |
| A61K 45/06 | (2006.01) |
| A61K 31/366 | (2006.01) |
| A61K 31/397 | (2006.01) |
| A61K 31/4184 | (2006.01) |
| A61K 31/4985 | (2006.01) |
| C07D 401/12 | (2006.01) |
| A61K 31/4412 | (2006.01) |
| C07D 403/12 | (2006.01) |
| C07D 405/12 | (2006.01) |

(52) U.S. Cl.
CPC ............ *C07D 405/12* (2013.01); *C07D 235/26* (2013.01); *A61K 45/06* (2013.01); *A61K 31/366* (2013.01); *A61K 31/397* (2013.01); *A61K 31/4184* (2013.01); *A61K 31/4985* (2013.01); *C07D 401/12* (2013.01); *A61K 31/4412* (2013.01); *C07D 403/12* (2013.01)
USPC ................... 514/387; 548/304.4; 548/307.1; 548/307.4

(58) Field of Classification Search
CPC .. C07D 235/06; C07D 235/26; C07D 235/28; C07D 235/30
USPC ................. 548/304.4, 307.1, 307.4; 514/387
See application file for complete search history.

(56) References Cited

U.S. PATENT DOCUMENTS

| | | |
|---|---|---|
| 5,596,025 A | 1/1997 | Oxman et al. |
| 6,312,662 B1 | 11/2001 | Erion et al. |
| 6,489,476 B1 | 12/2002 | Dang et al. |
| 7,098,220 B2 | 8/2006 | Rault et al. |
| 7,268,145 B2 | 9/2007 | Matsumoto et al. |
| 2005/0038068 A1 | 2/2005 | Iyengar et al. |
| 2005/0113283 A1 | 5/2005 | Solow-Cordero et al. |
| 2005/0148643 A1 | 7/2005 | Rui et al. |
| 2005/0187277 A1 | 8/2005 | Mjalti et al. |
| 2005/0255415 A1 | 11/2005 | Louwet et al. |
| 2005/0272765 A1 | 12/2005 | Feng et al. |
| 2006/0160872 A1 | 7/2006 | Norman et al. |
| 2006/0287356 A1 | 12/2006 | Iyengar et al. |
| 2007/0015665 A1 | 1/2007 | Potluri et al. |
| 2007/0032529 A1 | 2/2007 | Takagi et al. |
| 2008/0132501 A1 | 6/2008 | Sun et al. |

FOREIGN PATENT DOCUMENTS

| | | |
|---|---|---|
| DE | 3316095 A1 | 11/1983 |
| EP | 0120403 A2 | 10/1984 |
| EP | 0126030 A2 | 11/1984 |
| EP | 0128862 A2 | 12/1984 |
| EP | 0129506 A2 | 12/1984 |

(Continued)

OTHER PUBLICATIONS

Janssens, et al. Document No. 110:212855, retrieved from CAPLUS, Jun. 10, 1989.*
Janssens, et al. Document No. 108:21891, retrieved from CAPLUS, Jan. 23, 1988.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*

(Continued)

*Primary Examiner* — Shawquia Young
(74) *Attorney, Agent, or Firm* — Baerbel R. Brown; Catherine D. Fitch

(57) ABSTRACT

Novel compounds of the structural formula (I) are activators of AMP-protein kinase and are useful in the treatment, prevention and suppression of diseases mediated by the AMPK-activated protein kinase. The compounds of the present invention are useful in the treatment of Type 2 diabetes, hyperglycemia, metabolic syndrome, obesity, hypercholesterolemia, and hypertension.

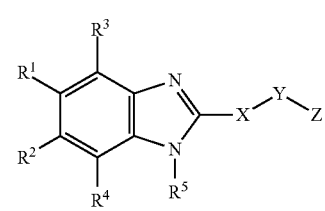

(I)

23 Claims, No Drawings

(56) References Cited

FOREIGN PATENT DOCUMENTS

| | | |
|---|---|---|
| EP | 0161219 A2 | 11/1985 |
| EP | 0161220 A2 | 11/1985 |
| EP | 0161222 A2 | 11/1985 |
| EP | 0560407 A1 | 9/1993 |
| EP | 0637585 A1 | 2/1995 |
| EP | 0655439 A2 | 5/1995 |
| GB | 2099167 A | 12/1982 |
| JP | 6298731 A | 10/1994 |
| JP | 9227854 A | 9/1997 |
| JP | 2002141067 A | 5/2002 |
| JP | 200467629 A | 3/2004 |
| JP | 200739406 A | 2/2007 |
| WO | 92/20642 A1 | 11/1992 |
| WO | 93/07124 A1 | 4/1993 |
| WO | 94/08982 A1 | 4/1994 |
| WO | 95/29897 A1 | 11/1995 |
| WO | 98/08818 A1 | 3/1998 |
| WO | 98/39342 A1 | 9/1998 |
| WO | 98/39343 A1 | 9/1998 |
| WO | 98/39344 A1 | 9/1998 |
| WO | 98/56761 A2 | 12/1998 |
| WO | 99/01454 A1 | 1/1999 |
| WO | 99/43672 A1 | 9/1999 |
| WO | 99/45016 A2 | 9/1999 |
| WO | 00/03997 A1 | 1/2000 |
| WO | 00/14095 A1 | 3/2000 |
| WO | 00/52015 A1 | 9/2000 |
| WO | 01/25238 A2 | 4/2001 |
| WO | 01/53272 A1 | 7/2001 |
| WO | 01/53291 A1 | 7/2001 |
| WO | 02/40019 A1 | 5/2002 |
| WO | 02/076454 A1 | 10/2002 |
| WO | 02/092575 A1 | 11/2002 |
| WO | 02/100833 A1 | 12/2002 |
| WO | 03/18061 A1 | 3/2003 |
| WO | 03/024937 A1 | 3/2003 |
| WO | 03/062392 A2 | 7/2003 |
| WO | 2004/035740 A2 | 4/2004 |
| WO | 2004/043913 A1 | 5/2004 |
| WO | 2004/071447 A2 | 8/2004 |
| WO | 2004/085425 A1 | 10/2004 |
| WO | 2005/002520 A2 | 1/2005 |
| WO | 2005/009389 A1 | 2/2005 |
| WO | 2005/009997 A1 | 2/2005 |
| WO | 2005/018672 A1 | 3/2005 |
| WO | 2005/020892 A2 | 3/2005 |
| WO | 2005/028624 A2 | 3/2005 |
| WO | 2005/042518 A2 | 5/2005 |
| WO | 2005/044793 A2 | 5/2005 |
| WO | 2005/047266 A1 | 5/2005 |
| WO | 2005/051298 A2 | 6/2005 |
| WO | 2005/051298 A3 | 6/2005 |
| WO | 2005/121132 A1 | 12/2005 |
| WO | 2006/018850 A2 | 2/2006 |
| WO | 2006/018850 A3 | 2/2006 |
| WO | 2006/030031 A1 | 3/2006 |
| WO | 2006/048159 A1 | 5/2006 |
| WO | 2006/060853 A1 | 6/2006 |
| WO | 2006/053342 A2 | 9/2006 |
| WO | 2006/094209 A2 | 9/2006 |
| WO | 2006/099379 A2 | 9/2006 |
| WO | 2006/116412 A2 | 11/2006 |
| WO | 2006/126171 A2 | 11/2006 |
| WO | 2006/126171 A3 | 11/2006 |
| WO | 2007/007463 A1 | 1/2007 |
| WO | 2007/007464 A1 | 1/2007 |
| WO | 2007/063993 A1 | 6/2007 |
| WO | 2007/084390 A2 | 7/2007 |
| WO | 2007/091106 A2 | 8/2007 |
| WO | 2007/095124 A2 | 8/2007 |
| WO | 2008/006432 A1 | 1/2008 |
| WO | 2008/008551 A2 | 1/2008 |
| WO | 2008/009348 A1 | 1/2008 |
| WO | 2008/062773 A1 | 5/2008 |
| WO | 2009/019504 A1 | 2/2009 |
| WO | 2009/100130 A1 | 8/2009 |
| WO | 2010/036613 A1 | 4/2010 |
| WO | 2010/047982 A1 | 4/2010 |
| WO | 2010/051176 A1 | 5/2010 |
| WO | 2010/051206 A1 | 5/2010 |
| WO | 2011/106273 A1 | 9/2011 |
| WO | 2012/116145 A1 | 8/2012 |

OTHER PUBLICATIONS

Lan, "An efficient method to access 2-substituted benzimiclazoles . . . ", Tetrahedron Letters, 2008, vol. 49, pp. 1910-1914.
Pangano, "Optimization of protein kinase CK2 inhibitors derived from . . . ", J. Med. Chem, 2004, vol. 47, pp. 6239-6247.
Bortolato, "In slico binding free energy predictability by using . . . ", J. Chem. Inf. Model, 2007, vol. 47, pp. 572-582.
Narayan, "Heterocyclic systems containing bridgehead nitrogen . . . ", Indian J. Chem., 1986, pp. 267-270.
Czarnocka-Janowicz, "Derivatives of 4(7)-methyl-and 5,6-dimethyl . . . ", Pol. J. Pharmacol. Pharm, 1977, vol. 29, pp. 69-73.
Bindal, "Heterocyclic systems containing bridgehead nitrogen . . . ", Indian J. of Chemistry, 1986, vol. 25B, pp. 807-811.
Tunnicliff, "The action of structural analogues of gamma-aminobutyric acid . . . ", Drug Develop. Res, 1984, vol. 4, pp. 51-59.
Lee, "Obesity: The role of hypothalamic AMP-activated protein . . . ", The Int'l J. of Biochem & Cell Biol, 2005, vol. 37, pp. 2254-2259.
Hardie, "AMP-activated protein kinase as a drug target", Annu. Rev. Pharmacol. Toxicol, 2007, vol. 47, pp. 185-210.
Musi, "AMP-activated protein kinase and type 2 diabetes", Current Med. Chem, 2006, vol. 13, pp. 583-589.
Kim, "Metformin inhibits hepatic gluconeogenesis . . . ", Diabetes, 2008, vol. 57. pp. 306-314.
Towler, AMP-activated protein kinase in metabolic control . . . Circulation Res., 2007, vol. 100, pp. 328-341.
Ofir, Increased glycogen stores due to gamma-AMPK overexpression . . . , Biochem. Pharmacol., 2008, vol. 75, pp. 1482-1491.
Hardie, "Role of Amp-activated protein kinase . . . ", FEBS Letters, 2008, vol. 582, pp. 81-89.
Labanauskas, "Synthesis and antiphlogistic activity of novel . . . ", Khimiko-Farmatsevticheskii Zhurnal, 1998, Vo. 32, pp. 15-16.
Viollet, "Targeting AMP-activated protein kinase as a novel . . . ", Diabets & Metabolism, 2007, vol. 33, pp. 395-402.
Winder, "AMP-activated protein kinase, a metabolic master . . . ", Am. J. Physiol, 1999, vol. 277, pp. E1-E10.
Rebstock, "The synthesis of several acid analogs . . . ", Ph.D. thesis, Michigan State University, 1956, pp. 5831-5832.
Rebstock, "Effect of chemical structure on the growth inhibition . . . ", Ph.D. theis, Michigan State University, 1956, pp. 19-22.
Bergeron, R. et al., "Effect of 5-Aminoimidazole-4-Carboxamide-1-B-n-Ribofuranoside Infusion on In Vivo Glucose and Lipid Metabolism in Lean and Obese Zucker Rats", Diabetes, 2001, pp. 1076-, vol. 50.
Blazquez, C, et al., "The AMP-Activated Protein Kinase Is Involved in the Regulation of Ketone Body Production by Astrocytes", Journal of Neurochemistry, 1999, pp. 1674-, vol. 73.
Buhl, E. S. et al., "Long-Term AICAR Administration Reduces metabolic Disturbances and Lowers Blood Pressure in Rats Displaying Features of the Insulin Resistance Syndrome", Diabetes, 2002, pp. 2199-, vol. 51.
Butler, A. E., et al., "B-Cell Deficit and Increased B-Cell Apoptosis in Hjmans With Type 2 Diabetes", Diabetes, 2003, pp. 102-, vol. 52.
Carling, D. et al., "A common Bicyclic protein kinase cascade inactivates the regulatory enzymes of fatty acid and cholesterol biosynthesis", FEB, 1987, pp. 217-222, vol. 223, No. 2.
Chen, Z-P, et al., "AMP-activated protein kinase phosphorylation of endothelial NO synthase", FEB Letters, 1999, pp. 285-289, vol. 443.
Halseth, A. E. et al., "Acute and chronic treatment of ob/ob and db/db mice with AICAR decreases blood glucose concentrations", Biochemical and biophysical Research Communications, 2002, pp. 798-805, vol. 294.
Hardie, D. G. et al., "AMP-activated protein kinase: the energy charge hypothesis revisited", BioEssays, 2001, pp. 1112-1119, vol. 23.

(56) References Cited

OTHER PUBLICATIONS

Kemp, B. E. et al., AMP-activated protein Kinase, super Metabolic regulator, Biochemical Society, 2003, pp. 162-.

LeClerc, I, et al., "Hepatocyte Nuclear Factor-4alpha Involved in Type 1 Maturity-Onset Diabetes of the Young Is a Novel Target of AMP-Activated Protein Kinase", Diabetes, 2001, pp. 1515-, vol. 50.

Lochhead, P. A. et al., "5-Aminoimidazole-4-Carboxamide Riboside Mimics of Effects of Insulin on the Expression of the 2 Key Gluconeogenic Genes PEPECK and Glucose-6-Phosphatase", Diabetes, 2000, pp. 896-, vol. 49.

Minokoshi, Y. et al., "Leptin stimulates fatty-acid oxidation by activating AMP-activated protein kinase", Nature, 2002, pp. 339-, vol. 415.

Mu, J. et al., "A Role for AMP-Activated Protein Kinase in Contraction- and Hypoxia-Regulated Glucose Transport in Skeletal Muscle", Molecular Cell, 2001, pp. 1085-1094, vol. 7.

Muoio, D. M. et al., "AMP-activated kinase reciprocally regulates triacylglycerol synthesis and fatty acid oxidation in liver and muscle: evidence that sn-glycerol-3-phosphate acyitransferase is a novel target", Biochem J., 1999, pp. 783-791, vol. 338.

Musi, N. et al., "Metformin Increases AMP-Activated Protein Kinase Activity in Skeletal Muscle of Subjects With Type 2 Diabetes", Diabetes, 2002, pp. 2074-, vol. 51.

Musi, N. et al., "Targeting the AMP-Activated Protein Kinase for the Treatment of Type 2 Diabetes", Current Drug Targets—Immune, Endocrine & Metabolic Disorders, 2002, pp. 119-127, vol. 2.

Petersen, K. F. et al., "Impaired Mitochondrial Activity in the Insulin-Resistant Offspring of Patients with Type 2 Diabetes", The New England Journal of Medicine, 2004, pp. 664-.

Polonsky, K. S., "Dynamics of insulin secretion in obesity and diabetes", International Journal of Obesity, 2000, pp. S29-S31, vol. 24, Suppl. 2.

Ruderman, N. B. et al., Minireview: Malonyl CoA, AMP-Activated Protein Kinase, and Adiposity, Endocrinology, 2003, pp. 5166-5171, vol. 144, No. 12.

Song, X. M. et al., 5-Aminoimidazole-4-carboxamide ribonucleoside treatment improves glucose homeostasis in insulin-resistant diabetic (ob/ob) mice, Diabetologia, 2002, pp. 56-65, vol. 45.

Winder, W. W. et al., AMP-activated protein kinase, a metabolic master switch: possible roles in Type 2 diabetes, The American Physiological Society, 1999, pp. E1-.

Zhou, G, et al., Role of AMP-activated protein kinase in mechanism of metformin action, The Journal of Clinical Investigation, 2001, pp. 1167-, vol. 108, No. 8.

Zhou, M. et al., "UCP-3 expression in skeletal muscle: effects of exercise, hypoxia, and AMP-activated protein kinase", Am J Physiol Endocrinol Metab, 2000, pp. E622-E629, vol. 279.

* cited by examiner

CYCLIC BENZIMIDAZOLE DERIVATIVES USEFUL AS ANTI-DIABETIC AGENTS

CROSS-REFERENCE TO RELATED APPLICATIONS

This application is a U.S. National Phase application under 35 U.S.C. §371 of PCT Application No. PCT/US2011/025585, filed 21 Feb. 2011, which claims priority from and the benefit of U.S. Provisional Application No. 61/307,909, filed 25 Feb. 2010.

BACKGROUND OF THE INVENTION

Diabetes is characterized by elevated levels of plasma glucose (hyperglycemia) in the fasting state or after administration of glucose during an oral glucose tolerance test. In type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients having Type 2 diabetes have a resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, *Int. J. Obes. Relat. Metab. Disard.* 24 *Suppl* 2:S29-31, 2000). Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the beta cells within the pancreatic islets initially compensate for insulin resistance by increasing insulin output. The onset of Type 2 diabetes due to insufficient increases (or actual declines) in beta cell mass is apparently due to increased beta cell apoptosis relative to non-diabetic insulin resistant individuals (Butler et al., *Diabetes* 52:102-110, 2003).

Persistent or uncontrolled hyperglycemia is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as Syndrome X or Metabolic Syndrome. Patients with Metabolic Syndrome have an increased risk of developing atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglitide); and (5) inhibitors of incretin hormone degradation (DPP-4 inhibitors, such as sitagliptin).

Many of the current treatments for diabetes have unwanted side effects. Phenformin and metformin can induce lactic acidosis, nausea/vomiting, and diarrhea. Metformin has a lower risk of side effects than phenformin and is widely prescribed for the treatment of Type 2 diabetes. The currently marketed PPAR gamma agonists are modestly effective in reducing plasma glucose and hemoglobinA1C, and do not greatly improve lipid metabolism or the lipid profile. Sulfonylureas and related insulin secretagogues can cause insulin secretion even if the glucose level is low, resulting in hypoglycemia, which can be fatal in severe cases. The administration of insulin secretagogues must therefore be carefully controlled. There remains a need for treatments for diabetes that work by novel mechanisms of action and that exhibit fewer side effects.

AMP-activated protein kinase (AMPK) has been identified as a regulator of carbohydrate and fatty acid metabolism that helps maintain energy balance in response to environmental and nutritional stress. There is evidence that activation of AMPK results in a number of beneficial effects on lipid and glucose metabolism by reducing glucogenesis and de novo lipogenesis (fatty acid and cholesterol synthesis), and by increasing fatty acid oxidation and skeletal muscle glucose uptake. Inhibition of ACC, by phosphorylation by AMPK, leads to a decrease in fatty acid synthesis and to an increase in fatty acid oxidation, while inhibition of HMG-CoA reductase, by phosphorylation by AMPK, leads to a decrease in cholesterol synthesis (Carling, D. et. al., FEBS Letters 223: 217 (1987)).

In the liver, AMPK activation results in a decrease in fatty acid and cholesterol synthesis, inhibiting hepatic glucose production and increasing fatty acid oxidation. It has been shown that AMP-activated protein kinase regulates triacylglycerol synthesis and fatty acid oxidation in liver and muscle via glycerol-3-phosphate acyltransferase (Muoio, D. M. et al., Biochem. J. 338:783 (1999)). Another substrate of AMPK, hepatocyte nuclear factor-4α, has been shown to be involved in type-1 maturity onset diabetes (Leclerc, I. et. al., Diabetes 50:1515 (2001)). Additional processes believed to be regulated through AMPK activation include the stimulation of glucose transport in skeletal muscle and the regulation of key genes in fatty acid and glucose metabolism in the liver (Hardie, D. G. and Hawley, S. A., Bioessays 23: 1112 (2001), Kemp, B. E. et. al., Biochem. Soc. Transactions 31:162 (2003), Musi, N. and Goodyear, L. J. Current Drug Targets-Immune, Endocrine and Metabolic Disorders 2:119 (2002); Lochhead, P. A. et. al., Diabetes 49:896 (2000); and Zhou, G. et. al., J. of Clin. Invest. 108: 1167 (2001).

In vivo studies have demonstrated the following beneficial effects of both acute and chronic administration of AICAR, an AMPK activator, in rodent models of obesity and type 2 diabetes: 1) an improvement in glucose homeostasis in insulin-resistant diabetic (ob/ob) mice; 2) a decrease in blood glucose concentrations in ob/ob and db/db mice and a blood glucose reduction of 35% following 8 weeks of administration; and 3) a reduction in metabolic disturbances and a reduction of blood pressure in rats displaying characteristics of insulin resistance syndrome (Bergeron, R. et. al., Diabetes 50:1076 (2001); Song, S. M. et. al., Diabetologia 45:56 (2002); Halseth, A. E. et. al., Biochem. and Biophys. Res. Comm. 294:798 (2002); and Buhl, E. S. et. al., Diabetes 51: 2199 (2002)). A further study of 7 week AICAR administration in obese Zucker (fa/fa) rats lead to a reduction in plasma triglycerides and free fatty acids; an increase in HDL cholesterol; and a normalization of glucose metabolism as assessed by an oral glucose tolerance test (Minokoshi, Y. et. al., Nature 415: 339 (2002)). Expression of dominant negative AMPK in skeletal muscle of transgenic mice has demonstrated that the AICAR effect on stimulation of glucose transport is dependent on AMPK activation (Mu, J. et. al., Molecular Cell 7: 1085 (2001)).

Recent data also suggest that AMPK activation is involved in the glucose and lipid-lowering effects of the anti-diabetic drug metformin. It has been shown that the diabetes drug metformin can activate AMPK in vivo at high concentrations (Zhou, G. et. al., J. of Clin. Invest. 108: 1167 (2001); Musi, N. et. al. Diabetes 51: 2074 (2002)).

Based on these studies, it is expected that the in vivo activation of AMPK in the liver may result in the reduction of hepatic glucose output, an improvement in overall glucose homeostasis, a decrease in fatty acid and cholesterol synthesis, and an increase in fatty acid oxidation. Stimulation of AMPK in skeletal muscle is expected to result in an increase in glucose uptake and fatty acid oxidation with resulting improvement of glucose homeostasis, and an improvement in insulin action. Finally, the resulting increase in energy expenditure should lead to a decrease in body weight. The lowering of blood pressure has also been reported to be a consequence of AMPK activation.

Increased fatty acid synthesis is a characteristic of many tumor cells, therefore decreasing the synthesis of fatty acids via AMPK activation may also be useful as a cancer therapy. Activation of AMPK may also be useful to treat ischemic events in the brain (Blazquez, C. et. al., J. Neurochem. 73: 1674 (1999)); to prevent damage from reactive oxygen species (Zhou, M. et. al., Am. J. Physiol. Endocrinol. Metab. 279: E622 (2000)); and to improve local circulatory systems (Chen, Z.-P., et. al. AMP-activated protein kinase phosphorylation of endothelial NO synthase. FEBS Letters 443: 285 (1999)).

Compounds that activate AMPK are expected to be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent AMPK activators that have pharmacokinetic and pharmacodynamic properties suitable for use as human pharmaceuticals.

Benzimidazole compounds are disclosed in WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. Nos. 6,312,662; 6,489,476; US 2005/0148643; DE 3 316 095; JP 6 298 731; EP 0 126 030; EP 0 128 862; EP 0 129 506; and EP 0 120 403. AMPK activators are disclosed in WO 08/006,432; WO 05/051298; WO 05/020892; US 2007/015665; US 2007/032529; US 2006/287356; and US 2005/038068.

SUMMARY OF THE INVENTION

The present invention is concerned with novel benzimidazole derivatives of structural Formula I:

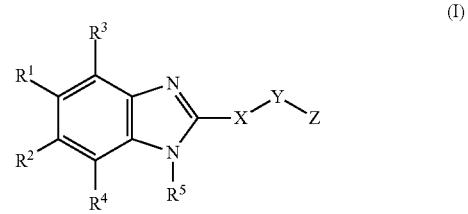

and pharmaceutically acceptable salts thereof. The compounds of structural formula I, and embodiments thereof, are activators of AMP-activated protein kinase (AMPK) and are useful in the treatment, prevention and suppression of diseases, disorders and conditions mediated by activation of AMP-activated protein kinase, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions responsive to activation of AMP-activated protein kinase in a subject in need thereof by administering the compounds and pharmaceutical compositions of the present invention. The present invention also relates to the use of compounds of the present invention for manufacture of a medicament useful in treating diseases, disorders and conditions responsive to the activation of AMP-activated protein kinase. The present invention is also concerned with treatment of these diseases, disorders and conditions by administering the compounds of the present invention in combination with a therapeutically effective amount of another agent known to be useful to treat the disease, disorder and condition. The invention is further concerned with processes for preparing the compounds of this invention.

DETAILED DESCRIPTION OF THE INVENTION

The present invention is concerned with novel compounds of structural Formula I:

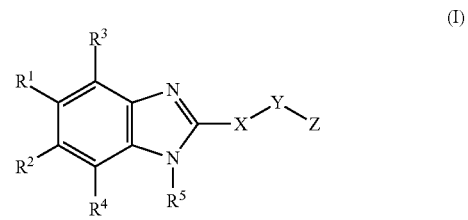

or a pharmaceutically acceptable salt thereof, wherein:
X is selected from:
(1) —O—,
(2) —O—CH$_2$—,
(3) —S—, (4) —S—CH$_2$—,
(5) —NR$^d$—,
(6) —NR$^d$—CH$_2$—,
(7) —CH$_2$—, and
(8) —CH$_2$—CH$_2$—,
wherein each CH$_2$ is unsubstituted or substituted with 1 or 2 substituents selected from: hydroxy, halogen, —C$_{1-6}$alkyl, —CO$_2$C$_{1-6}$alkyl, and —COC$_{1-6}$alkyl;
Y is selected from
  (1) —C$_{3-7}$cycloalkyl, and
  (2) —C$_{3-6}$cycloheteroalkyl,
wherein cycloalkyl and cycloheteroalkyl are unsubstituted or substituted with 1, 2, 3 or 4 substituents selected from R$^b$;
Z is selected from:
  (1) —(CH$_2$)$_n$CO$_2$H,
  (2) —(CH$_2$)$_n$CO$_2$R$^i$,
  (3) —(CH$_2$)$_n$NHCOR$^i$,
  (4) —(CH$_2$)$_n$SO$_2$NHC(O)R$^i$,
  (5) —(CH$_2$)$_n$NHSO$_2$R$^i$,
  (6) —(CH$_2$)$_n$C(O)NHSO$_2$R$^i$,
  (7) heteroaryl, and
  (8) —C$_{2-10}$cycloheteroalkyl,
wherein each CH$_2$ is unsubstituted or substituted with 1 or 2 substituents selected from C$_{1-6}$alkyl, and —OH, and wherein each cycloheteroalkyl and heteroaryl is unsubstituted or substituted with 1, 2, 3 or 4 substituents selected from R$^c$;
each R$^1$ and R$^2$ is independently selected from:
  (1) halogen,
  (2) —(CH$_2$)$_p$aryl,
  (3) biphenyl, and
  (4) —(CH$_2$)$_p$heteroaryl,
wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each biphenyl, aryl and heteroaryl is unsubstituted or substituted with 1, 2, 3 or 4 substituents independently selected from R$^a$, provided that one and only one of R$^1$ and R$^2$ is halogen;
R$^3$ and R$^4$ are each independently selected from:
  (1) hydrogen,
  (2) halogen,
  (3) —C$_{1-6}$alkyl,
  (4) —C$_{2-6}$alkenyl,
  (5) —C$_{2-6}$alkynyl,
  (6) —CN,
  (7) —CF$_3$,
  (8) —OC$_{1-6}$alkyl,
  (9) —SO$_2$C$_{1-6}$alkyl,
  (10) —SO$_2$NHC$_{1-6}$alkyl, and
  (11) —C(O)NHC$_{1-6}$alkyl,
wherein each alkyl is unsubstituted or substituted with 1, 2 or 3 halogens;
R$^5$ is selected from:
  (1) hydrogen,
  (2) —C$_{1-6}$alkyl,
  (3) —CH$_2$CO$_2$H, and
  (4) —CH$_2$CO$_2$C$_{1-6}$alkyl;
each R$^a$ is independently selected from the group consisting of:
  (1) hydrogen,
  (2) halogen,
  (3) —(CH$_2$)$_m$OH,
  (4) —(CH$_2$)$_m$N(R$^j$)$_2$,
  (5) —(CH$_2$)$_m$CN,
  (6) —C$_{1-6}$alkyl,
  (7) —(CH$_2$)$_m$CF$_3$,
  (8) —(CH$_2$)$_m$OCF$_3$,
  (9) —(CH$_2$)$_m$SC$_{1-6}$alkyl,
  (10) —(CH$_2$)$_m$S(O)$_2$C$_{1-6}$alkyl,
  (11) —(CH$_2$)$_m$S(O)$_2$N(C$_{1-6}$alkyl)$_2$,
  (12) —(CH$_2$)$_m$C(O)N(R$^j$)$_2$,
  (13) —(CH$_2$)$_m$N(R$^j$)C(O)R$^f$,
  (14) —(CH$_2$)$_m$C(O)R$^f$,
  (15) —(CH$_2$)$_m$CO$_2$R$^f$,
  (16) —(CH$_2$)$_m$OC(O)R$^f$,
  (17) —(CH$_2$)$_m$C$_{3-7}$cycloalkyl,
  (18) —(CH$_2$)$_m$C$_{3-7}$cycloalkenyl,
  (19) —(CH$_2$)$_m$C$_{2-6}$cycloheteroalkyl,
  (20) —(CH$_2$)$_m$C$_{2-6}$cycloheteroalkenyl,
  (21) —(CH$_2$)$_m$aryl, and
  (22) —(CH$_2$)$_m$heteroaryl,
wherein each CH$_2$ is unsubstituted or substituted with 1 or 2 substituents selected from: oxo, —(CH$_2$)$_{0-3}$OH, —CN, —C$_{1-6}$ alkyl, —OC$_{1-6}$alkyl, halogen, —CH$_2$F, —CHF$_2$, —CF$_3$, and —CO$_2$C$_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, (CH$_2$)$_{0-3}$OH, —CN, —C$_{1-6}$alkyl, —OC$_{1-6}$alkyl, halogen, —CH$_2$F, —CHF$_2$, —CF$_3$, and —CO$_2$C$_{1-6}$alkyl;
each R$^b$ is independently selected from:
  (1) hydrogen,
  (2) —C$_{1-6}$alkyl,
  (3) aryl,
  (4) heteroaryl,
  (5) —C$_{3-6}$cycloalkyl,
  (6) —C$_{3-6}$cycloalkenyl,
  (7) —C$_{3-6}$cycloheteroalkyl,
  (8) halogen,
  (9) —OH,
  (10) —OC$_{1-6}$alkyl,
  (11) —CF$_3$,
  (12) —CN, and
  (13) —SO$_2$C$_{1-6}$alkyl,
wherein each alkyl, aryl, heteroaryl, cycloalkyl, cycloalkenyl and cycloheteroalkyl is unsubstituted or substituted with 1, 2 or 3 halogens;
each R$^c$ is independently selected from:
  (1) hydrogen,
  (2) halogen,
  (3) oxo,
  (4) —(CH$_2$)$_r$OH,
  (5) —(CH$_2$)$_r$N(R$^e$)$_2$,
  (6) —(CH$_2$)$_r$CN,
  (7) —C$_{1-6}$alkyl,
  (8) —CF$_3$,
  (9) —(CH$_2$)$_r$C$_{3-7}$cycloalkyl, and
  (10) —(CH$_2$)$_r$C$_{2-6}$cycloheteroalkyl,
wherein each CH$_2$ is unsubstituted or substituted with 1 or 2 substituents selected from: oxo, OH, —CN, —C$_{1-6}$allyl, —OC$_{1-6}$alkyl, halogen, —CH$_2$F, —CHF$_2$, and —CF$_3$, and wherein alkyl, cycloalkyl, and cycloheteroalkyl are unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$;
each R$^d$ is independently selected from:
  (1) hydrogen, and
  (2) C$_{1-6}$alkyl;
each R$^e$ is independently selected from:
  (1) hydrogen, and
  (2) C$_{1-6}$alkyl,
wherein alkyl is unsubstituted or substituted with 1, 2, 3 or 4 substituents selected from: —OH, oxo, halogen, C$_{1-6}$alkyl, and —OC$_{1-6}$alkyl;

each $R^f$ is independently selected from:
(1) $C_{1-6}$alkyl,
(2) $C_{4-7}$cycloalkyl,
(3) $C_{4-7}$cycloalkenyl,
(4) $C_{3-7}$cycloheteroalkyl,
(5) $C_{3-7}$cycloheteroalkenyl,
(6) aryl, and
(7) heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$C_{1-6}$alkyl, —$OC_{1-6}$alkyl, halogen, —$CH_2F$, —$CHF_2$, and —$CF_3$;
each $R^i$ is independently selected from:
(1) hydrogen,
(2) $C_{1-6}$alkyl,
(3) $C_{4-7}$cycloalkyl,
(4) $C_{4-7}$cycloalkenyl,
(5) $C_{3-7}$cycloheteroalkyl,
(6) $C_{3-7}$cycloheteroalkenyl,
(7) aryl, and
(8) heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$OCOC_{1-6}$alkyl, and —$OCO_2C_{1-6}$alkyl;
each $R^j$ is independently selected from:
(1) hydrogen,
(2) —$C_{1-6}$alkyl,
(3) —$C_{3-6}$cycloalkyl, and
(4) —$C_{3-6}$cycloheteroalkyl,
wherein alkyl, cycloalkyl and cycloheteroalkyl are unsubstituted or substituted with 1, 2, 3 or 4 substituents selected from: —OH, oxo, halogen, $C_{1-6}$alkyl, —$OC_{1-6}$alkyl, —$NH_2$, —$NH(C_{1-6}$alkyl), and —$N(C_{1-6}$alkyl$)_2$;
n is 0, 1, 2, 3 or 4;
m is 0, 1, 2, 3 or 4;
p is 0, 1, 2, or 3; and
r is 0, 1 or 2.

In one embodiment of the present invention, X is selected from: —O—, —O—$CH_2$—, —S—, —S—$CH_2$—, —$NR^d$—, —$NR^d$—$CH_2$—, —$CH_2$—, and —$CH_2$—$CH_2$—, wherein each $CH_2$ is unsubstituted or substituted with 1 or 2 substituents selected from: hydroxy, halogen, —$C_{1-6}$alkyl, —$CO_2C_{1-6}$alkyl, and —$COC_{1-6}$alkyl. In a class of this embodiment, X is selected from: —O—, and —O—$CH_2$—, wherein each $CH_2$ is unsubstituted or substituted with 1 or 2 substituents selected from: hydroxy, halogen, —$C_{1-6}$alkyl, —$CO_2C_{1-6}$alkyl, and —$COC_{1-6}$alkyl. In another class of this embodiment of the present invention, X is selected from: —O—, and —O—$CH_2$—, wherein each $CH_2$ is unsubstituted or substituted with 1 substituent selected from: hydroxy, halogen, —$C_{1-6}$alkyl, $CO_2C_{1-6}$alkyl, and —$COC_{1-6}$alkyl. In another class of the present invention, X is selected from: —O—, and —O—$CH_2$—, wherein each $CH_2$ is unsubstituted or substituted with 1 or 2 substituents selected from: halogen, and $C_{1-6}$alkyl. In a class of this embodiment of the present invention, X is selected from: —O—, and —O—$CH_2$—, wherein each $CH_2$ is unsubstituted or substituted with 1 or 2 substituents selected from: $C_{1-6}$alkyl. In another class of this embodiment, X is selected from: —O—, and —O—$CH_2$—.

In another embodiment of the present invention, X is —O—.

In another embodiment of the present invention, X is —O—$CH_2$—, wherein $CH_2$ is unsubstituted or substituted with 1 or 2 substituents selected from: hydroxy, halogen, —$C_{1-6}$alkyl, —$CO_2C_{1-6}$alkyl, and —$COC_{1-6}$alkyl. In another embodiment of the present invention, X is —O—$CH_2$—.

In another embodiment of the present invention, Y is selected from: —$C_{3-7}$cycloalkyl, and —$C_{3-6}$cycloheteroalkyl, wherein each cycloalkyl and cycloheteroalkyl is unsubstituted or substituted with 1, 2, 3 or 4 substituents selected from $R^b$.

In another embodiment of the present invention, Y is selected from the group consisting of: cyclopropyl, cyclobutyl, cyclopentyl, cyclohexyl, tetrahydropyran, tetrahydrofuran, piperidine and pyrrolidine, wherein each cyclopropyl, cyclobutyl, cyclopentyl, cyclohexyl, tetrahydropyran, tetrahydrofuran, piperidine and pyrrolidine is unsubstituted or substituted with 1, 2 or 3 substituents selected from $R^b$. In a class of this embodiment, Y is selected from the group consisting of: cyclopropyl, cyclobutyl, cyclopentyl, cyclohexyl, tetrahydropyran, tetrahydrofuran, pyrrolidine and piperidine. In another class of this embodiment, Y is selected from the group consisting of cyclopropyl, cyclobutyl, cyclopentyl, cyclohexyl, tetrahydropyran, tetrahydrofuran, N-methylpyrrolidine and N-methyl piperidine. In another class of this embodiment, Y is selected from the group consisting of: cyclopropyl, cyclobutyl, cyclopentyl, cyclohexyl, tetrahydropyran, tetrahydrofuran and piperidine, wherein each cyclopropyl, cyclobutyl, cyclopentyl, cyclohexyl, tetrahydropyran, tetrahydrofuran and piperidine is unsubstituted or substituted with 1, 2 or 3 substituents selected from $R^b$. In another class of this embodiment, Y is selected from the group consisting of: cyclopropyl, cyclobutyl, cyclopentyl, and cyclohexyl, tetrahydropyran, tetrahydrofuran and piperidine. In another class of this embodiment, Y is selected from the group consisting of: cyclopropyl, cyclobutyl, cyclopentyl, and cyclohexyl, tetrahydropyran, tetrahydrofuran and N-methyl piperidine.

In another embodiment of the present invention, Y is —$C_{3-6}$ cycloheteroalkyl, wherein cycloheteroalkyl is unsubstituted or substituted with 1, 2, 3 or 4 substituents selected from $R^b$. In a class of this embodiment, Y is selected from the group consisting of: tetrahydropyran, tetrahydrofuran, piperidine and pyrrolidine, wherein each tetrahydropyran, tetrahydrofuran, piperidine and pyrrolidine is unsubstituted or substituted with 1, 2 or 3 substituents selected from $R^b$. In another class of this embodiment, Y is selected from the group consisting of: tetrahydropyran, tetrahydrofuran, pyrrolidine and piperidine. In another class of this embodiment, Y is selected from the group consisting of: tetrahydropyran, tetrahydrofuran, N-methylpyrrolidine and N-methyl piperidine. In another class of this embodiment, Y is selected from the group consisting of tetrahydropyran, tetrahydrofuran, and piperidine, wherein each tetrahydropyran, tetrahydrofuran and piperidine is unsubstituted or substituted with 1, 2 or 3 substituents selected from $R^b$. In another class of this embodiment, Y is selected from the group consisting of tetrahydropyran, tetrahydrofuran and piperidine. In another class of this embodiment, Y is selected from the group consisting of: tetrahydropyran, tetrahydrofuran and N-methyl piperidine.

In another embodiment of the present invention, Y is —$C_{3-7}$ cycloalkyl, wherein cycloalkyl is unsubstituted or substituted with 1, 2, 3 or 4 substituents selected from $R^b$.

In another embodiment of the present invention, Y is selected from the group consisting of: cyclopropyl, cyclobutyl, cyclopentyl, and cyclohexyl, wherein each cyclopropyl, cyclobutyl, cyclopentyl, and cyclohexyl is unsubstituted or substituted with 1, 2 or 3 substituents selected from $R^b$. In a class of this embodiment, Y is selected from the group consisting of: cyclopropyl, cyclobutyl, cyclopentyl, and cyclohexyl.

In another embodiment of the present invention, Y is selected from the group consisting of: cyclohexyl, and cyclobutyl, wherein each cyclohexyl and cyclobutyl is unsubstituted or substituted with 1, 2 or 3 substituents selected from $R^b$. In a class of this embodiment, Y is selected from the group consisting of cyclohexyl, and cyclobutyl.

In another embodiment of the present invention, Y is cyclohexyl, wherein cyclohexyl is unsubstituted or substituted with 1, 2 or 3 substituents selected from $R^b$. In a class of this embodiment, Y is cyclohexyl.

In another embodiment of the present invention, Y is cyclobutyl, wherein cyclobutyl is unsubstituted or substituted with 1, 2 or 3 substituents selected from $R^b$. In a class of this embodiment, Y is cyclobutyl.

In another embodiment of the present invention, Z is selected from: —$(CH_2)_nCO_2H$, —$(CH_2)_nCO_2R^i$, —$(CH_2)_nNHCOR^i$, —$(CH_2)_nSO_2NHC(O)R^i$, —$(CH_2)_nNHSO_2R^i$, —$(CH_2)_nC(O)NHSO_2R^i$, heteroaryl, and —$C_{2-10}$cycloheteroalkyl, wherein each $CH_2$ is unsubstituted or substituted with 1 or 2 substituents selected from $C_{1-6}$alkyl, and —OH, and wherein each cycloheteroalkyl and heteroaryl is unsubstituted or substituted with 1, 2, 3 or 4 substituents selected from $R^c$. In a class of this embodiment, Z is selected from: —$(CH_2)_nCO_2H$, —$(CH_2)_nNHCOR^i$, —$(CH_2)_nNHSO_2R^i$, —$(CH_2)_nC(O)NHSO_2R^i$, heteroaryl, and —$C_{2-10}$cycloheteroalkyl, wherein each $CH_2$ is unsubstituted or substituted with 1 or 2 substituents selected from $C_{1-6}$alkyl, and —OH, and wherein each cycloheteroalkyl and heteroaryl is unsubstituted or substituted with 1, 2, 3 or 4 substituents selected from $R^c$.

In another class of this embodiment, Z is selected from: —$CO_2H$, $NHCOR^i$, —$NHSO_2R^i$, —$C(O)NHSO_2R^i$, heteroaryl, and —$C_{2-10}$cycloheteroalkyl, wherein each cycloheteroalkyl and heteroaryl is unsubstituted or substituted with 1, 2, 3 or 4 substituents selected from $R^c$.

In another class of this embodiment, Z is selected from the group consisting of: —$CO_2H$, —$NHCOCH_3$, —$NHSO_2CH_3$, —$C(O)NHSO_2CH_2CH_3$, tetrazole, imidazole, triazolidine, oxadiazole, diazaspiro[3.5]nonane, triazole and thiadiazole, wherein each alkyl, cycloheteroalkyl and heteroaryl is unsubstituted or substituted with 1, 2, 3 or 4 substituents selected from $R^c$. In a subclass of this class, Z is selected from the group consisting of: —$CO_2H$, —$NHCOCH_3$, —$NHSO_2CH_3$, —$C(O)NHSO_2CH_2CH_3$, 2H-tetrazole, 5,5-dimethyl-1,5-dihydro-4H-imidazol-4-one, 1,2,4-triazolidine-3,5-dione, 1,2,4-oxadiazol-5(4H)-one, 2,4-dihydro-3H-1,2,4-triazol-3-one, 6,8-diazaspiro[3.5]nonane-5,7,9-trione, 2,4-dihydro-3H-1,2,4-triazol-3-one, and 1,2,4-thiadiazol-5(4H)-one, wherein each alkyl, cycloheteroalkyl and heteroaryl is unsubstituted or substituted with 1, 2, 3 or 4 substituents selected from $R^c$.

In another class of this embodiment, In a class of this embodiment, Z is selected from the group consisting of: —$CO_2H$, —$NHCOCH_3$, —$NHSO_2CH_3$, —$C(O)NHSO_2CH_2CH_3$, tetrazole, imidazole, triazolidine, oxadiazole, diazaspiro[3.5]nonane, triazole, thiadiazole, oxazolidine, and thiazolidine, wherein each alkyl, cycloheteroalkyl and heteroaryl is unsubstituted or substituted with 1, 2, 3 or 4 substituents selected from $R^c$. In another class of this embodiment, In a class of this embodiment, Z is selected from the group consisting of: —$CO_2H$, —$NHCOCH_3$, —$NHSO_2CH_3$, —$C(O)NHSO_2CH_2CH_3$, 2H-tetrazole, 5,5-dimethyl-1,5-dihydro-4H-imidazol-4-one, 1,2,4-triazolidine-3,5-dione, 1,2,4-oxadiazol-5(4H)-one, 2,4-dihydro-3H-1,2,4-triazol-3-one, 6,8-diazaspiro[3.5]nonane-5,7,9-trione, 2,4-dihydro-3H-1,2,4-triazol-3-one, 1,2,4-thiadiazol-5(4H)-one, 5-methyl-2,4-dihydro-3H-1,2,4-triazol-3-one, 1,3-oxazolidine-2,4-dione, 1,3,4-oxadiazol-2(3H)-one, 1,3-thiazolidine-2,4-dione, 1,3,4-thiadiazol-2(3H)-one, 2,4-dihydro-3H-1,2,4-triazol-3-one, 1,3,4-oxadiazole, 1,3,4-thiadiazole, and 4H-1,2,4-triazole, wherein each alkyl, cycloheteroalkyl and heteroaryl is unsubstituted or substituted with 1, 2, 3 or 4 substituents selected from $R^c$.

In another embodiment of the present invention, Z is selected from: —$(CH_2)_nCO_2H$, —heteroaryl, and —$C_{2-10}$cycloheteroalkyl, wherein each $CH_2$ is unsubstituted or substituted with 1 or 2 substituents selected from $C_{1-6}$alkyl, —OH and —$NH_2$, and wherein each cycloheteroalkyl and heteroaryl is unsubstituted or substituted with 1, 2, 3 or 4 substituents selected from $R^c$. In a class of this embodiment, Z is selected from: —$(CH_2)_nCO_2H$, tetrazole, imidazole, triazolidine, oxadiazole, diazaspiro[3.5]nonane, triazole and thiadiazole, wherein each alkyl, cycloheteroalkyl and heteroaryl is unsubstituted or substituted with 1, 2, 3 or 4 substituents selected from $R^c$. In a subclass of this class, Z is selected from the group consisting of: —$CO_2H$, 2H-tetrazole, 5,5-dimethyl-1,5-dihydro-4H-imidazol-4-one, 1,2,4-triazolidine-3,5-dione, 1,2,4-oxadiazol-5(4H)-one, 2,4-dihydro-3H-1,2,4-triazol-3-one, 6,8-diazaspiro[3.5]nonane-5,7,9-trione, 2,4-dihydro-3H-1,2,4-triazol-3-one, and 1,2,4-thiadiazol-5(4H)-one, wherein each alkyl, cycloheteroalkyl and heteroaryl is unsubstituted or substituted with 1, 2, 3 or 4 substituents selected from $R^c$.

In another embodiment of the present invention, Z is selected from: —$CO_2H$, -heteroaryl, and —$C_{2-10}$cycloheteroalkyl, wherein each cycloheteroalkyl and heteroaryl is unsubstituted or substituted with 1, 2 or 3 substituents selected from $R^c$. In another class of this embodiment, Z is selected from: —$CO_2H$, tetrazole, imidazole, triazolidine, oxadiazole, diazaspiro[3.5]nonane, triazole and thiadiazole, wherein each alkyl, cycloheteroalkyl and heteroaryl is unsubstituted or substituted with 1, 2, 3 or 4 substituents selected from $R^c$.

In another embodiment of the present invention, Z is selected from: -heteroaryl, and —$C_{2-10}$cycloheteroalkyl, wherein each cycloheteroalkyl and heteroaryl is unsubstituted or substituted with 1, 2, 3 or 4 substituents selected from $R^c$. In a class of this embodiment, Z is selected from: tetrazole, imidazole, triazolidine, oxadiazole, diazaspiro[3.5]nonane, triazole and thiadiazole, wherein each alkyl, cycloheteroalkyl and heteroaryl is unsubstituted or substituted with 1, 2, 3 or 4 substituents selected from $R^c$. In a subclass of this class, Z is selected from the group consisting of: 2H-tetrazole, 5,5-dimethyl-1,5-dihydro-4H-imidazol-4-one, 1,2,4-triazolidine-3,5-dione, 1,2,4-oxadiazol-5(4H)-one, 2,4-dihydro-3H-1,2,4-triazol-3-one, 6,8-diazaspiro[3.5]nonane-5,7,9-trione, 2,4-dihydro-3H-1,2,4-triazol-3-one, and 1,2,4-thiadiazol-5(4H)-one, wherein each alkyl, cycloheteroalkyl and heteroaryl is unsubstituted or substituted with 1, 2, 3 or 4 substituents selected from $R^c$.

In another embodiment of the present invention, Z is selected from: —$CO_2H$, and -heteroaryl, wherein each heteroaryl is unsubstituted or substituted with 1, 2 or 3 substituents selected from $R^c$. In a class of this embodiment, Z is selected from: —$CO_2H$, tetrazole, imidazole, oxadiazole, triazole and thiadiazole, wherein each heteroaryl is unsubstituted or substituted with 1, 2, 3 or 4 substituents selected from $R^c$. In another class of this embodiment, Z is selected from: —$CO_2H$, and tetrazole, wherein each tetrazole is unsubstituted or substituted with 1, 2, 3 or 4 substituents selected from $R^c$.

In another embodiment of the present invention, Z is selected from: —$(CH_2)_n CO_2H$, wherein each $CH_2$ is unsubstituted or substituted with 1 or 2 substituents selected from $C_{1-6}$alkyl, —OH and —$NH_2$. In a class of this embodiment, Z is selected from: —$(CH_2)_{1-3}CO_2H$. In another class of this embodiment, Z is selected from: —$(CH_2)_{1-2}CO_2H$. In another class of this embodiment, Z is selected from: —$(CH_2)CO_2H$. In another class of this embodiment, Z is —$CO_2H$.

In another embodiment of the present invention, each $R^1$ and $R^2$ is independently selected from: halogen, —$(CH_2)_p$aryl, biphenyl, and —$(CH_2)_p$heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, and wherein each biphenyl, aryl and heteroaryl is unsubstituted or substituted with 1, 2, 3 or 4 substituents independently selected from $R^a$, provided that one and only one of $R^1$ and $R^2$ is halogen.

In another embodiment of the present invention, each $R^1$ and $R^2$ is independently selected from: halogen, aryl, biphenyl, and heteroaryl, wherein each biphenyl, aryl and heteroaryl is unsubstituted or substituted with 1, 2, 3 or 4 substituents independently selected from $R^a$, provided that one and only one of $R^1$ and $R^2$ is halogen.

In another class of this embodiment, each $R^1$ and $R^2$ is independently selected from: Br, F, Cl, phenyl, naphthalene, biphenyl, indole, and N-methyl benzomorpholine, wherein each phenyl, naphthalene, biphenyl, indole, and N-methyl benzomorpholine is unsubstituted or substituted with 1, 2, 3 or 4 substituents independently selected from $R^a$, provided that one and only one of $R^1$ and $R^2$ is selected from the group consisting of: Br, F and Cl. In another class of this embodiment, each $R^1$ and $R^2$ is independently selected from: F, Cl, biphenyl, indole, and N-methyl benzomorpholine, wherein each biphenyl, indole, and N-methyl benzomorpholine is unsubstituted or substituted with 1, 2, 3 or 4 substituents independently selected from $R^a$, provided that one and only one of $R^1$ and $R^2$ is selected from the group consisting of: F and Cl.

In another embodiment of the present invention, each $R^1$ and $R^2$ is independently selected from: F, Cl, biphenyl, indole, and N-methyl benzomorpholine, wherein each biphenyl, indole, and N-methyl benzomorpholine is unsubstituted or substituted with 1, 2, 3 or 4 substituents independently selected from $R^a$, provided that one and only one of $R^1$ and $R^2$ is selected from the group consisting of: F and Cl. In another class of this embodiment, each $R^1$ and $R^2$ is independently selected from: F, Cl, biphenyl, and indole, wherein each biphenyl and indole is unsubstituted or substituted with 1, 2 or 3 substituents independently selected from $R^a$, provided that at least one of and only one of $R^1$ and $R^2$ is selected from the group consisting of: F and Cl. In another class of this embodiment, each $R^1$ and $R^2$ is independently selected from: F, and biphenyl, wherein each biphenyl is unsubstituted or substituted with 1, 2 or 3 substituents independently selected from $R^a$, provided that at least one of and only one of $R^1$ and $R^2$ is F.

In another embodiment of the present invention, $R^1$ is independently selected from: —$(CH_2)_p$aryl, biphenyl, and —$(CH_2)_p$heteroaryl, wherein each $CH_2$ is unsubstituted or substituted with 1 or 2 substituents selected from: halogen, $CF_3$, —OH, —$NH_2$, —$C_{1-6}$alkyl, $NHC_{1-6}$alkyl, and —$N(C_{1-6} alkyl)_2$, and wherein each biphenyl, aryl and heteroaryl is unsubstituted or substituted with 1, 2, 3 or 4 substituents independently selected from $R^a$.

In another embodiment of the present invention, $R^1$ is independently selected from: aryl, biphenyl, and heteroaryl, wherein each biphenyl, aryl and heteroaryl is unsubstituted or substituted with 1, 2, 3 or 4 substituents independently selected from $R^a$. In a class of this embodiment, $R^1$ is independently selected from: phenyl naphthalene, biphenyl, indole, and N-methyl benzomorpholine, wherein each phenyl, naphthalene, biphenyl, indole and N-methyl benzomorpholine is unsubstituted or substituted with 1, 2, 3 or 4 substituents independently selected from $R^a$.

In another embodiment of the present invention, $R^1$ is independently selected from: phenyl, biphenyl, and heteroaryl, wherein each biphenyl and heteroaryl is unsubstituted or substituted with 1, 2, 3 or 4 substituents independently selected from $R^a$; or a pharmaceutically acceptable salt thereof. In a class of this embodiment, $R^1$ is independently selected from: phenyl, biphenyl, indole, and N-methyl benzomorpholine, wherein each phenyl, biphenyl, indole and N-methyl benzomorpholine is unsubstituted or substituted with 1, 2, 3 or 4 substituents independently selected from $R^a$. In another class of this embodiment, $R^1$ is independently selected from: phenyl, biphenyl, and indole, wherein each phenyl, biphenyl and indole is unsubstituted or substituted with 1, 2 or 3 substituents independently selected from $R^a$. In another class of this embodiment, $R^1$ is independently selected from: phenyl, biphenyl, and indole, wherein each phenyl, biphenyl and indole is unsubstituted or substituted with 1 or 2 substituents independently selected from $R^a$. In another class of this embodiment, $R^1$ is independently selected from: phenyl, biphenyl, and indole, wherein each phenyl, biphenyl and indole is unsubstituted or substituted with one substituent independently selected from $R^a$.

In another embodiment of the present invention, $R^1$ is independently selected from: biphenyl, and heteroaryl, wherein each biphenyl and heteroaryl is unsubstituted or substituted with 1, 2, 3 or 4 substituents independently selected from $R^a$. In a class of this embodiment, $R^1$ is independently selected from: biphenyl, indole, and N-methyl benzomorpholine, wherein each biphenyl, indole and N-methyl benzomorpholine is unsubstituted or substituted with 1, 2, 3 or 4 substituents independently selected from $R^a$. In another class of this embodiment, $R^1$ is independently selected from: biphenyl, and indole, wherein each biphenyl and indole is unsubstituted or substituted with 1, 2 or 3 substituents independently selected from $R^a$. In another class of this embodiment, $R^1$ is independently selected from: biphenyl, and indole, wherein each biphenyl and indole is unsubstituted or substituted with 1 or 2 substituents independently selected from $R^a$. In another class of this embodiment, $R^1$ is independently selected from: biphenyl, and indole, wherein each biphenyl and indole is unsubstituted or substituted with 1 substituent independently selected from $R^a$.

In another embodiment of the present invention, $R^1$ is biphenyl, wherein each phenyl is unsubstituted or substituted with 1, 2, 3 or 4 substituents independently selected from $R^a$. In another embodiment of the present invention, $R^1$ is biphenyl, wherein biphenyl is unsubstituted or substituted with 1 or 2 substituents independently selected from $R^a$. In another embodiment of the present invention, $R^1$ is biphenyl, wherein biphenyl is unsubstituted or substituted with 1 substituent independently selected from $R^a$. In a class of this embodiment, $R^1$ is biphenyl.

In another embodiment of the present invention, $R^2$ is halogen. In a class of this embodiment, $R^2$ is selected from the group consisting of: Br, F, and Cl. In another class of this embodiment, $R^2$ is selected from the group consisting of: F, and Cl. In another class of this embodiment, $R^2$ is F. In another class of this embodiment, $R^2$ is Cl. In another class of this embodiment, $R^2$ is Br.

In another embodiment of the present invention, $R^3$ and $R^4$ are each independently selected from: hydrogen, halogen, —$C_{1-6}$alkyl, —$C_{2-6}$alkenyl, —$C_{2-6}$alkynyl, —CN, —$CF_3$, —$OC_{1-6}$alkyl, —$SO_2C_{1-6}$alkyl, —$SO_2NHC_{1-6}$alkyl, and —C(O)$NHC_{1-6}$alkyl, wherein each alkyl is unsubstituted or substituted with 1, 2 or 3 halogens.

In another embodiment of the present invention, $R^3$ and $R^4$ are each independently selected from: hydrogen, halogen, —$C_{1-6}$alkyl, —$C_{2-6}$alkenyl, —$C_{2-6}$alkynyl, —CN, —$CF_3$, and —$OC_{1-6}$alkyl, wherein each alkyl is unsubstituted or substituted with 1, 2 or 3 halogens. In a class of this embodiment, $R^3$ and $R^4$ are each independently selected from: hydrogen, halogen, —$C_{1-6}$alkyl, —CN, —$CF_3$, and —$OC_{1-6}$alkyl, wherein each alkyl is unsubstituted or substituted with 1, 2 or 3 halogens.

In another embodiment of the present invention, $R^3$ and $R^4$ are each independently selected from: hydrogen, and halogen. In a class of this embodiment, $R^3$ and $R^4$ are each selected from the group consisting of: hydrogen, Br, F, and Cl. In another class of this embodiment, $R^3$ and $R^4$ are each selected from the group consisting of: hydrogen, F, and Cl. In another class of this embodiment, $R^3$ and $R^4$ are each selected from the group consisting of: hydrogen and F. In another class of this embodiment $R^3$ and $R^4$ are each halogen. In a subclass of this class, $R^3$ and $R^4$ are each selected from the group consisting of: Br, F, and Cl. In another subclass of this class, $R^3$ and $R^4$ are each selected from the group consisting of: F, and Cl. In another subclass of this class, $R^3$ and $R^4$ are each F. In another subclass of this class, $R^3$ and $R^4$ are each Cl. In another class of this embodiment $R^3$ and $R^4$ are each hydrogen.

In another embodiment of the present invention, $R^3$ is each independently selected from: hydrogen, and halogen. In a class of this embodiment, $R^3$ is hydrogen. In another class of this embodiment, $R^3$ is each independently selected from: hydrogen, Br, Cl and F. In another class of this embodiment, $R^3$ is each independently selected from: hydrogen, Cl and F. In another class of this embodiment, $R^3$ is each independently selected from: hydrogen and F. In another class of this embodiment $R^3$ is halogen. In a subclass of this class, $R^3$ is selected from the group consisting of Br, F, and Cl. In another subclass of this class, $R^3$ is selected from the group consisting of F, and Cl. In another subclass of this class, $R^3$ is F. In another subclass of this class, $R^3$ is Cl. In another class of this embodiment $R^3$ is hydrogen, provided that if $R^2$ is hydrogen, then at least one of $R^3$ and $R^4$ is not hydrogen.

In another embodiment of the present invention, $R^4$ is each independently selected from: hydrogen, and halogen. In another class of this embodiment, $R^4$ is each independently selected from: hydrogen, Br, Cl and F. In another class of this embodiment, $R^4$ is each independently selected from: hydrogen, Cl and F. In another class of this embodiment, $R^4$ is each independently selected from: hydrogen and F. In another class of this embodiment $R^4$ is halogen. In a subclass of this class, $R^4$ is selected from the group consisting of Br, F, and Cl. In another subclass of this class, $R^4$ is selected from the group consisting of: F, and Cl. In another subclass of this class, $R^4$ is F. In another subclass of this class, $R^4$ is Cl. In another class of this embodiment $R^4$ is hydrogen, provided that if $R^2$ is hydrogen, then at least one of $R^3$ and $R^4$ is not hydrogen. In another embodiment of the present invention, $R^4$ is hydrogen.

In another embodiment of the present invention, $R^3$ is hydrogen or halogen; and $R^4$ is hydrogen.

In another embodiment of the present invention, $R^5$ is selected from: hydrogen, —$C_{1-6}$alkyl, —$CH_2CO_2H$, and —$CH_2CO_2C_{1-6}$alkyl. In a class of this embodiment, each $R^5$ is independently selected from: hydrogen, and —$C_{1-6}$alkyl. In another class of this embodiment, each $R^5$ is —$C_{1-6}$alkyl. In another class of this embodiment, each $R^5$ is hydrogen.

In another embodiment of the present invention, $R^3$ is hydrogen or halogen; and $R^4$ is hydrogen, and each $R^5$ is hydrogen.

In another embodiment of the present invention, each $R^a$ is independently selected from the group consisting of: hydrogen, halogen, —$(CH_2)_mOH$, —$(CF_{12})_mN(R^j)_2$, —$(CH_2)_mCN$, —$C_{1-6}$alkyl, —$(CH_2)_mCF_3$, —$(CH_2)_mOCF_3$, —$(CH_2)_mSC_{1-6}$alkyl, —$(CH_2)_mS(O)_2C_{1-6}$alkyl, —$(CH_2)_mS(O)_2N(C_{1-6}$alkyl$)_2$, —$(CH_2)_mC(O)N(R^j)_2$, —$(CH_2)_mN(R^j)C(O)R^f$, —$(CH_2)_mC(O)R^f$, —$(CH_2)_mCO_2R^f$, —$(CH_2)_mOC(O)R^f$, —$(CH_2)_mC_{3-7}$cycloalkyl, —$(CH_2)_mC_{3-7}$cycloalkenyl, —$(CH_2)_mC_{2-6}$cycloheteroalkyl, —$(CH_2)_mC_{2-6}$cycloheteroalkenyl, —$(CH_2)_m$aryl, and —$(CH_2)_m$heteroaryl, wherein each $CH_2$ is unsubstituted or substituted with 1 or 2 substituents selected from: oxo, —$(CH_2)_{0-3}OH$, —CN, —$C_{1-6}$alkyl, —$OC_{1-6}$alkyl, halogen, —$CH_2F$, $CF_3$, and —$CO_2C_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —$(CH_2)_{0-3}OH$, —CN, —$C_{1-6}$alkyl, —$OC_{1-6}$alkyl, halogen, —$CH_2F$, —$CHF_2$, —$CF_3$, and —$CO_2C_{1-6}$alkyl. In a class of this embodiment, each $R^a$ is independently selected from the group consisting of: hydrogen, —$(CH_2)_mOH$, —$(CH_2)_mCN$, —$C_{1-6}$alkyl, —$(CH_2)_mC(O)N(R^j)_2$, —$(CH_2)_mN(R^j)C(O)R^f$, —$(CH_2)_mC(O)R^f$, —$(CH_2)_mC_{3-7}$cycloalkyl, and —$(CH_2)_m$heteroaryl, wherein each $CH_2$ is unsubstituted or substituted with 1 or 2 substituents selected from: oxo, —$(CH_2)_{0-3}OH$, —CN, —$C_{1-6}$alkyl, —$OC_{1-6}$alkyl, halogen, —$CH_2F$, —$CHF_2$, —$CF_3$ and —$CO_2C_{1-6}$alkyl, and wherein alkyl, cycloalkyl, and heteroaryl are unsubstituted or substituted with 1, 2, 3 or 4 substituents selected from: oxo, —$(CH_2)_{0-3}OH$, —CN, —$C_{1-6}$ alkyl, —$OC_{1-6}$alkyl, halogen, —$CH_2F$, —$CHF_2$, —$CF_3$ and —$CO_2C_{1-6}$alkyl. In a subclass of this class, alkyl, cycloalkyl, and heteroaryl are unsubstituted or substituted with 1, 2 or 3 substituents selected from: —OH. In another subclass of this class, alkyl, cycloalkyl, and heteroaryl are unsubstituted or substituted with one substituent selected from: —OH.

In another class of this embodiment, each $R^a$ is independently selected from the group consisting of: hydrogen, —OH, —CN, —$C_{1-6}$alkyl, —$C(O)N(R^j)_2$, —$N(R^j)C(O)R^f$, —$C(O)R^f$, —$C_{3-7}$cycloalkyl, and -heteroaryl, wherein alkyl, cycloalkyl and heteroaryl are unsubstituted or substituted with 1, 2, 3 or 4 substituents selected from: oxo, —$(CH_2)_{0-3}OH$, —CN, —$C_{1-6}$alkyl, —$OC_{1-6}$alkyl, halogen, —$CH_2F$, —$CHF_2$, —$CF_3$ and —$CO_2C_{1-6}$alkyl. In a subclass of this class, alkyl, cycloalkyl, and heteroaryl are unsubstituted or substituted with 1, 2 or 3 substituents selected from: —OH. In another subclass of this class, alkyl, cycloalkyl, and heteroaryl are unsubstituted or substituted with one substituent selected from: —OH.

In another class of this embodiment, each $R^a$ is independently selected from the group consisting of: hydrogen, —$(CH_2)_mOH$, —$C_{1-6}$alkyl, —$(CH_2)_mC(O)N(R^j)_2$, —$(CH_2)_m C(O)R^f$, —$(CH_2)_mC_{3-7}$cycloalkyl, and —$(CH_2)_m$heteroaryl, wherein each $CH_2$ is unsubstituted or substituted with 1 or 2 substituents selected from: oxo, —$(CH_2)_{0-3}OH$, —CN, —$C_{1-6}$alkyl, —$OC_{1-6}$alkyl, halogen, —$CH_2F$, —$CHF_2$, —$CF_3$, and —$CO_2C_{1-6}$alkyl, and wherein alkyl, cycloalkyl, and heteroaryl are unsubstituted or substituted with 1, 2, 3 or 4 substituents selected from: oxo, —$(CH_2)_{0-3}$ OH, —CN, —$C_{1-6}$alkyl, —$OC_{1-6}$alkyl, halogen, —$CH_2F$, —$CHF_2$, —$CF_3$, and —$CO_2C_{1-6}$alkyl. In a subclass of this class, alkyl, cycloalkyl, and heteroaryl are unsubstituted or substituted with 1, 2 or 3 substituents selected from: —OH. In another subclass of this class, alkyl, cycloalkyl, and heteroaryl are unsubstituted or substituted with one substituent selected from: —OH.

In another class of this embodiment, each $R^a$ is independently selected from the group consisting of: hydrogen, —OH, —$C_{1-6}$alkyl, —C(O)N($R^j$)$_2$, —C(O)$R^f$, —$C_{3-7}$cycloalkyl, and -heteroaryl, wherein alkyl, cycloalkyl, and heteroaryl are unsubstituted or substituted with 1, 2, 3 or 4 substituents selected from: oxo, —(CH$_2$)$_{0-3}$OH, —CN, —NH$_2$, —NH(C$_{1-6}$alkyl), —N(C$_{1-6}$alkyl)$_2$, —OC$_{1-6}$alkyl, halogen, —CH$_2$F, —CHF$_2$, —CF$_3$, —CO$_2$H, and —CO$_2$C$_{1-6}$alkyl. In a subclass of this class, alkyl, cycloalkyl, and heteroaryl are unsubstituted or substituted with 1, 2, 3 or 4 substituents selected from: —OH. In another subclass of this class, alkyl, cycloalkyl, and heteroaryl are unsubstituted or substituted with one substituent selected from: —OH.

In another class of this embodiment, each $R^a$ is independently selected from the group consisting of hydrogen, —OH, —CH$_3$, —C(O)—NH-tetrahydropyran, —C(O)—NH-tetrahydrofuran, —C(O)-piperidine, —C(O)-morpholine, —C(O)-pyrrolidine, -cyclopropyl, and -pyridine, wherein alkyl, cycloalkyl, cycloheteroalkyl and heteroaryl are unsubstituted or substituted with 1, 2 or 3 substituents selected from: oxo, —(CH$_2$)$_{0-3}$OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl. In a subclass of this class, alkyl, cycloalkyl, cycloheteroalkyl and heteroaryl are unsubstituted or substituted with 1, 2 or 3 substituents selected from: —OH. In another subclass of this class, alkyl, cycloalkyl, cycloheteroalkyl and heteroaryl are unsubstituted or substituted with one substituent selected from: —OH.

In another embodiment of the present invention, each $R^b$ is independently selected from: hydrogen, —C$_{1-6}$alkyl, aryl, heteroaryl, —C$_{3-6}$cycloalkyl, —C$_{3-6}$cycloalkenyl, —C$_{3-6}$cycloheteroalkyl, halogen, —OH, —OC$_{1-6}$alkyl, —CF$_3$, —CN, and —SO$_2$C$_{1-6}$alkyl, wherein each alkyl, aryl, heteroaryl, cycloalkyl, cycloalkenyl and cycloheteroalkyl is unsubstituted or substituted with 1, 2 or 3 halogens. In another embodiment of the present invention, each $R^b$ is independently selected from: hydrogen, —C$_{1-6}$alkyl, aryl, —C$_{3-6}$cycloalkyl, —C$_{3-6}$cycloalkenyl, —C$_{3-6}$cycloheteroalkyl, halogen, —OH, —OC$_{1-6}$alkyl, —CF$_3$, —CN, and —SO$_2$C$_{1-6}$alkyl, wherein each alkyl, aryl, cycloalkyl, cycloalkenyl and cycloheteroalkyl is unsubstituted or substituted with 1, 2 or 3 halogens.

In another embodiment of the present invention, each $R^b$ is independently selected from: hydrogen, —C$_{1-6}$alkyl, aryl, and —C$_{3-6}$cycloalkyl, wherein each alkyl, cycloalkyl, cycloalkenyl and cycloheteroalkyl is unsubstituted or substituted with 1, 2 or 3 halogens.

In another embodiment of the present invention, each $R^b$ is independently selected from: hydrogen, —C$_{1-6}$alkyl, phenyl, and —C$_{3-6}$cycloalkyl, wherein each alkyl, cycloalkyl, cycloalkenyl and cycloheteroalkyl is unsubstituted or substituted with 1, 2 or 3 halogens.

In another embodiment of the present invention, each $R^b$ is independently selected from: hydrogen, —C$_{1-6}$alkyl, and —C$_{3-6}$cycloalkyl, wherein each alkyl and cycloalkyl is unsubstituted or substituted with 1, 2 or 3 halogens. In another embodiment of the present invention, each $R^b$ is independently selected from: hydrogen, —C$_{1-6}$alkyl, halogen, —OH, —OC$_{1-6}$alkyl, —CF$_3$, —CN, and —SO$_2$C$_{1-6}$alkyl, wherein each alkyl is unsubstituted or substituted with 1, 2 or 3 halogens. In another embodiment of the present invention, each $R^b$ is independently selected from: hydrogen, and —C$_{1-6}$alkyl, wherein each alkyl is unsubstituted or substituted with 1, 2 or 3 halogens. In a class of this embodiment, each $R^b$ is independently selected from: hydrogen and methyl. In another class of this embodiment, each $R^b$ is hydrogen. In another class of this embodiment, each $R^b$ is methyl.

In another embodiment of the present invention, each $R^c$ is independently selected from: hydrogen, halogen, oxo, —(CH$_2$)$_r$OH, —(CH$_2$)$_r$N($R^e$)$_2$, —(CH$_2$)$_r$CN, —C$_{1-6}$alkyl, —CF$_3$, —(CH$_2$)$_r$C$_{3-7}$cycloalkyl, and —(CH$_2$)$_r$C$_{2-6}$cycloheteroalkyl, wherein each CH$_2$ is unsubstituted or substituted with 1 or 2 substituents selected from: oxo, —OH, —CN, —C$_{1-6}$alkyl, —OC$_{1-6}$alkyl, halogen, —CH$_2$F, —CHF$_2$, and —CF$_3$, and wherein alkyl, cycloalkyl, and cycloheteroalkyl are unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$.

In another embodiment of the present invention, each $R^c$ is independently selected from: hydrogen, halogen, oxo, —OH, —N($R^e$)$_2$, —CN, —C$_{1-6}$alkyl, —CF$_3$, —C$_{3-7}$cycloalkyl, and —C$_{2-6}$cycloheteroalkyl, wherein alkyl, cycloalkyl and cycloheteroalkyl are unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$.

In another embodiment of the present invention, each $R^c$ is independently selected from: hydrogen, halogen, oxo, —OH, —N($R^e$)$_2$, —CN, —C$_{1-6}$alkyl, and —CF$_3$, wherein alkyl is unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$.

In another embodiment of the present invention, each $R^c$ is independently selected from: hydrogen, halogen, oxo, —OH, —NH$_2$, —CN, —C$_{1-6}$alkyl, and —CF$_3$, wherein alkyl is unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$.

In another embodiment of the present invention, each $R^c$ is independently selected from: hydrogen and —C$_{1-6}$alkyl, wherein alkyl is unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$. In a class of this embodiment, each $R^c$ is independently selected from: hydrogen and —C$_{1-6}$alkyl. In another class of this embodiment, $R^c$ is hydrogen. In another class of this embodiment, $R^c$ is —C$_{1-6}$alkyl.

In another embodiment of the present invention, each $R^d$ is independently selected from: hydrogen and —C$_{1-6}$alkyl. In a class of this embodiment, each $R^d$ is hydrogen. In another class of this embodiment, each $R^d$ is C$_{1-6}$alkyl.

In another embodiment of the present invention, each $R^e$ is independently selected from: hydrogen, and —C$_{1-6}$alkyl, wherein alkyl is unsubstituted or substituted with 1, 2, 3 or 4 substituents selected from: —OH, oxo, halogen, C$_{1-6}$alkyl, and —OC$_{1-6}$alkyl. In a class of this embodiment, each $R^e$ is independently selected from: hydrogen, and C$_{1-6}$alkyl. In a class of this embodiment, each $R^e$ is hydrogen. In another class of this embodiment, each $R^e$ is C$_{1-6}$alkyl, wherein alkyl is unsubstituted or substituted with 1, 2, 3 or 4 substituents selected from: —OH, oxo, halogen, C$_{1-6}$alkyl, and —OC$_{1-6}$alkyl. In another class of this embodiment, each $R^e$ is C$_{1-6}$alkyl.

In another embodiment of the present invention, each $R^f$ is independently selected from: C$_{1-6}$alkyl, C$_{4-7}$cycloalkyl, C$_{4-7}$cycloalkenyl, C$_{3-7}$cycloheteroalkyl, C$_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: —OH, —CN, —$C_{1-6}$alkyl, —$OC_{1-6}$alkyl, halogen, —$CH_2F$, —$CHF_2$, and —$CF_3$.

In another embodiment of the present invention, each $R^f$ is independently selected from: $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, wherein alkyl, cycloalkyl, cycloalkenyl, cycloheteroalkyl, and cycloheteroalkenyl, are unsubstituted or substituted with 1, 2, 3 or 4 substituents selected from: oxo, —OH, —CN, —$C_{1-6}$alkyl, —$OC_{1-6}$alkyl, halogen, —$CH_2F$, —$CHF_2$, and —$CF_3$.

In another embodiment of the present invention, each $R^f$ is independently selected from: $C_{1-6}$alkyl, and $C_{3-7}$cycloheteroalkyl, wherein alkyl and cycloheteroalkyl are unsubstituted or substituted with 1, 2, 3 or 4 substituents selected from: oxo, —OH, —CN, —$C_{1-6}$alkyl, —$OC_{1-6}$alkyl, halogen, —$CH_2F$, —$CHF_2$, and —$CF_3$. In a class of this embodiment, each $R^f$ is independently selected from: $C_{1-6}$alkyl, piperidine, morpholine, and pyrrolidine, wherein alkyl, piperidine, morpholine, and pyrrolidine are unsubstituted or substituted with 1, 2, 3 or 4 substituents selected from: oxo, —CN, —$C_{1-6}$alkyl, —$OC_{1-6}$alkyl, halogen, —$CH_2F$, —$CHF_2$, and —$CF_3$.

In another embodiment of the present invention, each $R^f$ is independently selected from: $C_{3-7}$cycloheteroalkyl, wherein cycloheteroalkyl is unsubstituted or substituted with 1, 2, 3 or 4 substituents selected from: oxo, —OH, —CN, —$C_{1-6}$alkyl, —$OC_{1-6}$alkyl, halogen, —$CH_2F$, —$CHF_2$, and —$CF_3$. In a class of this embodiment, each $R^f$ is independently selected from: piperidine, morpholine, and pyrrolidine, wherein piperidine, morpholine, and pyrrolidine are unsubstituted or substituted with 1, 2, 3 or 4 substituents selected from: oxo, —OH, —CN, —$C_{1-6}$alkyl, 6alkyl, halogen, —$CH_2F$, —$CHF_2$, and —$CF_3$.

In another embodiment of the present invention, each $R^i$ is independently selected from: hydrogen, $C_{1-6}$alkyl, $C_{4-7}$cycloalkyl, $C_{4-7}$cycloalkenyl, $C_{3-7}$cycloheteroalkyl, $C_{3-7}$cycloheteroalkenyl, aryl, and heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$C_{1-6}$ alkyl, —$OC_{1-6}$alkyl, halogen, —$CH_2F$, —$CHF_2$, —$CF_3$, —$CO_2H$, —$CO_2C_{1-6}$alkyl, —$OCOC_{1-6}$alkyl, and —$OCO_2C_{1-6}$alkyl. In a class of this embodiment, $R^i$ is independently selected from: hydrogen, and —$C_{1-6}$alkyl, wherein alkyl is unsubstituted or substituted with 1, 2, 3 or 4 substituents selected from: oxo, —OH, —CN, —$NH_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$OCOC_{1-6}$alkyl, and —$OCO_2C_{1-6}$alkyl. In another class of this embodiment, $R^i$ is independently selected from: hydrogen and —$CH_3$, wherein alkyl is unsubstituted or substituted with 1, 2 or 3 substituents selected from: oxo, —OH, —CN, —$NH_2$, —$C_{1-6}$alkyl, —$OC_{1-6}$alkyl, halogen, —$CH_2F$, $CHF_2$, —$CF_3$, —$CO_2H$, —$CO_2C_{1-6}$alkyl, —$OCOC_{1-6}$alkyl, and —$OCO_2C_{1-6}$alkyl. In another class of this embodiment, $R^i$ independently selected from: hydrogen, and —$CH_3$.

In another embodiment of the present invention, each $R^j$ is independently selected from: hydrogen, —$C_{1-6}$alkyl, —$C_{3-6}$cycloalkyl, and —$C_{3-6}$cycloheteroalkyl, wherein alkyl, cycloalkyl and cycloheteroalkyl are unsubstituted or substituted with 1, 2, 3 or 4 substituents selected from: —OH, oxo, halogen, $C_{1-6}$alkyl, —$OC_{1-6}$alkyl, $NH_2$, —$NH(C_{1-6}$alkyl), and —$N(C_{1-6}$alkyl)$_2$. In a class of this embodiment, each $R^j$ is independently selected from: hydrogen, and —$C_{3-6}$cycloheteroalkyl, wherein alkyl and cycloheteroalkyl are unsubstituted or substituted with 1, 2, 3 or 4 substituents selected from: —OH, oxo, halogen, $C_{1-6}$alkyl, —$OC_{1-6}$alkyl, —$NH_2$, —$NH(C_{1-6}$alkyl), and —$N(C_{1-6}$alkyl)$_2$. In another class of this embodiment, each $R^j$ is independently selected from: hydrogen, tetrahydrofuran, and tetrahydropyran, wherein each cycloheteroalkyl is unsubstituted or substituted with 1, 2, or 3 substituents selected from: —OH, oxo, halogen, $C_{1-6}$alkyl, —$OC_{1-6}$alkyl, —$NH_2$, —$NH(C_{1-6}$alkyl), and —$N(C_{1-6}$alkyl)$_2$. In another class of this embodiment, each $R^j$ is independently selected from: hydrogen, tetrahydrofuran, and tetrahydropyran. In another class of this embodiment, each $R^j$ is hydrogen. In another class of this embodiment, each $R^j$ is independently selected from: —$C_{3-6}$cycloheteroalkyl, wherein each cycloheteroalkyl is unsubstituted or substituted with 1, 2, 3 or 4 substituents selected from: —OH, oxo, halogen, $C_{1-6}$alkyl, —$OC_{1-6}$alkyl, —$NH_2$, —$NH(C_{1-6}$alkyl), and —$N(C_{1-6}$alkyl)$_2$. In another class of this embodiment, each $R^j$ is independently selected from: tetrahydrofuran and tetrahydropyran, wherein each cycloheteroalkyl is unsubstituted or substituted with 1, 2, 3 or 4 substituents selected from: —OH, oxo, halogen, $C_{1-6}$alkyl, —$OC_{1-6}$alkyl, —$NH_2$, —$NH(C_{1-6}$alkyl), and —$N(C_{1-6}$alkyl)$_2$. In another class of this embodiment, each $R^j$ is independently selected from: tetrahydrofuran, and tetrahydropyran.

In another embodiment of the present invention, n is 0, 1, 2, 3 or 4. In a class of this embodiment, n is 1, 2 or 3. In another class of this embodiment, n is 0, 1 or 2. In another class of this embodiment, n is 0. In another class of this embodiment, n is 1. In another class of this embodiment, n is 2. In another class of this embodiment, n is 3. In another class of this embodiment, n is 4.

In another embodiment of the present invention, m is 0, 1, 2, 3, or 4. In a class of this embodiment, m is 1, 2 or 3. In another class of this embodiment, m is 0, 1 or 2. In another class of this embodiment, m is 0 or 1. In another class of this embodiment, m is 0. In another class of this embodiment, m is 1. In another class of this embodiment, m is 2. In another class of this embodiment, m is 3. In another class of this embodiment, m is 4.

In another embodiment of the present invention, p is 0, 1, 2 or 3. In a class of this embodiment, p is 1, 2 or 3. In another class of this embodiment, p is 0, 1 or 2. In another class of this embodiment, p is 0 or 2. In another class of this embodiment, p is 0. In another class of this embodiment, p is 1. In another class of this embodiment, p is 2. In another class of this embodiment, p is 3.

In another embodiment of the present invention, q is 0, 1, 2, 3 or 4. In a class of this embodiment, q is 1, 2 or 3. In another class of this embodiment, q is 0, 1 or 2. In another class of this embodiment, q is 1 or 2. In another class of this embodiment, q is 0. In another class of this embodiment, q is 1. In another class of this embodiment, q is 2.

In another embodiment of the present invention, r is 0, 1 or 2. In a class of this embodiment, r is 0 or 1. In another class of this embodiment, r is 1 or 2. In another class of this embodiment, r is 0. In another class of this embodiment, r is 1. In another class of this embodiment, r is 2.

In another embodiment of the present invention, s is 0, 1, 2, 3 or 4. In a class of this embodiment, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3. In another class of this embodiment, s is 4.

In another embodiment of the present invention, t is 0, 1, 2, 3 or 4. In a class of this embodiment, t is 0, 1, 2 or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3. In another class of this embodiment, t is 4.

In another embodiment of the present invention, the invention relates to compounds of structural formula Ia:

(Ia)

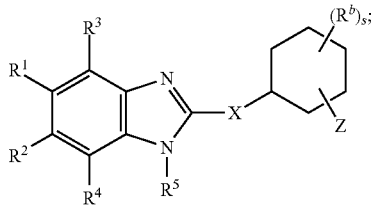

or a pharmaceutically acceptable salt thereof.

In another embodiment of the present invention, the invention relates to compounds of structural formula Ib:

(Ib)

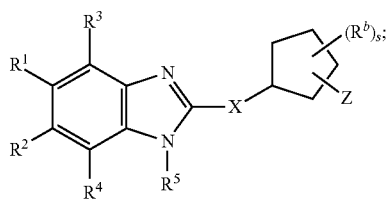

or a pharmaceutically acceptable salt thereof.

In another embodiment of the present invention, the invention relates to compounds of structural formula Ic:

(Ic)

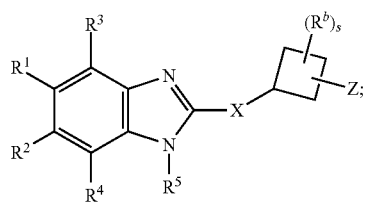

or a pharmaceutically acceptable salt thereof.

In another embodiment of the present invention, the invention relates to compounds of structural formula Id:

(Id)

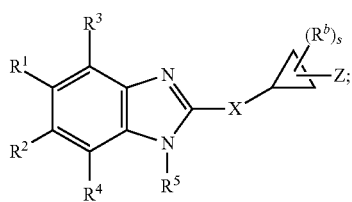

or a pharmaceutically acceptable salt thereof.

In another embodiment of the present invention, the invention relates to compounds of structural formula Ie:

(Ie)

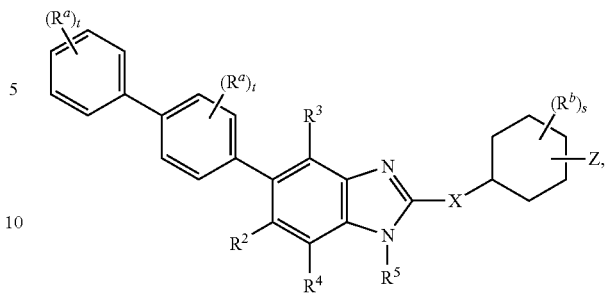

or a pharmaceutically acceptable salt thereof.

In another embodiment of the present invention, the invention relates to compounds of structural formula If:

(If)

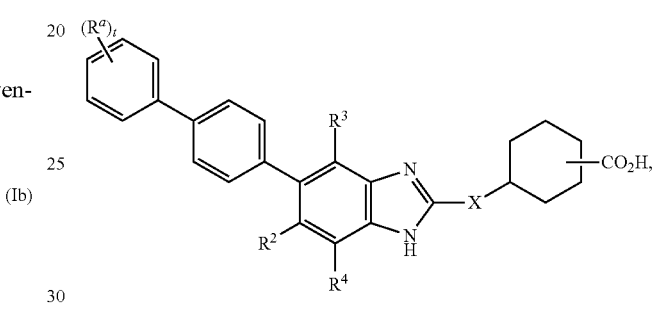

or a pharmaceutically acceptable salt thereof.

In another embodiment of the present invention, the invention relates to compounds of structural formula Ig:

(Ig)

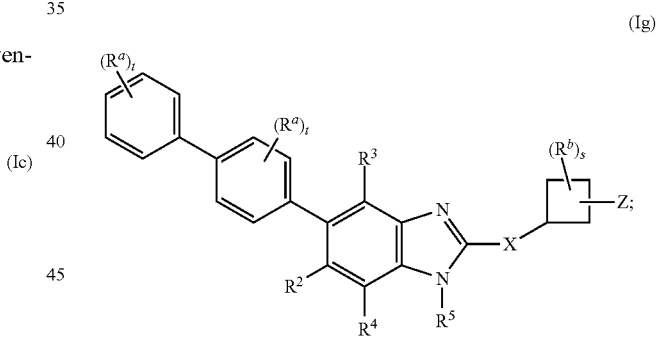

or a pharmaceutically acceptable salt thereof.

In another embodiment of the present invention, the invention relates to compounds of structural formula Ih:

(Ih)

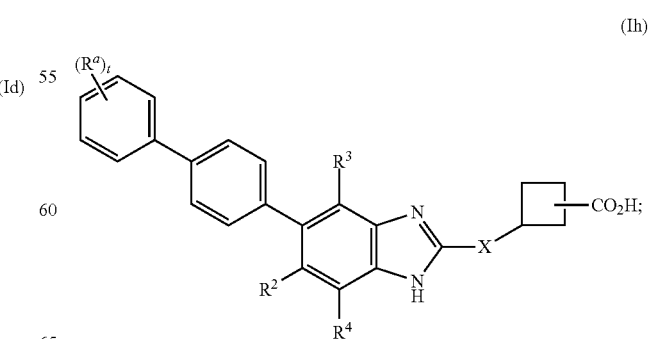

or a pharmaceutically acceptable salt thereof.

The compound of structural formula I, includes the compounds of structural formulas Ia, Ib, Ic, Id, Ie, If, Ig and Ih, and pharmaceutically acceptable salts, hydrates and solvates thereof.

In one class of the embodiments of the compounds of structural formulas Ia through Ih of the present invention:
X is selected from:
 (1) —O—, and
 (2) —O—CH$_2$—;
Y is selected from the group consisting of:
 (1) cyclopropyl,
 (2) cyclobutyl,
 (3) cyclopentyl, and
 (4) cyclohexyl,
wherein each cyclopropyl, cyclobutyl, cyclopentyl, and cyclohexyl is unsubstituted or substituted with 1, 2 or 3 substituents selected from R$^b$;
Z is —CO$_2$H;
R$^1$ is independently selected from:
 (1) phenyl,
 (2) biphenyl, and
 (3) heteroaryl,
wherein each phenyl, biphenyl and heteroaryl is unsubstituted or substituted with 1, 2, 3 or 4 substituents independently selected from R$^a$;
R$^2$ is halogen;
R$^3$ and R$^4$ are each independently selected from:
 (1) hydrogen, and
 (2) halogen; and
R$^5$ is hydrogen;
or a pharmaceutically acceptable salt thereof.

In another class of the embodiments of the compounds of structural formulas Ia through Ih of the present invention:
X is selected from:
 (1) —O—, and
 (2) —O—CH$_2$—;
Y is selected from the group consisting of:
 (1) cyclohexyl, and
 (2) cyclobutyl,
wherein each cyclohexyl and cyclobutyl is unsubstituted or substituted with 1, 2 or 3 substituents selected from R$^b$;
Z is —CO$_2$H;
R$^1$ is biphenyl, wherein biphenyl is unsubstituted or substituted with 1, 2 or 3 substituents independently selected from R$^a$;
R$^2$ is halogen;
R$^3$ is hydrogen or halogen;
R$^4$ is hydrogen; and
R$^5$ is hydrogen;
or a pharmaceutically acceptable salt thereof.

Illustrative, but non-limiting, examples of the compounds of the present invention that are useful as activators of AMP-protein kinase are the following benzimidazoles.

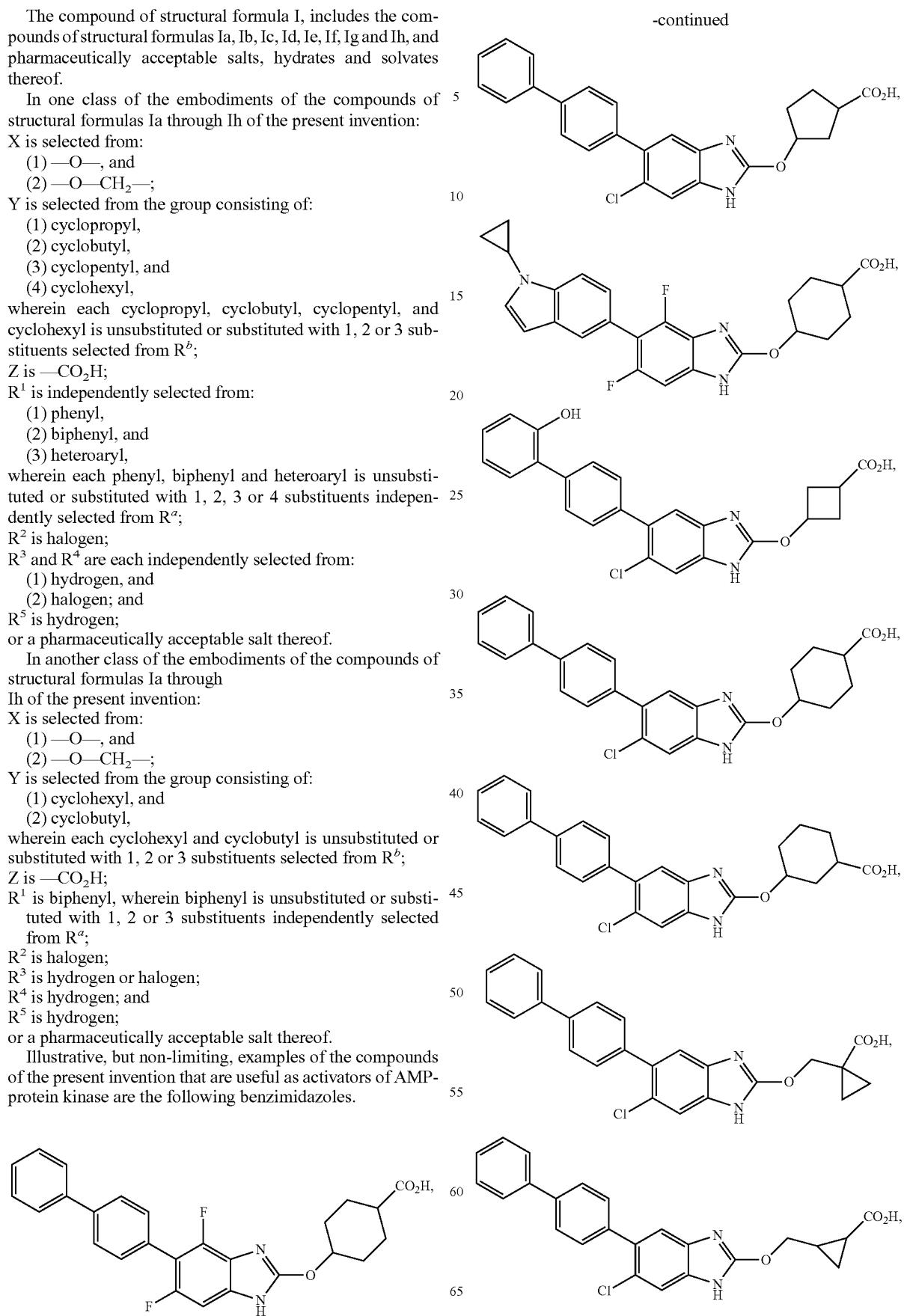

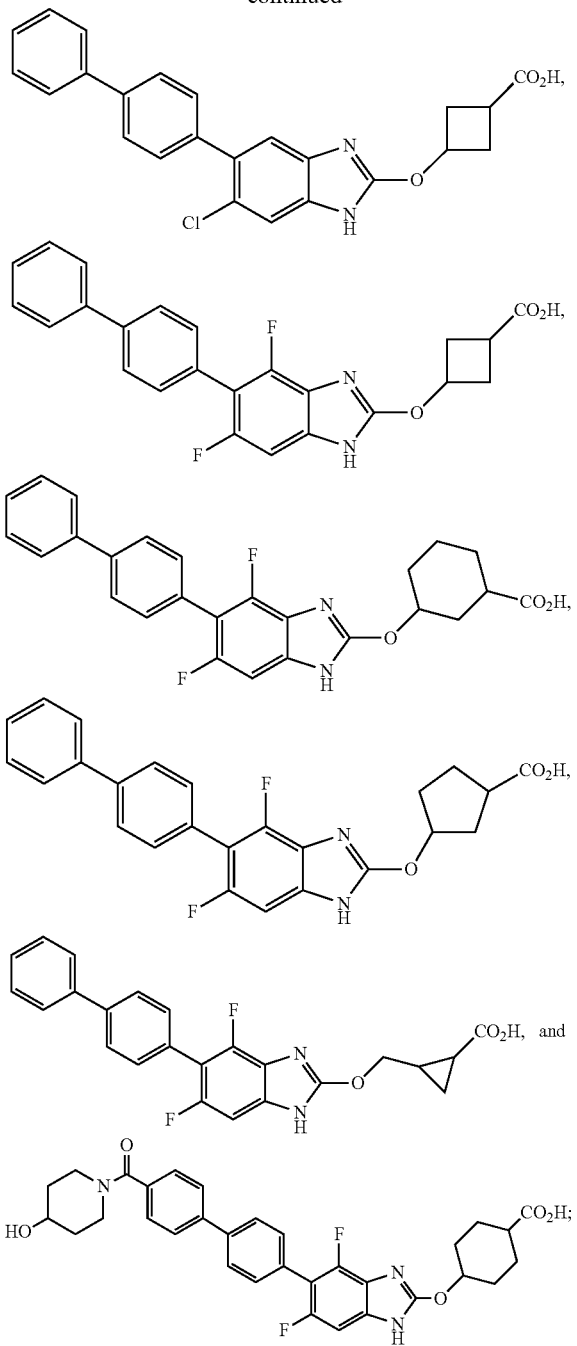

or a pharmaceutically acceptable salt thereof.

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains up to 10 carbons which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is vinyl.

"Alkynyl" means carbon chains up to 10 carbons which contain at least one carbon-carbon triple bond, and which may be linear or branched or combinations thereof. Examples of alkynyl include ethynyl, propargyl, 3-methyl-1-pentynyl, 2-heptynyl and the like. In one embodiment of the present invention, alkynyl is ethynyl.

"Cycloalkyl" means mono- or bicyclic or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like. In one embodiment of the present invention, cycloalkyl is selected from cyclopentyl and cyclohexyl. In another embodiment of the present invention, cycloalkyl is selected from cyclopropyl, cyclopentyl, and cyclohexyl.

"Cycloalkenyl" means nonaromatic, mono- or bicyclic or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooxtenyl, decahydronaphthyl, bicyclo[2.2.1]hept-5-en-2-yl, and the like.

"Cycloheteroalkyl" means nonaromatic, mono- or bicyclic or bridged saturated carbocyclic rings, each having from 2 to 14 carbon atoms and containing 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from piperidine, pyrrolidine, oxazolidine, 1,3-oxazolidine-2,4-dione, thiazolidine, 1,3-thiazolidine-2,4-dione, imidazolidine, and hydantoin, and the like. In another embodiment of the present invention cycloheteroalkyl is selected from: morpholine, pyrrolidine, piperazine, and piperidine. In another embodiment of the present invention, cycloheteroalkyl is imidazolidine.

"Cycloheteroalkenyl" means nonaromatic mono- or bicyclic or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryl thus includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as acycloheteroalkyl or cycloheteroalkenyl ring. Examples of heteroaryls include: pyrazole, pyridine, pyrazine, pyrimidine, thiazole, thiophene, benzoimidazole, quinoline, isoquinoline, indole, indazole, carbazole, benzotriazole, benzofuran, benzothiazole, benzothiophene, benzoisooxazole, oxazole, furan, benzoxazole, isoxazole, indoline, isoindoline, tetrazole, imidazole, oxadiazole, thiadiazole, triazole, benzothiazole, bernzopyrazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. In one embodiment of the present invention, heteroaryl is selected from: imidazole, pyrazole, pyridine, pyrazine, pyrimidine, thiazole, thiophene, benzoimidazole, quinoline, isoquinoline, indole, indazole, carbazole, benzotriazole, benzofuran, benzothiazole, benzo[b]thiophene, benzo[d]isooxazole, 3,4-dihydro-2H-benzo[1,4]oxazine, benzo[1,3]dioxole, benzo[1,4]dioxine, 1H-pyrrolo[2,3-b]pyridine, 1,6-dihydro-pyridine, [1,2,4]triazolo[4,3-a]pyridine, 3,4 dihydropyrido[3,2-b][1,4]oxazine, 3,4-dihydro-2H-1,4-benzoxazine, 2,3-dihydro-1H-indole, 2,3-dihydro-1H-isoindole, 2,3-dihydrobenzoimidazole, 1,2-dihydroquinoline, 1,2,3,4-tetrahydroisoquinoline, 1,2,3,4-tetrahydrocyclopenta[b]indole, 1,2,3,4-tetrahydroquinoxaline, and 1,2,3,6-tetrahydropyridine. In another embodiment of the present invention, heteroaryl is tetrazole. In another embodiment, heteroaryl is selected from: pyrazole, pyridine, pyrimidine, isoxazole, imidazole, oxazole, triazole, tetrazole, oxadiazole, thiazole, thiadiazole, and benzoxazole. In another embodiment of this invention, heteroaryl is tetrazole.

"Halogen" includes fluorine, chlorine, bromine and iodine. In one embodiment of the present invention, halogen is selected from fluorine, chlorine, and bromine.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkylcarbonylamino $C_{1-6}$ alkyl substituent is equivalent to:

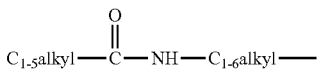

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

In the compounds of structural formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amities, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. The term "pharmaceutically acceptable salt" is not limited to mono salts, it includes, but is not limited to, di and tri salts.

It will be understood that, as used herein, references to the compounds of Formula I are meant to also include the pharmaceutically acceptable salts.

Compounds of the present invention are activators of the AMP-activated protein kinase. The methods of treatment of this invention comprises a method of activating AMPK-activated protein kinase and treating AMPK-activated protein kinase mediated diseases by administering to a patient in need of such treatment a non-toxic therapeutically effective amount of a compound of this invention that activate AMPK-activated protein kinase.

AMP-activated protein kinase (AMPK) is a heterotrimeric enzyme composed of a catalytic α subunit and regulatory β and γ subunits. There are two genes encoding isoforms of both the α and β subunits (α1, α2, β1 and β2) and three genes encoding isoforms of the γ subunit (γ1, γ2 and γ3) leading to 12 possible heterotrimeric combinations. The α2 isoform is predominately found in skeletal and cardiac muscle AMPK; both the α1 and α2 isoforms are found in hepatic AMPK; while in pancreatic islet β-cells the α1 isoform AMPK predominates. In particular, the compounds of structural formula I are activators of at least one heterotrimeric isoform of AMP-activated protein kinase.

An "activator" is a compound that either increases the activity (phosphorylation of downstream substrates) of fully phosphorylated AMPK or that increases the phosphorylation of AMPK.

The compounds of the present invention are efficacious in the treatment and prevention of diseases, disorders and conditions responsive to the activation of AMP-activated protein kinase, including but not limited to: type 2 diabetes, insulin resistance, hyperglycemia, obesity, hyperinsulinemia, glucose intolerance, atherosclerosis, Metabolic Syndrome, hypertension, high hepatic glucose output, high blood glucose concentrations, nonalcoholic steatohepatitis, protection against ischemia and reperfusion damage, and lipid disorders, such as dyslipidemia, elevated levels of plasma triglycerides, elevated levels of free fatty acids, elevated levels of cholesterol, high levels of low density lipoprotein (LDL) and low levels of high density lipoprotein (HDL). The compounds are also useful for the treatment of cancer, hypoxia and glucocorticoid-induced apoptosis.

One or more of the following diseases may be treated by the administration of a therapeutically effective amount of a compound of Formula I, or a pharmaceutically acceptable salt thereof, to a patient in need of treatment: (1) non-insulin dependent diabetes mellitus (Type 2 diabetes); (2) hyperglycemia; (3) Metabolic Syndrome; (4) obesity; (5) hypercholesterolemia; (6) hypertriglyceridemia (elevated levels of triglyceride-rich-lipoproteins); (7) mixed or diabetic dyslipidemia; (8) low HDL cholesterol; (9) high LDL cholesterol; (10) atherosclerosis; and (11) hypertension.

Also, the compounds of Formula I may be used for the manufacture of a medicament for treating one or more of the above diseases.

One embodiment of the uses of the compounds is directed to the treatment of one or more of the following diseases by administering a therapeutically effective amount to a patient in need of treatment: (1) Type 2 diabetes; (2) hyperglycemia; (3) Metabolic Syndrome; (4) obesity; (5) hypercholesterolemia; and (6) hypertension.

The compounds may also be used for manufacturing a medicament for use in the treatment of one or more of the above diseases.

The compounds are expected to be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, methods and medicaments as described herein may also be effective in reducing the risks of adverse sequelae associated with metabolic syndrome, and in reducing the risk of developing atherosclerosis, delaying the onset of atherosclerosis, and/or reducing the risk of sequelae of atherosclerosis. Sequelae of atherosclerosis include angina, claudication, heart attack, stroke, and others. By keeping hyperglycemia under control, the compounds may also be effective in delaying or preventing vascular restenosis and diabetic retinopathy.

The compounds of this invention may also have utility in improving or restoring β-cell function, so that they may be useful in treating type 1 diabetes or in delaying or preventing a patient with Type 2 diabetes from needing insulin therapy.

Other possible outcomes of treatment with the compounds of the present invention include, but are not limited to: 1) a decrease in fatty acid synthesis; 2) an increase in fatty acid oxidation and ketogenesis; 3) a decrease in cholesterol synthesis, lipogenesis, and triglyceride synthesis; 4) a decrease in blood glucose levels and concentration; 5) an improvement in glucose homeostasis; 6) a normalization of glucose metabolism; 7) a decrease in blood pressure; 8) an increase in HDL; 9) a decrease in plasma triglycerides; 10) a decrease in free fatty acids; 11) a decrease in hepatic glucose output; 12) an improvement in insulin action; 13) a decrease in blood pressure; 14) an improvement in insulin sensitivity; 15) a suppression of hepatic glucose output; 15) an inhibition of de novo lipogenesis; 16) stimulation of muscle glucose uptake; 17) modulation of insulin secretion by pancreatic β cells; and 16) a decrease in body weight.

The compounds generally may be efficacious in treating one or more of the following diseases: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure (hypertension), and (19) insulin resistance.

One aspect of the invention provides a method for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound having formula I. The compound may be used alone or advantageously may be administered with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example torcetrapib and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridernia, dyslipidemia, high LDL, and low HDL.

The present invention also relates to methods and medicaments for the treatment, control, or prevention of Type 2 diabetes by administering the compounds and pharmaceutical compositions of the present invention. The present invention also relates to methods and medicaments for the treatment, control, or prevention of Type 2 diabetes by administering the compounds of the present invention in combination with a therapeutically effective amount of another agent known to be useful to treat the condition. The present invention also relates to methods and medicaments for the treatment, control, or prevention of diabetes related disorders by administering the compounds and pharmaceutical compositions of the present invention alone, or in combination. The present invention also relates to methods and medicaments for the treatment and prevention of diabetes in pre-diabetic subject by administering the compounds and pharmaceutical compositions of the present invention alone, or in combination.

The present invention also relates to methods and medicaments for the treatment, control, or prevention of obesity by administering the compounds and pharmaceutical compositions of the present invention. The present invention also relates to methods and medicaments for the treatment, control, or prevention of obesity by administering the compounds of the present invention in combination with a therapeutically effective amount of another agent known to be useful to treat the condition. The present invention also relates to methods and medicaments for the treatment, control, or prevention of obesity related disorders by administering the compounds and pharmaceutical compositions of the present invention alone, or in combination. The present invention also relates to methods and medicaments for the treatment and prevention of obesity in overweight subject by administering the compounds and pharmaceutical compositions of the present invention alone, or in combination. The compounds are also useful for the treatment of obesity related disorders, or eating disorders associated with excessive food intake, and complications associated therewith, including left ventricular hypertrophy, as well as treating or preventing obesity in other mammalian species, including canines and felines.

The present invention also relates to methods and medicaments for the treatment, control, or prevention of hyperglycemia by administering the compounds and pharmaceutical compositions of the present invention. The present invention also relates to methods and medicaments for the treatment, control, or prevention of hyperglycemia by administering the compounds of the present invention in combination with a therapeutically effective amount of another agent known to be useful to treat the condition.

The present invention also relates to methods and medicaments for the treatment, control, or prevention of insulin resistance by administering the compounds and pharmaceutical compositions of the present invention. The present invention also relates to methods and medicaments for the treatment, control, or prevention of insulin resistance by administering the compounds of the present invention in combination with a therapeutically effective amount of another agent known to be useful to treat the condition.

The present invention also relates to methods and medicaments for the treatment, control, or prevention of lipid disorders by administering the compounds and pharmaceutical compositions of the present invention. The present invention also relates to methods and medicaments for the treatment, control, or prevention of lipid disorders by administering the compounds of the present invention in combination with a therapeutically effective amount of another agent known to be useful to treat the condition. The present invention also relates to methods and medicaments for the treatment, control, or prevention of dyslipidemia related disorders and lipid disorder-related disorders by administering the compounds and pharmaceutical compositions of the present invention alone, or in combination.

The present invention also relates to methods and medicaments for the treatment, control, or prevention of atherosclerosis by administering the compounds and pharmaceutical compositions of the present invention. The present invention also relates to methods and medicaments for the treatment, control, or prevention of atherosclerosis by administering the compounds of the present invention in combination with a therapeutically effective amount of another agent known to be useful to treat the condition. The present invention also relates to methods and medicaments for the treatment, control, or prevention of atherosclerosis related disorders by administering the compounds and pharmaceutical compositions of the present invention alone, or in combination.

The present invention also relates to methods and medicaments for the treatment, control, or prevention of hypertension by administering the compounds and pharmaceutical compositions of the present invention. The present invention also relates to methods and medicaments for the treatment, control, or prevention of hypertension by administering the compounds of the present invention in combination with a therapeutically effective amount of another agent known to be useful to treat the condition. The present invention also relates to methods and medicaments for the treatment, control, or prevention of hypertension related disorders by administering the compounds and pharmaceutical compositions of the present invention alone, or in combination. The present invention also relates to methods and medicaments for the treatment and prevention of hypertension in pre-hypertensive subject by administering the compounds and pharmaceutical compositions of the present invention alone, or in combination.

The present invention also relates to methods and medicaments for the treatment, control, or prevention of Metabolic Syndrome by administering the compounds and pharmaceutical compositions of the present invention. The present invention also relates to methods and medicaments for treating Metabolic Syndrome by administering the compounds of the present invention in combination with a therapeutically effective amount of another agent known to be useful to treat the condition.

The compounds of the present invention wherein Y is a cycloalkyl or cycloheteroalkyl ring have been found to have the unexpected benefit of an increased ratio of muscle target engagement relative to liver target engagement in mice following oral dosing compared to compounds with similar $R^1$-$R^5$ substituents wherein Y is an aromatic ring. In this instance, target engagement is measured by the phosphorylated ACC/total ACC ratio in muscle tissue and liver tissue in db/+ mice. An increased ratio of muscle target engagement relative to liver tissue target engagement means an increase in muscle tissue phosphorylated ACC/total ACC for the same level of liver tissue phosphorylated ACC/total ACC. This increased ratio of muscle tissue phosphorylated ACC/total ACC may lead to an increase in fatty acid oxidation and a decrease in intracellular lipid levels in muscle.

It is anticipated that an AMPK activator with increased muscle target engagement will have a greater opportunity to induce metabolic changes that are anticipated to contribute to increased insulin sensitivity in muscle, such as decreasing intracellular lipids and/or increasing glucose uptake. Elevated intracellular lipids are considered one of the major causes of insulin resistance in skeletal muscle and defects in fatty acid oxidation have been considered the primary causal factors in the development of muscle insulin resistance (Petersen, K. F., et. al. (2004), N. Engl. J. Med. 350, 664-671). Reduction in elevated intracellular lipids is regarded as a potentially key requirement for achieving clinically significant improvements in insulin sensitization. AMPK activation promotes fatty acid oxidation via ACC phosphorylation to decrease intramyocyte lipids, such as triglycerides (Ruderman, N. B., et. al. (2003), Endocrinology 144, 5166-5171).

Further, compounds of the present invention wherein Y is a cycloalkyl or cycloheteroalkyl ring have been found to unexpectedly exhibit a longer half life in rat studies compared to compounds with similar $R^1$-$R^5$ substituents wherein Y is an aromatic ring. This longer half life leads to longer muscle target engagement, which may result in an increase in fatty acid oxidation and a decrease in intracellular lipid levels. Finally, the compounds of the present invention also have the unexpected benefit of reduced induction of CYP-1A and consequently a decreased likelihood of drug-drug interactions with CYP-1A substrates relative to compounds with similar $R^1$-$R^5$ substituents wherein Y is an aromatic ring.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention are useful for treating both Type 1 and Type 2 diabetes. The term "diabetes associated with obesity" refers to diabetes caused by obesity or resulting from obesity. The compositions are especially effective for treating Type 2 diabetes. The compositions of the present invention are also useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/di; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of ≥140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or More non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (≥140 mmHg/≥90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMJ), which is calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. An overweight subject is a subject at risk of obesity. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a EMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus-type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The compounds of formula I are also useful for treating or preventing obesity and obesity-related disorders in cats and dogs. As such, the term "mammal" includes companion animals such as cats and dogs.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

Left ventricular hypertrohpy (LVH) is identified based on left ventricular mass index (LVMI) and relative wall thickness (RWT). Left ventricular mass index is defined as left ventricular mass in grams divided by body surface area in meters$^2$. Relative wall thickness is defined as 2×posterior wall thickness/left ventricular end diastolic diameter. Normal LVMI values are typically 85 and normal RWT approximately 0.36. A male subject with LVH has a LVMI greater than 131 g/m$^2$; a female subject with LVH has a LVMI greater than 100 g/m$^2$. A subject with an elevated LVMI value is a male subject with a LVMI between 85 g/m$^2$ and 131 g/m$^2$, or a female subject with a LVMI between 85 g/m$^2$ and 100 g/m$^2$.

Treatment of cardiac hypertrophy, or left ventricular hypertrophy, refers to the administration of the combinations of the present invention to a subject with cardiac hypertrophy or left ventricular hypertrophy. Prevention of cardiac hypertrophy, or left ventricular hypertrophy, refers to the administration of the combinations of the present invention to decrease or maintain the LVMI in a subject with an elevated LVMI value or to prevent the increase of LVMI in a subject with a normal LVMI value.

One outcome of treatment of cardiac hypertrophy or left ventricular hypertrophy may be a decrease in ventricular mass. Another outcome of treatment of cardiac hypertrophy or left ventricular hypertrophy may be a decrease in the rate of increase of ventricular mass. Another outcome of treatment of cardiac hypertrophy or left ventricular hypertrophy may be a decrease in ventricular wall thickness. Another outcome of treatment of cardiac hypertrophy of left ventricular hypertrophy may be the decrease in the rate of increase in ventricular wall thickness.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or a companion animal such as a dog or cat, with an effective dosage of a compound of the present invention. For example, oral, rectal, topical, parenteral, ocular, pulmonary, and nasal routes of administration, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |

| Injectable Suspension (I.M.) | mg/mL |
|---|---|
| Benzyl alcohol | 9.0 |
| Benzalkonium chloride | 1.0 |

Water for injection to a total volume of 1 mL

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases, disorders or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: other anti-diabetic agents, anti-dylipidemic agents, and anti-hypertensive agents, anti-obesity agents, and anorectic agents, which may be administered separately or in the same pharmaceutical compositions.

The present invention also provides a method for the treatment or prevention of an AMPK-activated protein kinase (AMPK) mediated disease, which method comprises administration to a patient in need of such treatment or at risk of developing an AMPK mediated disease of an amount of an AMPK activator and an amount of one or more active ingredients, such that together they give effective relief.

In a further aspect of the present invention, there is provided a pharmaceutical composition comprising an AMPK activator and one or more active ingredients, together with at least one pharmaceutically acceptable carrier or excipient.

Thus, according to a further aspect of the present invention there is provided the use of an AMPK activator and one or more active ingredients for the manufacture of a medicament for the treatment or prevention of an AMPK mediated disease. In a further or alternative aspect of the present invention, there is therefore provided a product comprising an AMPK activator and one or more active ingredients as a combined preparation for simultaneous, separate or sequential use in the treatment or prevention of an AMPK mediated disease. Such a combined preparation may be, for example, in the form of a twin pack.

It will be appreciated that for the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief.

The present invention also provides a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

Suitable pharmaceutical agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000685, and 03/027112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and Al-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, THO318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/G1-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00123417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promoters such as those disclosed in WO 03/007990; (21) fixed combinations of PPAR γ agonists and metfounin such as AVANDAMET; (22) PPAR pan agonists such as GSK 677954; (23) GPR40 (G-protein coupled receptor 40 also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 213 antagonists such as ATL-618, ATl-802, E3080, and the like; (26) carnitine palmitoyl transferase inhibitors such as ST 1327, and ST 1326, and the like; (27) Fructose 1,6-bisphosphohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; and 40) insulin secretagogues;

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VA12 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche), ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPARδ agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/ HMR1453 (Sanofi-Aventis, PHA384640E (Pfizer), 58921 (Shionogi) AZD7806 (AstrZeneca), AK105 (Asch Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline; and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CBI (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081,122, 5,112,820, 5,292,736, 5,532,237, 5,624,941, 6,028,084, and 6,509,367;

and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl) carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TP1-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, 52367 (Shionogi), E-6999 (Esteve), GW-569180A, GW-594884A (GlaxoSmithkline), GW-587081X, GW-548118X; FR 235,208; FR226928, FR 240662, FR252384; 1229U91, GI-264879A, CGP71683A, C-75 (Fasgen) LY-377897, LY366377, PD-160170, SR-120562A, SR-120819A, S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al, J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NB172432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) β3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. Nos. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2)inhibitors; (31) FAS (fatty acid synthase) inhibitors, such as Cerulenin and C75; (32) PDE (phosphodiesterase) inhibitors, such as theophylline, pentoxifylline, zaprinast, sildenafil; aminone, milrinone, cilostamide, rolipram, and cilomilast, as well as those described in WO 03/037432, WO 03/037899; (33) thyroid hormone β agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 11β HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune)Triton WR1339, RHC80267, lipstatin, teasaponin, and diethylumbelliferyl phosphate, FL-386, WAY-121898, Bay-N-3176, valilactone, esteracin, ebelactone A, ebelactone 13, and RHC 80267, and those disclosed in WO 01177094, WO 04/111004, and U.S. Pat. Nos. 4,598,089, 4,452,813, 5,512, 565, 5,391,571, 5,602,151, 4,405,644, 4,189,438, and 4,242, 453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Technologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) *Hoodia* and *trichocaulon* extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof.

Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl) {3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-Oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl) {3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof.

Specific NPY5 antagonists of use in combination with a compound of the present invention include: 3-oxo-N-(5-phenyl-2-pyrazinyl)-spiro[isobenzofuran-1(3H), 4'-piperidine]-1'-carboxamide, 3-oxo-N-(7-trifluoromethylpyrido[3,2-b]pyridin-2-yl)spiro-[isobenzofuran-1(3H), 4'-piperidine]-1'-carboxamide, N-[5-(3-fluorophenyl)-2-pyrimidinyl]-3-oxospiro-[isobenzofuran-1(3H), 4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H), 1'-cyclohexane]-4'-carboxamide, trans-N-[5-(3-fluorophenyl)-2-pyrimidinyl]-3-oxospiro[5-azaisobenzofuran-1(3H), 1'-cyclohexane]-4'-carboxamide, trans-N-[5-(2-fluorophenyl)-2-pyrimidinyl]-3-oxospiro[5-azaisobenzofuran-1(3H), 1'-cyclohexane]-4'-carboxamide, trans-N-[1-(3,5-difluorophenyl)-4-imidazolyl]-3-oxospiro[7-azaisobenzofuran-1(3H), 1'-cyclohexane]-4'-carboxamide, trans-3-oxo-N-(1-phenyl-4-pyrazolyl)spiro[4-azaisobenzofuran-1(3H), 1'-cyclohexane]-4'-carboxamide, trans-N-[1-(2-fluorophenyl)-3-pyrazolyl]-3-oxospiro[6-azaisobenzofuran-1(3H), 1'-cyclohexane]-4'-carboxamide, trans-3-oxo-N-(1-phenyl-3-pyrazolyl)spiro[6-azaisobenzofuran-1(3H), 1'-cyclohexane]-4'-carboxamide, trans-3-oxo-N-(2-phenyl-1,2,3-triazol-4-yl)spiro[6-azaisobenzofuran-1(3H), 1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl)spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy- 8-ethylquinolin-2-yl)carbonyl]-6-(1H-tetrazol-5-yl)spiro[chroman-2,4'-piperidin]-4-one; and pharmaceutically acceptable salts and esters thereof.

Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof.

Specific H3 (histamine H3) antagonists/inverse agonists of use in combination with a compound of the present invention include: those described in WO05/077905, including: 3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4(3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1 cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4(3H)-one, 3-{4-[(1-cyclobutylpiperidin-4-yl)oxy]phenyl}-6-fluoro-2-methylpyrido[3,4-d]pyrimidin-4(3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4(3H)-one, 2,5-dimethyl-3-{4-[3-(1-pyrrolidinyl)propoxy]phenyl}-4(3H)-quinazolinane, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{([2-cyclopropoxy-5-(trifluoromethoxy)-phenyl]methyl}-2-phenylpiperidin-3-amine; 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

PREPARATION OF COMPOUNDS OF THE INVENTION

The compounds of formula I of the present invention can be prepared according to the procedures of the following Schemes, Intermediates and Examples, using appropriate materials and are further exemplified by the following specific examples. Moreover, by utilizing the procedures described herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogen carbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. All temperatures are degrees Celsius unless otherwise noted. Mass spectra (MS) were measured by electrospray ion-mass spectroscopy (ESMS).

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

General Methods Reactions sensitive to moisture or air were performed under nitrogen using anhydrous solvents and reagents. The progress of reactions was determined by either analytical thin layer chromatography (TLC) performed with E. Merck precoated TLC plates, silica gel 60E-254, layer thickness 0.25 mm or liquid chromatography-mass spectrum (LC-MS). Analytical HPLC/MS—Standard Method: Mass analysis was performed on a Waters Micromass® ZQ™ with electrospray ionization in positive ion detection mode. High performance liquid chromatography (HPLC) was conducted on an Agilent 1100 series HPLC on Waters C18 XTerra 3.5 µm 3.0×50 mm column with gradient 10:90-100 v/v $CH_3CN$/$H_2O$+v 0.05% TFA over 3.75 min then hold at 100 $CH_3CN$+v 0.05% TFA for 1.75 min; flow rate 1.0 mL/min, UV wavelength 254 nm (all HPLC/MS data was generated with this method unless indicated otherwise). Concentration of solutions was carried out on a rotary evaporator under reduced pressure. Flash chromatography was performed using a Biotage Isolera™, Horizon or SP1 Flash Chromatography apparatus (Dyax Corp.) on silica gel (32-63 µM particle size, KP-Sil 60 Å packing material type) in pre-packed cartridges or using an ISCO CombiFlash™ Sq 16x or CombiFlash®-Companion™ apparatus on silica gel (32-63 µM, 60 Å) in pre-packed cartridges. Microwave reactions were carried out on a Biotage Initiator™ 2.0 or CEM Discover™ system.

Abbreviations Used in the Description of the Preparation of the Compounds of the Present Invention: AcCN and ACN are acetonitrile; $Ac_2O$ is acetic anhydride; AcOH is acetic acid; aq is aqueous; Doc and BOC is tert-butyloxycarbonyl; $BOC_2O$ is di-tert-butyl dicarbonate; Bn is benzyl; BnOH is benzyl alcohol; BuLi is butyl lithium; brine is saturated aqueous sodium chloride solution; CDI is 1,1'-carbonyldiimidazole; Celite™ is diatomaceous earth; $CO_2$ is carbon dioxide; CO is carbon monoxide; D is deuterium; DCM or $CH_2Cl_2$ is dichloromethane; dppf is 1,1"-bis(diphenylphosphino)ferrocene; DBU is 1,8-diazabicyclo[5.4.0]undec-7-ene; DIPEA and DIEA is N,N-diisopropylethylamine; DMAP is 4-N,N-dimethylaminopyridine; DME is 1,2-dimethoxyethane; DMF is N,N-dimethylformamide; DMA is N,N-dimethylacetamide; DMSO is dimethyl sulfoxide; EDC is 1-(dimethylaminopropyl)-3-ethylcarbodiimide hydrochloride; EtOAc is ethyl acetate; Et (et) is ethyl; EA and EtOAc is ethyl acetate; equiv is equivalent(s); ESI is electrospray ionization; $Et_3N$ is triethylamine; $Et_3SiH$ is triethylsilane; EtOH is ethanol; $Et_2O$ or ether is diethyl ether; g is grams; h or hr is hour; HATU is O-(7-azabenzotriazol-1-yl)-N,N,N',N'-tetramethyluronium hexafluorophosphate; HCl is hydrochloric acid; HOST or HOBt is 1-hydroxybenzotriazole; HPLC is high-performance liquid chromatography; in vacuo is rotary evaporation under diminished pressure; i-Pr is isopropyl; i-Pr is isopropyl; i-PrOH or IPA is isopropyl alcohol; KOTMS is potassium trimethyl silanolate; LC is liquid chromatography; LC/MS is liquid chromatography/mass spectroscopy; L is liter(s); m-CPBA is 3-chloroperbenzoic acid; mg is milligrams; ml and mL is milliliter; M is molar; mmol is millimole(s); Me is methyl; MeCN is acetonitrile; MeOH is methanol; min is minute(s); ms or MS is mass spectrum; MTBE is methyl-tert-butyl ether; µg is microgram(s); µL is microliter(s); $NaBH_4$ is sodium borohydride; NaHMDS is sodium hexamethyldisilazide; NaOEt is sodium ethoxide; NaOMe is sodium methoxide; NaOAc is sodium acetate; NIS is N-iodosuccinimide; NMR is nuclear magnetic resonance spectroscopy; Pd(PPh$_3$)$_4$ is tetrakis triphenyl phosphine palladium; PE is petroleum ether; Pearlman's Catalyst is Pd(OH)$_2$ (20 wt % Pd (dry basis) on carbon, wet), Ph is phenyl; RP or rp is reverse phase; R$_f$ is Rf factor; R$_t$ is retention time; RT and rt is room temperature; sat, safd., and sat is saturated; SEM is 2-(trimethylsilyl)ethoxymethyl; SEMCl is 2-(trimethylsilyl)ethoxymethyl chloride; SF is supercritical fluid; SFC is supercritical fluid chromatography; TBAF is tetrabutyl ammonium fluoride; TEA is triethylamine; TFA is trifluoroacetic acid; TFAA is trifluoroacetic anhydride; THF is tetrahydrofuran; TLC is thin layer chromatography; TMS is trimethylsilyl; Tos is 4-toluenesulfonyl; TosCl is 4-toluenesulfonyl chloride; OTs is 4-toluenesulfonate; TsOH is p-toluenesulfonic acid; v is volume; v % and v/v are volume percent; and wt % is weight percent.

The following reaction schemes illustrate methods which may be employed for the synthesis of the intermediates and the compounds of structural formula I described in this invention. All substituents are as defined above unless indicated otherwise. Several strategies based upon synthetic transformations known in the literature of organic synthesis may be employed for the preparation of the title compounds of general formula I.

In the General Scheme, the Intermediate is reacted with a boronic acid, boronate ester or stannane (R$^1$-M) in the presence of palladium tetrakistriphenylphosphine to afford, after protection of the benzimidazole core, compound A. Subsequent reaction of compound A with a hydroxycycloalkanoate, and benzimidazole deprotection affords the 2-substituted benzimidazole B.

GENERAL SCHEME

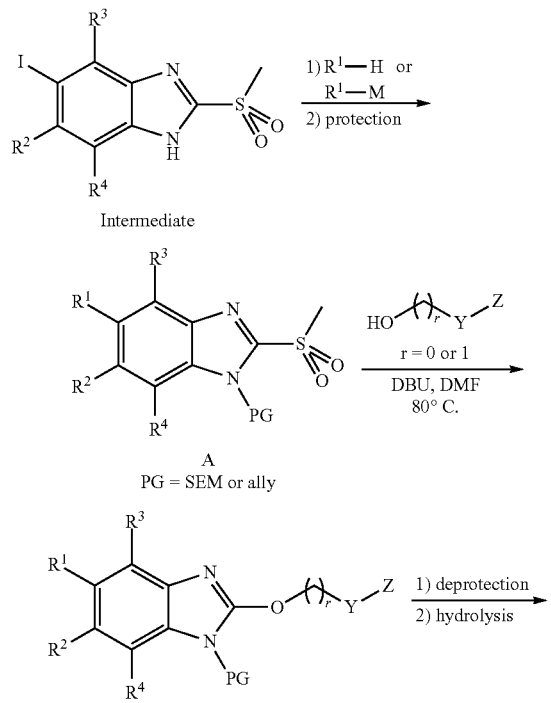

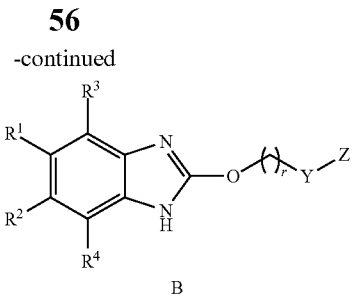

In Scheme 1, Intermediate 1 is reacted with a boronic acid, boronate ester or stannane (R$^1$-M) in the presence of palladium tetrakistriphenylphosphine to afford, after protection of the benzimidazole core, compound 1A. Subsequent reaction of compound 1A with a hydroxycycloalkanoate, benzimidazole deprotection, and hydrolysis of Z when Z is an ester (R is C$_{1-6}$alkyl), affords the 2-substituted benzimidazole 1B.

SCHEME 1

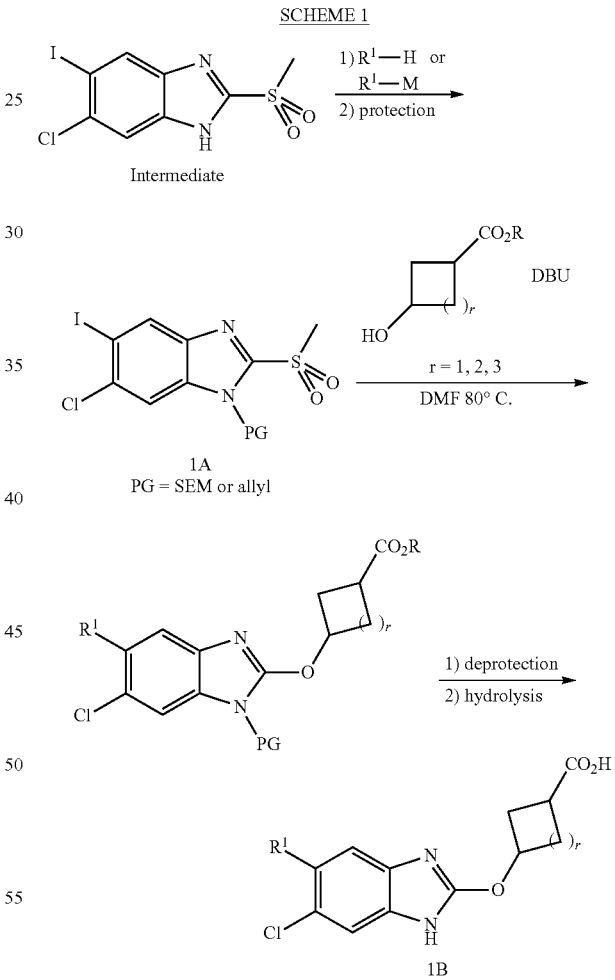

In Scheme 2, Intermediate 5 is reacted with a hydroxycycloalkanoate in the presence of DBU to yield compound 2A. Subsequent reaction of compound 2A with a boronic acid, boronate ester or stannane (R$^1$-M) in the presence of palladium tetrakistriphenylphosphine followed by benzimidazole deprotection, and hydrolysis of Z when Z is an ester (R is C$_{1-6}$alkyl), affords the 2-substituted benzimidazole 2B.

SCHEME 2

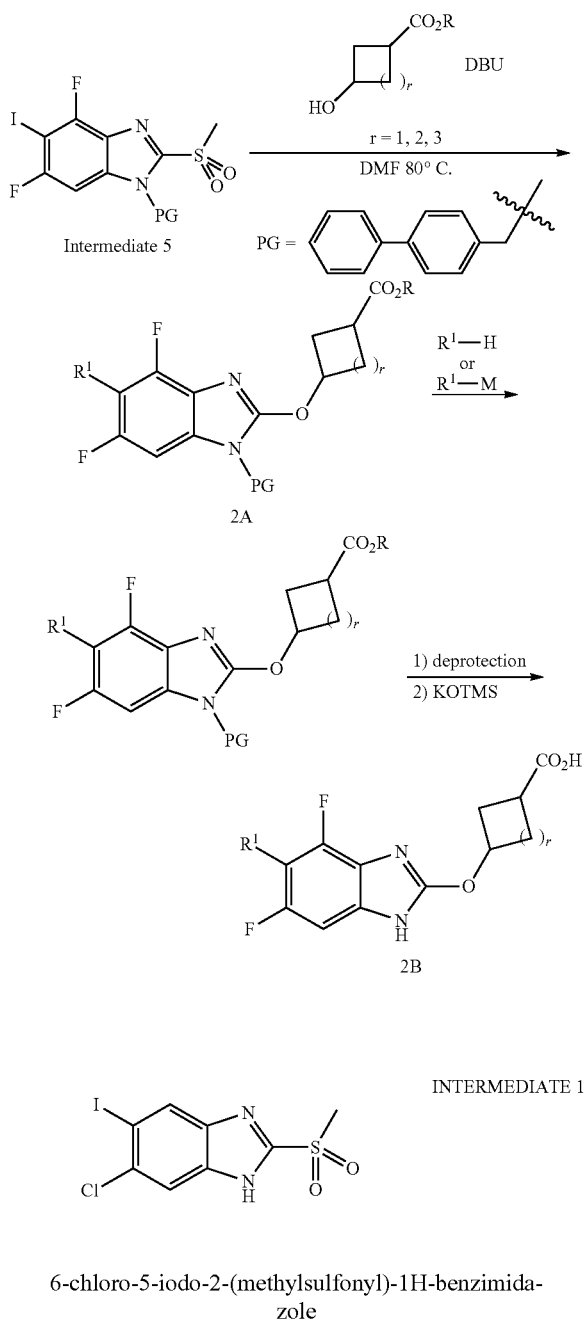

were added and heating was continued for 45 h. The reaction mixture was cooled, filtered and concentrated. The resulting residue was re-dissolved in ethyl acetate and washed with sodium bicarbonate solution. The organic phase was concentrated to afford the desired product as a gray solid, which was used in the next step without further purification.

Step C 5-chloro-6-iodo-1,3-dihydro-2H-benzimidazole-2-thione. KOH (15.7 g, 238 mmol) in water (50 mL), followed by carbon disulfide (14.4 mL, 238 mmol), was added to a solution of 4-chloro-5-iodobenzene-1,2-diamine (50 g, 198 mmol) in EtOH (300 mL). The mixture was heated at reflux for 3 h, cooled and filtered. To the filtrate was added water (300 mL) and then AcOH (25 mL) in water (50 mL). The resulting precipitate was collected, washed with water and a small amount of EtOH, and then dried to afford the desired product as a brown powder, which was used in the next step without further purification.

Step D 6-chloro-5-iodo-2-(methylthio)-1H-benzimidazole. $K_2CO_3$ (0.22 g, 1.61 mmol), followed by iodomethane (0.1 mL, 1.61 mmol), was added to a solution of 5-chloro-6-iodo-1,3-dihydro-2H-benzimidazole-2-thione (1 g, 3.22 mmol) in acetone (20 mL) at 0° C. The reaction was stirred at rt for 1 h. Additional $K_2CO_3$ (1.61 mmol) and iodomethane (1.61 mmol) were added. The reaction was stirred at rt overnight, then the volatiles were removed and the residue was partitioned between EtOAc and water. Concentration of the EtOAc layer afforded the desired product as a white foam, which was used in the next step without further purification.

Step E 6-chloro-5-iodo-2-(methylsulfonyl)-1H-benzimidazole. m-Chloroperbenzoic acid (1.4 g, 6.16 mmol) was added to a suspension of 6-chloro-5-iodo-2-(methylthio)-1H-benzimidazole (1.0 g, 3.08 mmol) in DCM (50 mL). The reaction stirred at rt for 10 min then washed with 10% aqueous $NaHCO_3$. The organic phase was separated, and concentrated. The resulting residue was triturated with MeOH (3 mL), filtered and concentrated to afford the title compound as white powder. LC-MS: calculated for $C_8H_6ClIN_2O_2S$ 356.57, observed m/e 357.30 $(M+H)^+$ ($R_t$ 1.21/2 min). NMR ($CD_3OD$): 8.3 (1H,s), 7.9 (1H,s), 3.3 (3H,s).

INTERMEDIATE 1

6-chloro-5-iodo-2-(methylsulfonyl)-1H-benzimidazole

Step A 5-chloro-4-iodo-2-nitroaniline. To a solution of 5-chloro-2-nitroaniline (25 g, 145 mmol) in AcOH (250 mL) was added N-iodosuccinimide (32.6 g 145 mmol). The mixture was stirred overnight at 50° C., cooled down to rt and filtered. The solid residue was washed with AcOH, water, saturated aqueous $NaHCO_3$ and water, and then dried to afford the desired product as a brown solid, which was used in the next step without further purification.

Step B 4-chloro-5-iodobenzene-1,2-diamine. To a suspension of 5-chloro-4-iodo-2-nitroaniline (36.5 g, 122 mmol) in EtOH (800 mL) and water (150 mL) was added iron powder (38 g, 673 mmol) and $NH_4Cl$ (16 g, 306 mmol). The mixture was heated under nitrogen at 50° C. overnight. Additional iron powder (38 g, 673 mmol) and $NH_4Cl$ (16 g, 306 mmol)

INTERMEDIATE 2

6-chloro-5-iodo-2-(methylsulfonyl)-1-{[2-(trimethylsilyl)ethoxy]methyl}-1H-benzimidazole $Et_3N$ (20.95 mL, 150 mmol) and 2-(trimethylsilyl)ethoxy methyl chloride (17.29 mL, 98 mmol) were added to a solution of 6-chloro-5-iodo-2-(methylsulfonyl)-1H-benzimidazole (Intermediate 1, 26.8 g, 75 mmol) in THF (200 mL). The reaction was stirred at rt for 1 h, then the volatiles were removed and the resulting residue partitioned between EtOAc and water. The organic phase was separated, washed with 2N aqueous HCl and brine, dried ($MgSO_4$) and concentrated to afford the title compound as a white solid. LC-MS: calculated for $C_{14}H_{20}ClIN_2O_3SSi$ 485.97, observed m/e 428.83 $(M+H)^+$ ($R_t$ 2.30 min).

INTERMEDIATE 3

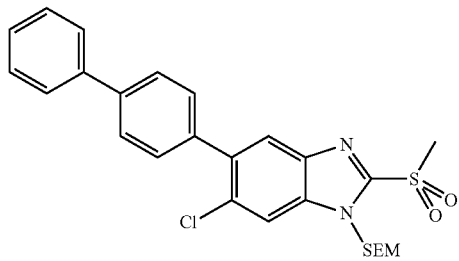

5-(biphenyl-4-yl)-6-chloro-2-(methylsulfonyl)-1-{[2-(trimethylsilyl)ethoxy]methyl}-1H-benzimidazole Step A 5-biphenyl-4-yl-6-chloro-2-(methylsulfonyl)-1H-benzimidazole. A solution of potassium phosphate, tribasic (2 M solution in water; 21 mL, 42 mmol), Pd(PPh$_3$)$_4$ (0.324 g, 0.280 mmol), 4-biphenylboronic acid (3.94 g, 19.9 mmol) and 6-chloro-5-iodo-2-(methylsulfonyl)-1H-benzimidazole (Intermediate 1, 5 g, 14 mmol) in dioxane (70 mL) was heated at 100° C. for 5 h. The aqueous phase was removed and the organic phase was concentrated, diluted with EtOAc and DCM, and filtered. The filtrate was concentrated to afford the desired product as a white solid, which was used in the next step without further purification.

Step B 5-biphenyl-4-yl-6-chloro-2-(methylsulfonyl)-1-{[2-(trimethylsilyl)ethoxy]methyl}-1H-benzimidazole. To a solution of 5-biphenyl-4-yl-6-chloro-2-(methylsulfonyl)-1H-benzimidazole (5.37 g, 14.0 mmol) in THF (70 mL) was added DIPEA (3.67 mL, 21.0 mmol) followed by SEMCl (3.7 mL, 21.0 mmol). The reaction was maintained for 5 h at ambient temperature. Then the reaction mixture was diluted with EtOAc and washed with saturated aqueous NaHCO$_3$, followed by brine. The organic phase was dried over Na$_2$SO$_4$, filtered, and concentrated. Chromatography of the resulting residue over silica eluting with 5-25% EtOAc/hexanes afforded the desired product as a white solid. LC-MS: calculated for C$_{14}$H$_{20}$ClN$_2$O$_3$SSi 485.97, observed m/e 428.83 (M+H)$^+$ (R$_t$ 2.30 min).

INTERMEDIATE 4

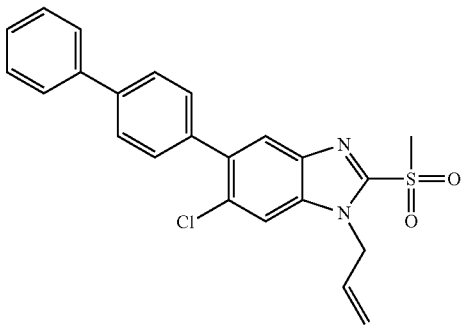

5-(biphenyl-4-yl)-6-chloro-2-(methylsulfonyl)-1-(prop-2-en-1-yl)-1H-benzimidazole To a solution of 5-biphenyl-4-yl-6-chloro-2-(methylsulfonyl)-1H-benzimidazole (1.72 g, 4.49 mmol) in THF (30 ml) and 1M potassium carbonate (3.10 g, 22.46 mmol) was added allyl bromide (0.6 ml, 6.89 mmol). The reaction mixture was heated to 60° C. for 20 h. Then the volatiles were removed in vacuo and the resulting residue was partitioned between EtOAc and water. The aqueous phase was separated and extracted with EtOAc. The combined organic layers were washed with brine, dried (MgSO$_4$), filtered, and concentrated. Chromatography of the resulting residue over silica eluting with 20-40% EtOAc/hexanes afforded the desired product. LC-MS: calculated for C$_{23}$H$_{19}$ClN$_2$O$_2$S 422.09, observed m/e: 422.94 (M+H)$^+$ (R$_t$ 2.52/4 min).

INTERMEDIATE 5

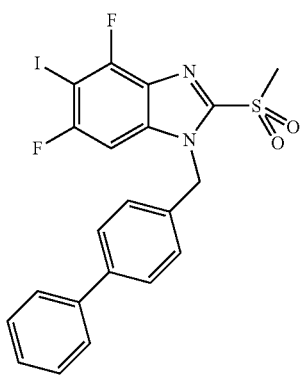

1-(biphenyl-4-ylmethyl)-4,6-difluoro-5-iodo-2-(methylsulfonyl)-1H-benzimidazole

Step A N-(biphenyl-4-ylmethyl)-3,5-difluoro-2-nitroaniline. Potassium carbonate (10.9 g, 79 mmol) was added to a solution of 1,3,5-trifluoro-2-nitrobenzene and 1-biphenyl-4-ylmethanamine in THF (200 mL). The mixture was stirred at rt for 15 h. Then the reaction mixture was filtered and concentrated to afford the desired product as a deep orange solid.

Step B N-(biphenyl-4-ylmethyl)-3,5-difluoro-4-iodo-2-nitroaniline. NIS (7.9 g, 35.1 mmol) was added to a solution of N-(biphenyl-4-ylmethyl)-3,5-difluoro-2-nitroaniline (10.86 g, 31.9 mmol) in AcOH (150 mL). After heating at 70° C. for 2 h, the reaction mixture was concentrated and partitioned between EtOAc and saturated aqueous NaHCO$_3$. The organic phase was separated, washed with brine, dried (Na$_2$SO$_3$) and concentrated. The resulting solid was recrystallized from DCM/hexanes afforded the desired product as a red solid.

Step C N'-(biphenyl-4-ylmethyl)-3,5-difluoro-4-iodobenzene-1,2-diamine. A 20% solution of AcOH (6.7 mL, 117 mmol) in water was added to a suspension of iron (10.89 g, 195 mmol) in a solution of N-(biphenyl-4-ylmethyl)-3,5-difluoro-4-iodo-2-nitroaniline (12.12 g, 26 mmol) in EtOH (70 mL). After heating the reaction at 76° C. for 2 h, the volatiles were removed. The resulting residue was extracted with EtOAc. The combined organic extracts were filtered through Celite™, washed with aqueous ammonium hydroxide and brine, dried (Na$_2$SO$_4$) and concentrated. Chromatography of the resulting residue over silica eluting with 10-50% EtOAc/hexanes afforded the desired product as a yellow solid.

Step D 1-(biphenyl-4-ylmethyl)-4,6-difluoro-5-iodo-1,3-dihydro-2H-benzimidazole-2-thione. 1,1'-thiocarbonyldiimidazole (4.75 g, 26.6 mmol) was added to a solution of N'-(biphenyl-4-ylmethyl)-3,5-difluoro-4-iodobenzene-1,2-diamine (9.68 g, 22.19 mmol) in DMSO (30 mL). After stirring at rt for 16 h, the reaction mixture was diluted with DCM and the precipitated solid was collected to afford the desired product.

Step E 1-(biphenyl-4-ylmethyl)-4,6-difluoro-5-iodo-2-(methylthio)-1H-benzimidazole. Iodomethane (2 M in methyl-tert-butyl ether, 22.87 mL, 45.7 mmol) was added to a solution of cesium carbonate (14.9 g, 45.7 mmol) and 1-(biphenyl-4-ylmethyl)-4,6-difluoro-5-iodo-1,3-dihydro-2H-benzimidazole-2-thione (10.94 g, 22.87 mmol) in THF (100 mL). After stirring the reaction at rt overnight, the volatiles were removed. Chromatography of the resulting residue over silica eluting with 15-60% EtOAc/hexanes afforded the desired product as a beige solid.

Step F 1-(biphenyl-4-ylmethyl)-4,6-difluoro-5-ioda-2-(methylsulfonyl)-1H-benzimidazole. m-CPBA (10 g, 44.6 mmol) in DCM (200 mL) was added to 1-(biphenyl-4-ylmethyl)-4,6-difluoro-5-iodo-2-(metlaylthio)-1H-benzimidazole (10.98 g, 22.3 mmol). The reaction mixture was stirred at rt for 16 h. An additional portion of m-CPBA (3 g) was added and the reaction was stirred for 1 h. Then the volatiles were removed, and the resulting residue was partitioned between EtOAc and saturated aqueous NaHCO$_3$. The organic phase was separated, washed with brine, dried (Na$_2$SO$_4$) and concentrated. Chromatography of the resulting residue over silica eluting with 15-30% EtOAc/hexanes afforded the title compound as a white solid. LC-MS: calculated for C$_{21}$H$_{15}$F$_2$IN$_2$O$_2$S 523.99, observed m/e 525.00 (M+H)$^+$ (R$_t$ 2.15 min).

INTERMEDIATE 6

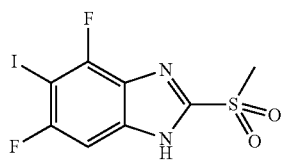

4,6-difluoro-5-iodo-2-(methylsulfonyl)-1H-benzimidazole. The title compound was prepared according to the procedures described for Intermediate 5, Steps B-F by substituting 3,5-difluoro-2-nitroaniline for N-(biphenyl-4-ylmethyl)-3,5-difluoro-2-nitroaniline in Step B. LCMS: calculated for C$_8$H$_5$F$_2$IN$_2$O$_2$S 358.10, observed m/e 358.9 (M+H)$^+$ (Rt 1.31/4 min).

INTERMEDIATE 7

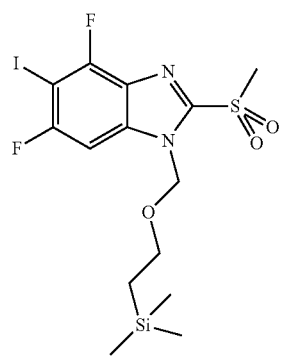

4,6-difluoro-5-iodo-2-(methylsulfonyl)-1-{[2-(trimethylsilyl)ethoxy]methyl}-1H-benzimidazole 4,6-difluoro-5-iodo-2-(methylsulfonyl)-1H-benzimidazole (5 g, 13.96 mmol) was dissolved in THF (50 mL), and then triethylamine (4 mL, 28.7 mmol) was added. The reaction mixture was maintained for 2 h at ambient temperature. The crude reaction was concentrated and re-dissolved with EtOAc and H$_2$O. The organic layer was separated, and washed with 1 N HCl and brine. The organic layer was then dried over Na$_2$SO$_4$, filtered, and concentrated. Purification of the resulting crude product by flash chromatography (5-15%, then 15-25% EtOAc/hexanes) afforded the title compound. LCMS: calculated for C$_{14}$H$_{19}$F$_2$IN$_2$O$_3$SSi 488.36, observed ink 510.9 (M+Na)$^+$ (Rt 2.31/4 min).

INTERMEDIATE 8

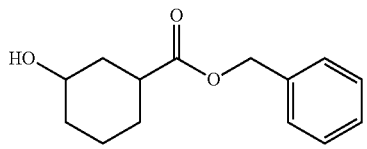

Benzyl 3-hydroxycyclohexanecarboxylate

Step A: Benzyl 3-oxocyclohexanecarboxylate. To a solution of 3-oxocyclohexane carboxylic acid (1.5 g, 10.6 mmol) in CH$_2$Cl$_2$ (35 mL) were added DMAP (0.129 g, 1.06 mmol), EDC (4.05 g, 21.1 mmol), and BnOH (1.2 mL, 11.6 mmol). The reaction was maintained at ambient temperature for 1 h. The reaction was further diluted with CH$_2$Cl$_2$, and then washed with saturated aqueous NaHCO$_3$, followed by brine. The organic layer was separated, dried with MgSO$_4$, filtered, and concentrated. The resulting crude product was used in the next step without further purification. LCMS: calculated for C$_{14}$H$_{16}$O$_3$ 232.28, observed m/e 233.1 (M+H)$^+$ 255.0 (M+Na) (Rt 1.74/4 min).

Step B: Benzyl 3-hydroxycyclohexanecarboxylate. To a 0° C. solution of benzyl 3-oxocyclohexanecarboxylate 1 (2.50 g, 10.8 mmol) in 55 mL of THF was added NaBH$_4$ (814 mg, 21.5 mmol) portionwise. The reaction mixture was maintained at 0° C. for 20 min. Then water was slowly added to the reaction, and the reaction was diluted with Et$_2$O. The resulting layers were separated and the aqueous layer was further extracted with Et$_2$O. The combined organic layers were washed with brine, dried over Na$_2$SO$_4$, filtered and concentrated. Purification of the resulting residue by flash chromatography (Biotage™ 40M 5-25% EtOAc/hexanes then 25-35% EtOAc/hexanes) afforded the title compound as a clear, colorless oil. LCMS: calculated for C$_{14}$H$_{18}$O$_3$ 234.29, observed m/e 235.0 (M+H)$^+$ 256.9 (M+Na) (Rt 1.74/4 min).

INTERMEDIATE 9

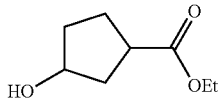

Ethyl 3-hydroxycyclopentanecarboxylate. To a 0° C. solution of ethyl-3-oxo-cyclopentane-1-carboxylate (2.0 g) in THF (50 mL) was added NaBH$_4$ (970 mg). The reaction mixture was maintained at 0° C. for 30 min, and then overnight at ambient temperature. The reaction was then treated with H$_2$O and diluted with Et$_2$O. The resulting layers were separated, and the aqueous layer was further extracted with Et$_2$O. The combined organic layers were washed with brine, dried over Na$_2$SO$_4$, filtered and concentrated. The resulting crude product (a mixture of cis/trans isomers) was used in the next step without further purification.

INTERMEDIATE 10

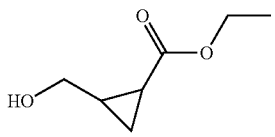

2-Hydroxymethyl-cyclopropanecarboxylic acid ethyl ester. Ethyl 2-formyl-1-cyclopropanecarboxylate (2 ml, 15.11 mmol) was dissolved in methanol (35 ml) and cooled to 0° C. under $N_2$. Sodium borohydride (1.2 g, 31.7 mmol) was added in portions and resulting solution stirred at 0° C. for 2 h. The solution was then diluted by the dropwise addition of water, followed by the addition of EtOAc (100 mL). The aqueous layer was separated and extracted with EtOAc (2×50 mL). The combined organic layers were washed with brine, dried over sodium sulphate and concentrated in vacuo to give the title compound. TLC: 20% EtOAc/hexanes, high Rf: 0.35, low Rf: 0.3.

INTERMEDIATE 11

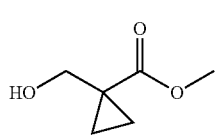

1-Hydroxymethyl-cyclopropanecarboxylic acid methyl ester. 1,1-Cyclopropane dicarboxylic acid-1-methyl ester (4 g, 27.8 mmol) was mixed with DIPEA (6 ml, 34.4 mmol) in THF (50 ml) and stirred at a 0° C. for 10 min. To the reaction was slowly added ethyl chloroformate (2.7 ml, 28.1 mmol). The reaction was stirred for 1.5 hours and allowed to warm to ambient temperature. The reaction was then re-cooled to 0° C. and $NaBH_4$ (1.6 g, 42.3 mmol) was slowly added, followed by the addition of methanol (3 ml, 74.2 mmol). The reaction was allowed to warm to ambient temperature over 2 h. Then the reaction was diluted with EtOAc and water. The aqueous layer was separated and extracted with EtOAc three times. The combined organic layers were washed with water, then brine, dried over ($MgSO_4$), filtered, and concentrated to afford the title compound. $^1$H NMR (500 MHz, $CDCl_3$): δ 3.70 (s, 3H), 3.60 (s, 2H), 1.25 (m, 2H), 0.85 (m, 2H).

INTERMEDIATE 12

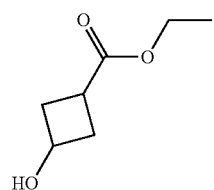

3-Hydroxy-cyclobutanecarboxylic acid ethyl ester. Ethyl 3-oxo cyclobutane carboxylate (2 g, 14.07 mmol) was dissolved in THF (20 ml) and cooled to 0° C. under $N_2$. Sodium borohydride (0.266 g, 7.03 mmol) was added in portions and the resulting solution was stirred at 0° C. for 2 h. The solution was then diluted by the dropwise addition of water, followed by EtOAc (100 mL). The resulting aqueous phase was separated and extracted with EtOAc (2×50 mL). The combined organic layers were washed with brine, dried over sodium sulphate and concentrated in vacuo to give the title compound as a slightly yellow oil. TLC: 25% EtOAc/hexanes, Rf: 0.3.

INTERMEDIATE 13

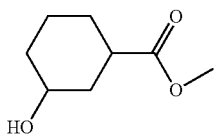

Step A 3-Oxo-cyclohexanecarboxylic acid methyl ester. To a solution of 3-oxo-1-cyclohexanecarboxylic acid (1.2 g, 8.44 mmol) in MeOH (15 ml) was slowly added thionyl chloride (0.7 ml, 9.59 mmol) at room temperature. The reaction mixture was stirred for 3 h, then cooled in an ice bath and quenched slowly by the addition of water. The reaction was neutralized using a saturated aqueous $NaHCO_3$ solution. Then the aqueous layer was extracted with EtOAc. The organic layer was washed with water, then brine and dried over $MgSO_4$, filtered, and concentrated to afford the title compound. $^1$H NMR (500 MHz, $CDCl_3$): δ 3.70 (s, 3H), 2.85 (m, 1H), 2.55 (d, 2H), 2.40-2.30 (m, 2H), 2.15-2.00 (m, 2H), 1.90-1.70 (m, 2H).

Step B Methyl 3-hydroxycyclohexanecarboxylate. 3-oxo-1-cyclohexanecarboxylic acid methyl ester (1.1 g, 7.04 mmol) was dissolved in methanol (25 ml) and cooled to 0° C. under $N_2$. Sodium borohydride (0.550 g, 14.54 mmol) was added in portions and the resulting solution stirred at 0° C. for 2 h. The solution was then diluted by the dropwise addition of water, followed by EtOAc (100 mL). The aqueous phase was separated and extracted with EtOAc (2×50 ml). The combined organic layers were washed with brine, dried over sodium sulphate, and concentrated in vacuo to give the title compound. TLC: 40% EtOAc/hexanes, high Rf: 0.4, low Rf: 0.3.

EXAMPLE 1

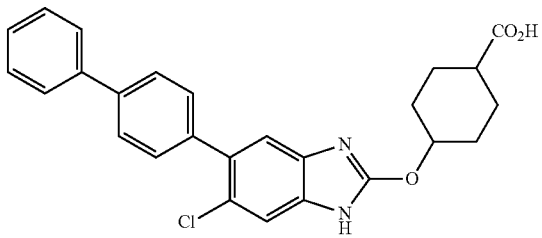 [SMILES: O=C(O)C1CCC(Oc2nc3cc(-c4ccc(-c5ccccc5)cc4)c(Cl)cc3[nH]2)CC1]

4-{[5-(biphenyl-4-yl)-6-chloro-1H-benzimidazol-2-yl]oxy}cyclohexanecarboxylic acid Step A Ethyl 4-{[5-(biphenyl-4-yl)-6-chloro-1-{[2-(trimethylsilyl)ethoxy]methyl}-1H-benzimidazol-2-yl]oxy}cyclohexanecarboxylate. To a solution of 5-(biphenyl-4-yl)-6-chloro-2-(methylsulfonyl)-1-{[2-(trimethylsilyl)ethoxy]methyl}-1H-benzimidazole (Intermediate 3, 190 mg, 0.370 mmol) and ethyl 4-hydroxycyclohexane carboxylate (0.299 mL, 1.85 mmol) in DMF was added DBU (0.251 mL, 1.66 mmol). The mixture was heated at 80° C. for 48 h. The resulting brown reaction mixture was then cooled, and diluted with water and EtOAc. The layers were separated and the aqueous layer was further extracted with EtOAc. The combined organic layers were washed with brine, dried over Na$_2$SO$_4$, filtered, and concentrated. Purification of the resulting residue by preparative TLC (25% EtOAc/hexanes) afforded the desired product as a pale yellow residue. LCMS: calculated for C$_{34}$H$_{41}$ClN$_2$O$_4$Si 605.24, observed m/e 605.02 M$^+$ (Rt 2.98/4 min).

Step B: 4-{[5-(biphenyl-4-yl)-6-chloro-1H-benzimidazol-2-yl]oxy}cyclohexane-carboxylic Acid. To a solution of ethyl 4-{[5-(biphenyl-4-yl)-6-chloro-1-{[2-(trimethylsilyl)ethoxy]methyl}-1H-benzimidazol-2-yl]oxy}cyclohexanecarboxylate (0.075 g, 0.124 mmol) in 2 mL of THF was added TBAF (0.750 mL, 0.750 mmol) dropwise via syringe. The reaction was heated at 80° C. of 2 h, and then the volatiles were removed. The resulting crude ester was dissolved in 4 mL of MeOH and treated with 1 mL of 2.5 N NaOH. The reaction was heated at 45° C. for 1.5 h, and then concentrated. The resulting residue was dissolved in H$_2$O and acidified to pH 1 with 2 N HCl. The acidified aqueous layer was extracted with EtOAc. The combined organic layers were washed with 2 N HCl, H$_2$O, and brine. The organic layers were dried over Na$_2$SO$_4$, filtered, and concentrated. Purification of the resulting residue by reverse phase Gilson™ HPLC (30-100% CH$_3$CN/H$_2$O) afforded the title compound as a white solid. LCMS: calculated for C$_{26}$H$_{23}$ClN$_2$O$_3$ 446.93, observed m/e 446.94 M$^+$ (Rt 2.11/4 min). $^1$H NMR (500 MHz, CD$_3$OD): δ7.70-7.64 (m, 4H), 7.55 (s, 1H), 7.49 (d, 2H), 7.47-7.42 (m, 2H), 7.39 (s, 1H), 7.37-7.32 (m, 1H), 4.97-4.89 (m, 1H), 2.45-2.35 (m, 1H), 2.36-2.28 (m, 2H), 2.18-2.10 (m, 2H), 1.76-1.61 (m, 2H).

EXAMPLE 2

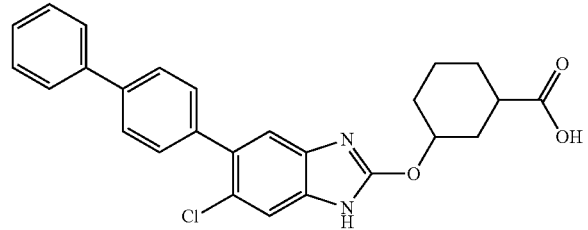 [SMILES: O=C(O)C1CCCC(Oc2nc3cc(-c4ccc(-c5ccccc5)cc4)c(Cl)cc3[nH]2)C1]

3-{[5-(biphenyl-4-yl)-6-chloro-1H-benzimidazol-2-yl]oxy}cyclohexanecarboxylic acid Step A Benzyl 3-{[5-(biphenyl-4-yl)-6-chloro-1-{[2-(trimethylsilyl)ethoxy]methyl}-1H-benzimidazol-2-yl]oxy}cyclohexanecarboxylate. To a solution of 5-(biphenyl-4-yl)-6-chloro-2-(methylsulfonyl)-1-{[2-(trimethylsilyl)ethoxy]methyl}-1H-benzimidazole (Intermediate 3, 369 mg, 0.719 mmol) and benzyl 3-hydroxycyclohexanecarboxylate (Intermediate 8, 1.35 g, 5.75 mmol) in 3 mL DMF was added DBU (0.870 mL, 5.75 mmol) dropwise via syringe. The reaction was heated to 80° C. for 2 h. The resulting light yellow reaction mixture was diluted with EtOAc and washed with H$_2$O and brine. The combined organic layers were dried over Na$_2$SO$_4$, filtered, and concentrated. Purification of the resulting residue by flash chromatography (Biotage™ 40 M 5-10% then 10-20% then 20-25% EtOAc/hexanes) afforded a high Rf product (isomer A) and a low Rf product (isomer B). LCMS: calculated for C$_{39}$H$_{43}$ClN$_2$O$_4$Si 667.31, observed m/e 667.17 M$^+$ (Rt 3.21/4 min)

Step B 3-{[5-(biphenyl-4-yl)-6-chloro-1H-benzimidazol-2-yl]oxy}cyclohexane-carboxylic acid. To a solution of benzyl 3-{[5-(biphenyl-4-yl)-6-chloro-1-{[2-(trimethylsilyl)ethoxy]methyl}-1H-benzimidazol-2-yl]oxy}cyclohexanecarboxylate (isomer A from Step A, 0.075 g, 0.112 mmol) in 1.1 mL of THF was added TBAF (0.675 mL, 0.675 mmol) dropwise via syringe. The reaction was heated at 80° C. for 16 h, and then diluted with EtOAc (50 mL) and washed with 2 N HCl (2×20 mL). The organic layer was washed with H$_2$O and brine, dried over Na$_2$SO$_4$, filtered, and concentrated. Purification of the resulting residue by reverse phase Gilson™ HPLC (30-100% MeCN/H$_2$O) afforded the title compound as a white solid. LCMS: calculated for C$_{26}$H$_{23}$ClN$_2$O$_3$ 446.93, observed m/e 446.92M$^+$ (Rt 2.19/4 min). $^1$H NMR (500 MHz, CD3OD): δ7.71-7.64 (m, 4H), 7.55 (brs, 1H), 7.50 (d, 2H), 7.48-7.43 (m, 2H), 7.39 (brs, 1H), 7.37-7.32 (m, 1H), 5.00-4.91 (m, 1H), 2.60-2.46 (m, 2H), 2.33-2.24 (m, 1H), 2.06-1.95 (m, 2H), 1.79-1.67 (m, 1H), 1.64-1.49 (m, 2H), 1.49-1.37 (m, 1H).

EXAMPLE 3

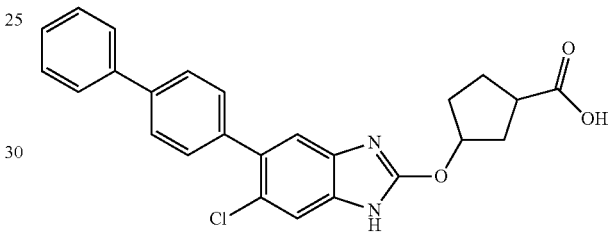

3-{[5-(biphenyl-4-yl)-6-chloro-1H-benzimidazol-2-yl]oxy}cyclopentanecarboxylic acid Step A: Ethyl 3-{[5-(biphenyl-4-yl)-6-chloro-1-{[2-(trimethylsilyl)ethoxy]methyl}-1H-benzimidazol-2-yl]oxy}cyclopentanecarboxylate. To a solution of 5-(biphenyl-4-yl)-6-chloro-2-(methylsulfonyl)-1-{[2-(trimethylsilyl)ethoxy]methyl}-1H-benzimidazole (Intermediate 3, 0.350 g, 0.682 mmol) and ethyl 3-hydroxycyclopentanecarboxylate (Intermediate 9, 0.647 mL, 4.09 mmol) in 2.3 mL DMF was added DSU (0.514 mL. 3.41 mmol) dropwise via syringe. The reaction was heated overnight at 80° C., then diluted with EtOAc, and washed with H$_2$O and brine. The aqueous layer was further extracted with EtOAc, and the combined organic layers were dried over Na$_2$SO$_4$, filtered, and concentrated. Purification of the resulting residue by preparative TLC (25% EtOAc/hexanes) furnished the desired compound as a pale yellow oil. LCMS: calculated for C$_{33}$H$_{39}$ClN$_2$O$_4$Si 591.21, observed m/e 591.04 M$^+$ (Rt 3.06/4 min).

Step B: 3-{[5-(biphenyl-4-yl)-6-chloro-1H-benzimidazol-2-yl]oxy}cyclopentane carboxylic acid. To a solution of ethyl 3-{[5-(biphenyl-4-yl)-6-chloro-1-{[2-(trimethylsilyl)ethoxy]methyl}-1H-benzimidazol-2-yl]oxy}cyclopentanecarboxylate (80 mg, 0.135 mmol) in 2.7 mL of THF was added TBAF (0.700 mL, 0.700 mmol) dropwise via syringe. The reaction was heated at 80° C. for 1.5 h. After heating for 4 h, the reaction was concentrated and the residue was re-dissolved in 4 mL of MeOH and treated with 1 mL of 2.5 N NaOH. The reaction was maintained at ambient temperature overnight. Then the solvent was removed and the resulting residue was dissolved in H$_2$O and acidified to pH 1 with 2 N HCl. The aqueous layer was separated and extracted with EtOAc. The combined organic layers were washed with 2 N HCl, H₂O, and brine. The combined organic layers were then dried over Na₂SO₄, filtered, and concentrated. Purification of the resulting residue by reverse phase Gilson™ HPLC (30-100% MeCN/H₂O) afforded a 1:1 cis/trans mixture of the title compound as a white solid. LCMS: calculated for $C_{25}H_{21}ClN_2O_3$ 432.89, observed m/e 432.93 M⁺ (Rt 2.13/4 min). ¹H NMR (500 MHz, CD3OD): δ7.7.72-7.63 (m, 8H), 7.58-7.55 (m, 2H), 7.49 (d, 4H), 7.47-7.42 (m, 4H), 7.42-7.38 (m, 2H), 7.37-7.32 (m, 2H), 5.54-5.47 (m, 1H), 5.46-5.40 (m, 1H), 3.16-3.05 (m, 1H), 3.05-2.95 (m, 1H), 2.54-2.43 (m, 1H), 2.42-2.31 (m, 3H), 2.31-1.95 (m, 8H).

EXAMPLE 4

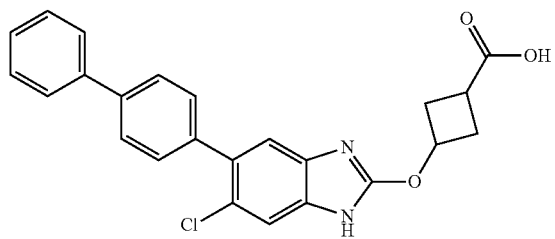 [SMILES: O=C(O)C1CC(Oc2nc3cc(-c4ccc(-c5ccccc5)cc4)c(Cl)cc3[nH]2)C1]

3-{[5-(biphenyl-4-yl)-6-chloro-1H-benzimidazol-2-yl]oxy}cyclobutanecarboxylic acid Step A Ethyl 3-{[5-(biphenyl-4-yl)-6-chloro-1-{[2-(trimethylsilyl)ethoxy]methyl}-1H-benzimidazol-2-yl]oxy}cyclobutanecarboxylate. To a solution of 5-(biphenyl-4-yl)-6-chloro-2-(methylsulfonyl)-1-{[2-(trimethylsilyl)ethoxy]methyl}-1H-benzimidazole (Intermediate 3, 150 mg, 0.292 mmol) and 3-hydroxy-cyclobutanecarboxylic acid ethyl ester (Intermediate 12, 200 mg, 1.387 mmol) in DMF (2 ml) was added DBU (0.25 ml, 1.659 mmol) dropwise via syringe. The reaction mixture was heated at 80° C. for 3 h. Then the volatiles were removed in vacuo and the resulting residue was partitioned between EtOAc and H₂O. The organic phase was separated, washed with water and brine, dried over MgSO₄ and concentrated in vacuo. Chromatography of the resulting residue over silica (preparative TLC) eluting with 30% EtOAc/hexanes afforded the title compound. LC-MS: calculated for $C_{32}H_{37}ClN_2O_4Si$ 576.22, observed m/e: 577.04 (M+H)⁺ (R, 2.98/4 min).

Step B 3-{[5-(biphenyl-4-yl)-6-chloro-1H-benzimidazol-2yl]oxy}cyclobutanecarboxylic acid. To a solution of ethyl 3-{[5-(biphenyl-4-yl)-6-chloro-1-{[2-(trimethylsilyl)ethoxy]-methyl}-1H-benzimidazol-2-yl]oxy}cyclobutanecarboxylate (100 mg, 0.173 mmol) in formic acid (1.7 ml) was added a saturated aqueous solution of potassium bisulfate (0.3 ml, 0.173 mmol). The reaction mixture was heated at 80° C. for 1 h. Then the volatiles were removed in vacuo and the resulting residue was acidified with 1N aqueous HCl and extracted with EtOAc. The organic phase was separated, washed with water, and concentrated in vacuo. Purification of the resulting residue by reverse phase HPLC eluting with 30-100% MeCN:H₂O afforded the title compound as a white solid. LC-MS: calculated for $C_{24}H_{19}ClN_2O_3$ 418.11, observed m/e: 418.93 (M+H)⁺ (R, 2.16/4 min). ¹H NMR (500 MHz, CD₃OD): δ 7.75-7.35 (m, 11H), 5.25-5.20 (m, 1H), 2.90 (m, 31-1) 2.50 (m, 2H).

EXAMPLE 5

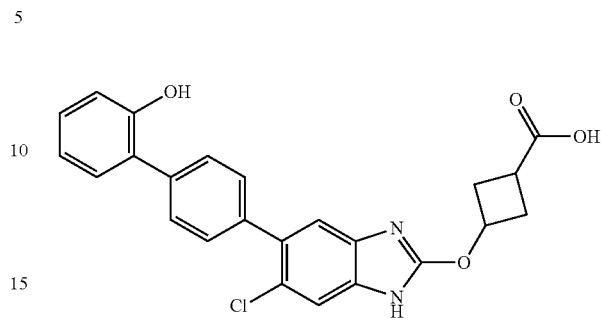

3-{[6-chloro-5-(2'-hydroxybiphenyl-4-yl)-1H-benzimidazol-2-yl]oxy}cyclobutanecarboxylic acid Step A Ethyl 3-[(6-chloro-5-iodo-1-{[2-(trimethylsilyl)ethoxy]methyl}-1H-benzimidazol-2-yl)oxy]cyclobutanecarboxylate. The title compound was prepared from 6-chloro-5-iodo-2-(methylsulfonyl)-1-{[2-(trimethylsilyl)ethoxy]methyl}-1H-benzimidazole (Intermediate 2, 2g, 4.11 mmol) and 3-hydroxy-cyclobutanecarboxylic acid ethyl ester (Intermediate 12, 2.43 g, 16.86 mmol) in DMF (30 ml) and DBU (3.10 ml, 20.54 mmol) according to the procedure for Example 4, Step A. Chromatography of the resulting crude product over silica eluting with 5-15% EtOAc/hexanes afforded the title compound. LC-MS: calculated for $C_{20}H_{28}ClIN_2O_4Si$ 550.06, observed m/e: 550.85 (M+H)⁺ (R, 2.6/4 min).

Step B ethyl 3-{[5-(4-bromophenyl)-6-chloro-1-{[2-(trimethylsilyl)ethoxy]methyl}-1H-benzimidazol-2-yl]oxy}cyclobutanecarboxylate. A 250 mL flask was charged with ethyl 3-[(6-chloro-5-iodo-1-{[2-(trimethylsilyl)ethoxy]methyl}-1H-benzimidazol-2-yl)oxy]cyclobutanecarboxylate (1.39 g, 2.52 mmol), 4-bromophenylboronic acid (0.583 g, 2.90 mmol), Pd(PPh₃)₄ (0.233 g, 0.202 mmol), DMF (30 mL), and 2 M aqueous K₃PO₄ (3.78 ml, 7.57 mmol). The reaction was degassed with N₂ and then heated at 90° C. for 4 hours. The volatiles were removed in vacuo and the resulting residue was partitioned between EtOAc and H₂O. The aqueous phase was extracted with EtOAc. The combined organic layers were washed with brine, dried (MgSO₄), filtered, and concentrated. Chromatography of the resulting residue over silica eluting with 5-50% EtOAc/hexanes afforded the desire product as white solid. LC-MS: calculated for $C_{26}H_{32}BrClN_2O_4Si$ 578.1, observed m/e: 578.92 (M+H)⁺ (R, 2.76/4 min).

Step C Ethyl 3-{[6-chloro-5-(2'-hydroxybiphenyl-4-yl)-1-{[2-(trimethylsilyl)ethoxy]methyl}-1H-benzimidazol-2-yl]oxy}cyclobutanecarboxylate. A 50 mL flask was charged with ethyl 3-{[5-(4-bromophenyl)-6-chloro-1-{[2-(trimethylsilyl)ethoxy]methyl}-1H-benzimidazol-2-yl]oxy}cyclobutanecarboxylate (150 mg, 0.259 mmol), 2-hydroxybenzeneboronic acid, pinacol ester (60 mg, 0.273 mmol), Pd(PPh₃)₄ (20 mg, 0.017 mmol), DMF (5 mL), and 1 M aqueous K₂CO₃ (0.78 ml, 0.780 mmol). The reaction was degassed with N₂ and then heated at 120° C. for 1 hour. Then the volatiles were removed in vacuo and the residue partitioned between EtOAc and H₂O. The aqueous phase was extracted with EtOAc. The combined organic layers were washed with brine, dried over (MgSO₄), filtered, and concentrated. Chromatography of the resulting residue over silica (preparative TLC) eluting with 45% EtOAc/hexanes afforded the desired product. LC-MS: calculated for $C_{32}H_{37}ClN_2O_5Si$ 592.22, observed m/e: 593.05 (M+H)⁺ ($R_t$ 2.67/4 min).

Step D 3-{[6-chloro-5-(2'-hydroxybiphenyl-4-yl)-1H-benzimidazol-2-yl]oxy}cyclobutanecarboxylic acid. To a solution of ethyl 3-{[6-chloro-5-(2'-hydroxybiphenyl-4-yl)-1-{[2-(trimethylsilyl)ethoxy]methyl}-1H-benzimidazol-2-yl]oxy}cyclobutanecarboxylate (153 mg, 0.258 mmol) in formic acid (4 mL) was added saturated aqueous solution of potassium bisulfate (0.8 ml, 0.258 mmol). The reaction mixture was heated at 80° C. overnight. Then the volatiles were removed in vacuo, and the residue acidified with 1 N aqueous HCl, and extracted with EtOAc. The organic phase was separated, washed with water, and concentrated in vacuo. Purification of the resulting residue by reverse phase HPLC (20-100% MeCN: H₂O) afforded the title compound as a white solid. LC-MS: calculated for $C_{24}H_{19}ClN_2O_4$ 434.1, observed m/e: 434.99 (M+H)⁺ ($R_t$ 1.82/4 min). ¹H NMR (500 MHz, CD₃OD): δ 7.70-6.90 (m, 10H), 5.25-5.20 (m, 1H), 2.90 (m, 3H) 2.50 (m, 2H).

EXAMPLE 6

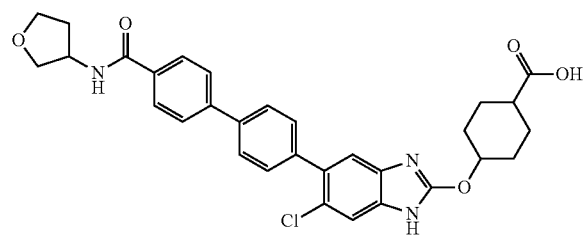 [SMILES: O=C(NC1CCOC1)c1ccc(-c2ccc(-c3cc4nc(OC5CCC(C(=O)O)CC5)[nH]c4cc3Cl)cc2)cc1]

4-({6-chloro-5-[4'-(tetrahydrofuran-3-ylcarbamoyl)biphenyl-4-yl]-1H-benzimidazol-2-yl}oxy)cyclohexanecarboxylic acid Step A Ethyl 4-[(6-chloro-5-[4'-(tetrahydrofuran-3-Ylcarbamoyl)biphenyl-4-yl]-1-{[2-(trimethylsilyl)ethoxy]methyl}-1H-benzimidazol-2-yl)oxy]cyclohexanecarboxylate. The title compound was prepared according to the procedures described for Example 5, steps A, B and C by substituting 3-hydroxy-cyclobutanecarboxylic acid ethyl ester with ethyl 4-hydroxycyclohexanecarboxylate (Step A), and by substituting 2-hydroxybenzene boronic acid, pinacol ester with N-(tetrahydrofuran-3-yl)-4-(4,4,5,5-tetramethyl-1,3,2-dioxaborolan-2-yl)benzamide (Step C). LC-MS: calculated for $C_{39}H_{48}ClN_3O_6Si$ 718.35, observed m/e: 560.15 (M+H)⁺ ($R_t$ 1.82/4 min).

Step B 4-({6-chloro-5-[4'-(tetrahydrofuran-3-ylcarbamoyl)biphenyl-4-yl]-1H-benzimidazol-2-yl}oxy)cyclohexanecarboxylic acid. To a solution of ethyl 4-[(6-chloro-5-[4'-(tetrahydrofuran-3-ylcarbamoyl)biphenyl-4-yl]-1-{[2-(trimethylsilyl)ethoxy]-methyl}-1H-benzimidazol-2-yl)oxy]cyclohexanecarboxylate (0.115 g, 0.160 mmol) in THF (3 mL) was added KOTMS (0.062 g, 0.483 mmol). The reaction was maintained overnight at ambient temperature. Then the volatiles were removed in vacuo, and the resulting residue was acidified with 1 N aqueous HCl, and extracted with EtOAc. The organic phase was concentrated to afford the desired carboxylic acid intermediate, which was used in the next step without further purification.

To a solution of the carboxylic acid intermediate (0.090 g, 0.130 mmol) in dioxane (2 mL) was added TBAF (0.63 mL, 0.78 mmol) dropwise via syringe. The reaction mixture was heated at 80° C. for 3 h. Then the volatiles were removed in vacuo and the resulting residue was acidified with 1 N aqueous HCl, and extracted with EtOAc. The organic phase was washed with H₂O and brine, dried over (MgSO₄), filtered, and concentrated in vacuo. Purification of the resulting residue by reverse phase HPLC eluting with 10-100% MeCN:H₂O afforded the title compound. LC-MS: calculated for $C_{31}H_{30}ClN_3O_5$ 559.19, observed m/e: 560.15 (M+H)⁺ ($R_t$ 1.82/4 min). ¹H NMR (500 MHz, C₂D₆OS): δ 8.60 (d, 1H), 8.00 (m, 2H), 7.80 (m, 4H), 7.50 (m, 2H), 7.40 (b, 1H), 7.20 (b, 1H), 4.90 (m, 1H), 4.50 (m, 1H), 3.90 (m, 2H), 3.70 (m, 1H), 3.60 (m, 1H), 2.30-2.10 (m, 4H), 2.00-1.90 (m, 3H), 1.60-1.40 (m, 4H).

Examples 7-12 in Table 1 were prepared following the procedures described in Example 5 by substituting the appropriate boronic acid or boronate ester from the Intermediates, or from commercial sources; and by substituting the appropriate hydroxycycloalkanoates from the Intermediates, or from commercial sources. Examples 9-12 employed the deprotection sequence outlined in Step B of Example 6.

TABLE 1

Compounds prepared according to the methods described in Examples 5 and 6.

| Example Number | Structure | HPLC-mass spectrum m/e |
|---|---|---|
| 7 | 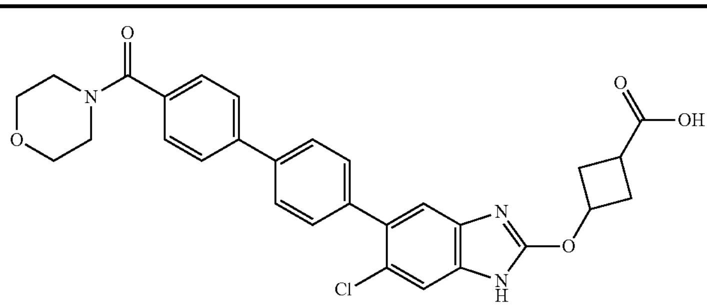 | 532.0 |

TABLE 1-continued

Compounds prepared according to the methods described in Examples 5 and 6.

| Example Number | Structure | HPLC-mass spectrum m/e |
|---|---|---|
| 8 | 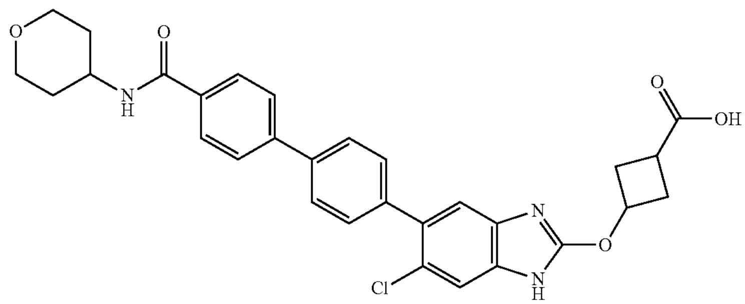 [SMILES: O=C(NC1CCOCC1)c1ccc(-c2ccc(-c3cc4nc(OC5CC(C(=O)O)C5)[nH]c4cc3Cl)cc2)cc1] | 546.1 |
| 9 | 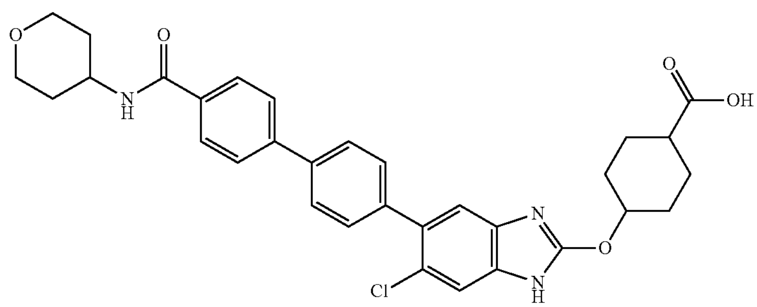 [SMILES: O=C(NC1CCOCC1)c1ccc(-c2ccc(-c3cc4nc(OC5CCC(C(=O)O)CC5)[nH]c4cc3Cl)cc2)cc1] | 574.1 |
| 10 | 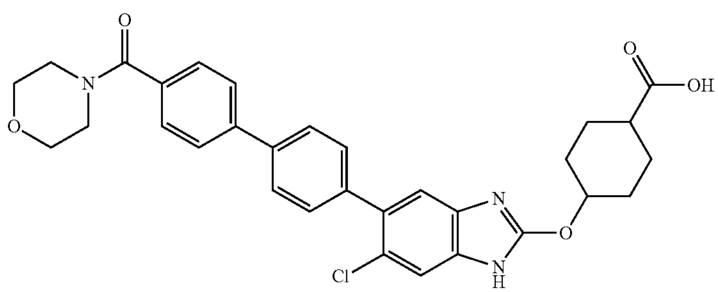 [SMILES: O=C(O)C1CCC(Oc2nc3cc(-c4ccc(-c5ccc(C(=O)N6CCOCC6)cc5)cc4)c(Cl)cc3[nH]2)CC1] | 560.2 |
| 11 | 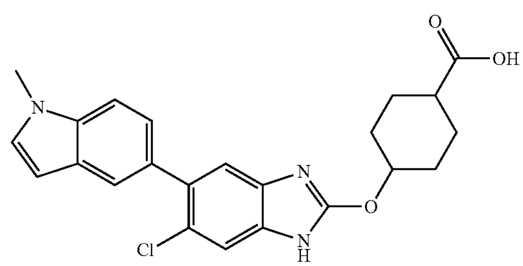 [SMILES: Cn1ccc2cc(-c3cc4nc(OC5CCC(C(=O)O)CC5)[nH]c4cc3Cl)ccc21] | 424.1 |
| 12 | 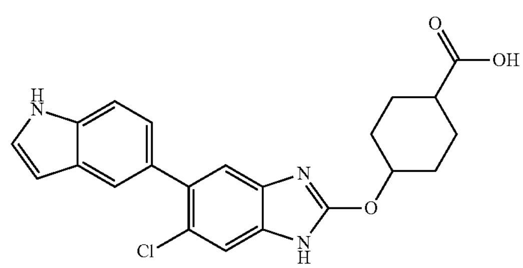 [SMILES: O=C(O)C1CCC(Oc2nc3cc(-c4ccc5[nH]ccc5c4)c(Cl)cc3[nH]2)CC1] | 410.1 |

EXAMPLE 13

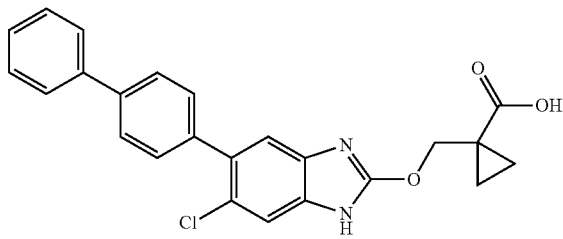 [SMILES: O=C(O)C1(COc2nc3cc(-c4ccc(-c5ccccc5)cc4)c(Cl)cc3[nH]2)CC1]

1-({[5-biphenyl-4-yl]-6-chloro-1H-benzimidazol-2-yl]oxy}methyl)cyclopropane carboxylic acid Step A Methyl 1-({[5-(biphenyl-4-yl)-6-chloro-1-(prop-2-en-1-yl)-1H-benzimidazol-2-yl]oxy}methyl)cyclopropanecarboxylate. To a solution of 5-(biphenyl-4-yl)-6-chloro-2-(methylsulfonyl)-1-(prop-2-en-1-yl)-1H-benzimidazole (Intermediate 4, 150 mg, 0.355 mmol) and methyl-1-(hydroxymethyl)cyclopropane carboxylate (Intermediate 11, 70 mg, 0.538 mmol) in DMF (2 ml) was added DBU (0.27 ml, 1.791 mmol) dropwise. The reaction mixture was stirred overnight at 80° C. The volatiles were removed in vacuo and the resulting residue partitioned between EtOAc and H$_2$O. The aqueous phase was extracted with EtOAc. The combined organic layers were washed with brine, dried (MgSO$_4$), filtered, and concentrated. Chromatography of the resulting residue over silica (preparative TLC) eluting with 35% EtOAc/hexanes afforded the desired product. LC-MS: calculated for C$_{28}$H$_{25}$ClN$_2$O$_3$ 472.16, observed m/e: 472.89 (M+H)$^+$ (R$_t$ 2.66/4 min).

Step B 1-({[5-(biphenyl-4-yl)-6-chloro-1H-benzimidazol-2-yl]oxy}methyl)cyclopropane carboxylic acid. A 25 ml flask was charged with methyl-1-({[5-(biphenyl-4-yl)-6-chloro-1-(prop-2-en-1-yl)-1H-benzimidazol-2-yl]oxy}methyl)cyclopropanecarboxylate (100 mg, 0.211 mmol), 1,3-Dimethylbarbituric acid (100 mg, 0.640 mmol), Pd(PPh$_3$)$_4$ (25 mg, 0.022 mmol) and EtOH (2 ml). The resulting mixture was degassed with N$_2$ for 1 min, and then heated at 70° C. for 15 h. Then the volatiles were removed in vacuo and the residue was partitioned between EtOAc and H$_2$O. The aqueous phase was extracted with EtOAc. The combined organic layers were washed with Na$_2$CO$_3$ and brine, dried over (MgSO$_4$) and filtered. The organic phase was concentrated to afford the desire methyl ester intermediate, which was used in the following hydrolysis step without further purification.

To a solution of methyl ester intermediate (28 mg) in 2 ml of MeOH, and 0.5 ml of THF was added 2 ml of 2.5 N NaOH. The reaction mixture was maintained at ambient temperature for 1 h. Then the volatiles were removed in vacuo and the residue was acidified with 1 N aqueous HCl, and extracted with EtOAc. The organic phase was washed with water and concentrated in vacuo. Purification of the resulting residue by reverse phase HPLC eluting with 35-100% MeCN:water afforded the title compound as a white solid. LC-MS: calculated for C$_{24}$H$_{19}$ClN$_2$O$_3$ 418.11, observed m/e: 418.97 (M+H)$^+$ (R$_t$ 2.12/4 min). $^1$H NMR (500 MHz, CD$_3$OD): δ 7.75-7.35 (m, 11H), 4.70 (s, 2H), 1.45 (q, 2H), 1.20 (q, 2H).

EXAMPLE 14

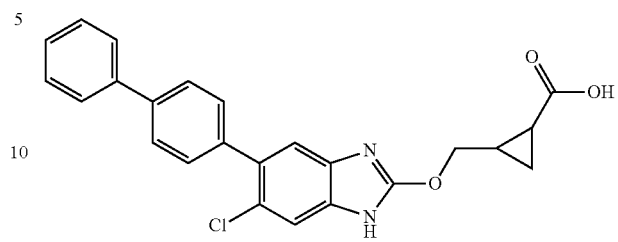

2-({[5-biphenyl-4-yl]-6-chloro-1H-benzimidazol-2-yl]oxy}methyl)cyclopropane carboxylic acid Step A ethyl 2-({[5-(biphenyl-4-yl)-6-chloro-1-(prop-2-en-1-yl)-1H-benzimidazol-2-yl]oxy}methyl)cyclopropanecarboxylate. The title compound was prepared by treating 5-(biphenyl-4-yl)-6-chloro-2-(methylsulfonyl)-1-(prop-2-en-1-yl)-1H-benzimidazole (Intermediate 4, 150 mg, 0.355 mmol) and 2-hydroxymethyl-cyclopropanecarboxylic acid ethyl ester (Intermediate 10, 70 mg, 0.538 mmol) in DMF (3 ml) with DBU (0.14 ml, 0.8 mmol) according to the procedure for Example 13, Step A. The reaction mixture was stirred at 80° C. for 4 hours. Chromatography of the resulting crude product over silica (preparative TLC) eluting with 45% EtOAc/hexanes afforded the desired product. LC-MS: calculated for C$_{29}$H$_{27}$ClN$_2$O$_3$ 486.17, observed m/e: 486.93 (M+H)$^+$ (R$_t$ 2.73/4 min).

Step B 2-({[5-(biphenyl-4-yl)-6-chloro-1H-benzimidazol-2-yl]oxy}methyl)cyclopropane carboxylic acid. The title compound was prepared from ethyl 2-({[5-(biphenyl-4-yl)-6-chloro-1-(prop-2-en-1-yl)-1H-benzimidazol-2-yl]oxy}methyl)cyclopropanecarboxylate (115 mg, 0.236 mmol), 1,3-dimethylbarbituric acid (111 mg, 0.708 mmol), Pd(PPh$_3$)$_4$ (30 mg, 0.026 mmol) and EtOH (2.5 ml) according to the procedure described for Example 13, Step B. Purification of the resulting crude product by reverse phase HPLC eluting with 35-100% MeCN:water afforded the title compound as a white solid. LC-MS: calculated for C$_{24}$H$_{19}$ClN$_2$O$_3$ 418.11, observed m/e: 418.97 (M+H)$^+$ (R$_t$ 2.12/4 min). $^1$H NMR (500 MHz, CD$_3$OD): 7.75-7.35 (m, 11H), 4.50 (dd, 2H), 4.30 (dd, 2H) 1.85 (m, 1H), 1.70 (m, 1H), 1.10 (m, 11H), 1.05 (m, 1H).

EXAMPLE 15

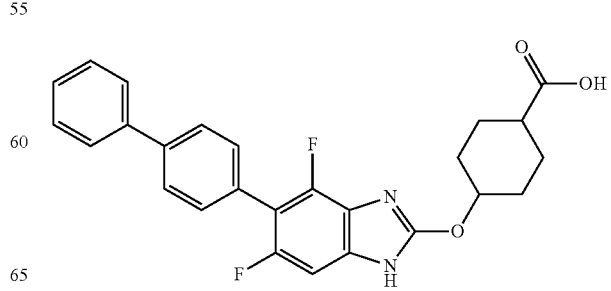

4-{[5-(biphenyl-4-yl)-4,6-difluoro-1H-benzimidazol-2-yl]oxy}-cyclohexane carboxylic acid Step A Ethyl 4-{[1-(biphenyl-4-ylmethyl)-4,6-difluoro-5-iodo-1H-benzimidazol-2-yl]oxy}cyclohexanecarboxylate. To a solution of 1-(biphenyl-4-ylmethyl)-4,6-difluoro-5-iodo-2-(methylsulfonyl)-1H-benzimidazole (Intermediate 5, 20 g, 38.1 mmol) and ethyl 4-hydroxycyclohexanecarboxylate (21 ml, 130 mmol, Aldrich, a mixture of cis and trans isomers) in DMF (70 ml) was added DBU (23 ml, 130 mmol) dropwise at room temperature. The reaction mixture was heated at 80° C. overnight. Then the volatiles were removed in vacuo and the resulting residue partitioned between EtOAc and $H_2O$. The organic phase was separated, washed with water and brine, dried over $MgSO_4$ and concentrated in vacuo. Chromatography of the resulting residue over silica eluting with 15% EtOAc/hexane afforded the title compound as a mixture of trans and cis isomers. LC-MS: calculated for $C_{29}H_{27}F_2IN_2O_3$ 616.1, observed m/e: 617.20 $(M+H)^+$ ($R_t$ 2.82/4 min).

Step B Ethyl 4-{[5-(biphenyl-4-yl)-1-(biphenyl-4-ylmethyl)-4,6-difluoro-1H-benzimidazol-2-yl]oxy}cyclohexanecarboxylate. A 250 mL flask was charged with ethyl 4-{[1-(biphenyl-4-ylmethyl)-4,6-difluoro-5-iodo-1H-benzimidazol-2-yl]oxy}cyclohexane carboxylate (2 g, 3.24 mmol), 4-Biphenylboronic acid (0.700 g, 3.53 mmol), $Pd(PPh_3)_4$ (0.185 g, 0.160 mmol), DMF (30 mL), and 1 M aqueous $K_2CO_3$ (6.5 ml, 6.50 mmol). The reaction was degassed with $N_2$ and then heated at 120° C. for 1 hour. The volatiles were removed in vacuo and the resulting residue was partitioned between EtOAc and $H_2O$. The aqueous phase was extracted with EtOAc. The combined organic layers were washed with brine, dried ($MgSO_4$), filtered, and concentrated. Chromatography of the resulting residue over silica eluting with 15% [EtOAc:DCM (1:1)]/hexanes afforded the desired trans product as white solid. LC-MS: calculated for $C_{41}H_{36}F_2N_2O_3$ 642.27, observed m/e: 643.14 $(M+H)^+$ ($R_t$ 3.07/4 min).

Step C Ethyl 4-{[5-(biphenyl-4-yl)-4,6-difluoro-1H-benzimidazol-2-yl]oxy}cyclohexanecarboxylate. A suspension of ethyl 4-{[5-(biphenyl-4-yl)-1-(biphenyl-4-ylmethyl)-4,6-difluoro-1H-benzimidazol-2-yl]oxy}cyclohexanecarboxylate (1.06 g, 1.649 mmol) and Pearlman's Catalyst (0.300 g, 0.427 mmol) in ethyl acetate (15 ml) and EtOH (7.5 ml) was treated with 1,4-cyclohexadiene (3.55 ml, 37.9 mmol). The resulting reaction mixture was microwaved at 120° C. for 90 minutes, and then cooled. The cooled reaction mixture was filtered through a Celite™ pad and the volatiles were removed in vacuo. Chromatography of the resulting residue over silica eluting with 20% THF/hexanes afforded the desired trans product as white solid. LC-MS: calculated for $C_{28}H_{26}F_2N_2O_3$ 476.19, observed m/e: 477.01 $(M+H)^+$ ($R_t$ 2.6/4 min).

Step D 4-{[5-(biphenyl-4-yl)-4,6-difluoro-1H-benzimidazol-2-yl]oxy}-cyclohexane carboxylic acid. To a solution of ethyl 4-{[5-(biphenyl-4-yl)-4,6-difluoro-1H-benzimidazol-2-yl]oxy}cyclohexanecarboxylate (0.615 g, 1.291 mmol) in THF (5 ml) was added potassium trimethyl silanolate (0.550 g, 4.29 mmol). The reaction was stirred overnight at ambient temperature. Then the volatiles were removed in vacuo and the resulting residue was acidified with 1N aqueous HCl and extracted with EtOAc. The organic phase was washed with water and concentrated in vacuo. Purification of the resulting residue by reverse phase HPLC eluting with 50-100% MeCN:$H_2O$ afforded the title compound as a white solid. LC-MS: calculated for $C_{26}H_{22}F_2N_2O_3$ 448.16, observed m/e 449.01 $(M+H)^+$ ($R_t$ 2.32/4 min). $^1H$ NMR (500 MHz, $C_2D_6OS$): δ 7.80-7.70 (m, 4H), 7.55-7.45 (m, 4H), 7.40 (m, 1H), 7.15 (d, 1H), 5.00-4.90 (m, 1H), 2.30 (m, 1H), 2.25 (m, 2H), 2.00 (m, 2H), 1.50 (m, 4H).

EXAMPLE 16

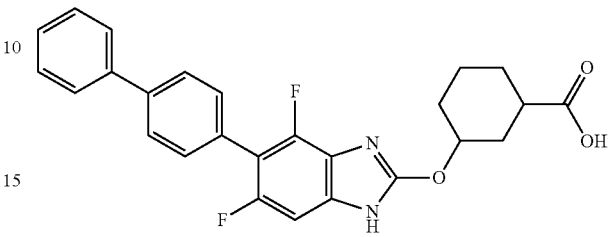

3-{[5-(biphenyl-4-yl)-4,6-difluoro-1H-benzimidazol-2-yl]oxy}cyclohexanecarboxylic acid Step A Methyl 3-{[1-(biphenyl-4-ylmethyl)-4,6-difluoro-5-iodo-1H-benzimidazol-2-yl]oxy}cyclohexanecarboxylate. To a solution of 1-(biphenyl-4-ylmethyl)-4,6-difluoro-5-iodo-2-(methylsulfonyl)-1H-benzimidazole (Intermediate 5, 0.528 g, 1.00 mmol) and methyl 3-hydroxycyclohexanecarboxylate (Intermediate 13, 1 g, 6.32 mmol) in DMF (5 ml) was added DBU (0.5 ml, 3.32 mmol) dropwise at room temperature. The reaction mixture was heated at 80° C. overnight. Then the volatiles were removed in vacuo and the resulting residue was partitioned between EtOAc and $H_2O$. The organic phase was separated, washed with $H_2O$ and brine, dried over $MgSO_4$ and concentrated in vacuo. Chromatography of the resulting residue over silica eluting with 15% EtOAc/hexane afforded the title compound. LC-MS: calculated for $C_{28}H_{25}F_2IN_2O_3$ 602.09, observed m/e: 602.96 $(M+H)^+$ ($R_t$ 2.59/4 min).

Step B Methyl 3-{[5-(biphenyl-4-yl)-1-(biphenyl-4-ylmethyl)-4,6-difluoro-1H-benzimidazol-2-yl]oxy}cyclohexanecarboxylate. A 50 mL flask was charged with methyl 3-{[1-(biphenyl-4-ylmethyl)-4,6-difluoro-5-iodo-1H-benzimidazol-2-yl]oxy}cyclohexanecarboxylate (0.4 g, 0.664 mmol), 4-biphenylboronic acid (0.130 g, 0.664 mmol), $Pd(PPh_3)_4$ (0.038 g, 0.033 mmol), DMF (9 mL), and 1 M aqueous $K_2CO_3$ (1.3 ml, 1.30 mmol). The reaction was degassed with $N_2$ and then heated at 120° C. for 1 h. Then the volatiles were removed in vacuo and the resulting residue was partitioned between EtOAc and $H_2O$. The aqueous phase was separated and extracted with EtOAc. The combined organic layers were washed with brine, dried ($MgSO_4$), filtered, and concentrated. Chromatography of the resulting residue over silica (preparative TLC) eluting with 40% EtOAc/hexanes afforded the title compound. LC-MS: calculated for $C_{40}H_{34}F_2N_2O_3$ 628.25, observed m/e: 629.17 $(M+H)^+$ ($R_t$ 3.83/4 min).

Step C Methyl 3-{[5-(biphenyl-4-yl)-4,6-difluoro-1H-benzimidazol-2-yl]oxy}cyclohexanecarboxylate. A suspension of methyl 3-{[5-(biphenyl-4-yl)-1-(biphenyl-4-ylmethyl)-4,6-difluoro-1H-benzimidazol-2-yl]oxy}cyclohexanecarboxylate (0.080 g, 0.127 mmol) and Pearlman's Catalyst (0.016 g, 0.023 mmol) in EtOAc (1.5 ml) and EtOH (0.75 ml) was treated with 1,4-cyclohexadiene (0.24 ml, 2.56 mmol). The resulting reaction mixture was microwaved at 120° C. for 90 minutes and then cooled. The cooled reaction mixture was filtered through a Celite™ pad and the filtrate was removed in vacuo. Purification of the resulting residue by reverse phase HPLC eluting with 50-100% MeCN/H$_2$O afforded the title compound as a white solid. LC-MS: calculated for C$_{27}$H$_{24}$F$_2$N$_2$O$_3$ 462.18, observed m/e: 463.01.01 (M+H)$^+$ (R$_t$ 2.31/4 min).

Step D 3-[5-(biphenyl-4-yl)-4,6-difluoro-1H-benzimidazol-2-yl]oxy)cyclohexanecarboxylic acid. To a solution of methyl 3-{[5-(biphenyl-4-yl)-4,6-difluoro-1H-benzimidazol-2-yl]oxy}cyclohexanecarboxylate (0.0077 g, 0.017 mmol) in THF (1 mL) was added KOTMS (0.010 g, 0.078 mmol). The reaction was maintained overnight at ambient temperature, and then the volatiles were removed in vacuo. The resulting residue was acidified with 1N aqueous HCl and extracted with EtOAc. The organic phase was separated, washed with H$_2$O and concentrated in vacuo. Purification of the resulting residue by reverse phase HPLC eluting with 50-100% MeCN: H$_2$O afforded the title compound as a white solid. LC-MS: calculated for C$_{26}$H$_{22}$F$_2$N$_2$O$_3$ 448.16, observed m/e 449.05 (M+H)$^+$ (R$_t$ 2.19/4 min). $^1$H NMR (500 MHz, CD$_3$OD): δ 7.80-7.70 (m, 4H), 7.50-7.40 (m, 4H), 7.35 (m, 1H), 7.05 (d, 1H), 5.00-4.90 (m, 1H), 2.60-2.50 (m, 2H), 2.30-2.20 (m, 1H), 2.05-1.95 (m, 2H), 1.70-1.50 (m, 4H).

EXAMPLE 17

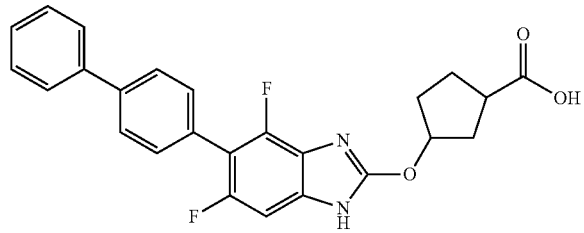 [SMILES: O=C(O)C1CCC(Oc2nc3c(F)c(-c4ccc(-c5ccccc5)cc4)c(F)cc3[nH]2)C1]

3-{[5-(biphenyl-4-yl)-4,6-difluoro-1H-benzimidazol-2-yl]oxy}cyclopentanecarboxylic acid Step A: Ethyl 3-{[1-(biphenyl-4-ylmethyl)-4,6-difluoro-5-iodo-1H-benzimidazol-2-yl]oxy}cyclopentanecarboxylate. To a solution of 1-(biphenyl-4-ylmethyl)-4,6-difluoro-5-iodo-2-(methylsulfonyl)-1H-benzimidazole (Intermediate 5, 0.650 g, 1.24 mmol) and ethyl 3-hydroxycyclopentanecarboxylate (Intermediate 9, 0.784 g, 4.96 mmol) in 4 mL of DMF was added DBU (0.747 mL, 4.96 mmol) dropwise via syringe. The reaction was heated overnight at 80° C., and then diluted with EtOAc and H$_2$O. The layers were separated and the aqueous layer was extracted with EtOAc. The combined organic layers were washed with brine, dried over Na$_2$SO$_4$, filtered, and concentrated. Purification of the resulting residue by flash chromatography (3-25% EtOAc/hexanes) afforded the desired product. LCMS: calculated for C$_{28}$H$_{25}$F$_2$IN$_2$O$_3$ 602.41, observed m/e 602.9 (M+H)$^+$ (Rt 2.57/4 min).

Step B: Ethyl 3-{[5-(biphenyl-4-yl)-1-(biphenyl-4-ylmethyl)-4,6-difluoro-1H-benzimidazol-2-yl]oxy}cyclopentanecarboxylate. A solution of ethyl 3-{[1-(biphenyl-4-ylmethyl)-4,6-difluoro-5-iodo-1H-benzimidazol-2-yl]oxy}cyclopentanecarboxylate (0.290 g, 0.481 mmol), biphenylboronic acid (0.105 g, 0.530 mmol), and Pd(PPh$_3$)$_4$ (22 mg, 0.019 mmol) in 4.8 mL of DMF was treated with a 1 M solution of K$_2$CO$_3$ (0.960 mL). The resulting yellow solution was heated at 120° C. for 45 min, and then diluted with EtOAc and H$_2$O. The layers were separated and the aqueous layer was extracted with EtOAc. The combined organic layers were washed with brine, dried over Na$_2$SO$_4$, filtered, and concentrated. Purification of the resulting residue by flash chromatography (0-25% EtOac/hexanes) afforded the desired compound as a white solid. LCMS: calculated for C$_{40}$H$_{34}$F$_2$N$_2$O$_3$ 628.71, observed m/e 629.1 (M+H)$^+$ (Rt 2.82/4 min).

Step C: Ethyl 3-{[5-(biphenyl-4-yl)-4,6-difluoro-1H-benzimidazol-2-yl]oxy}cyclo-pentanecarboxylate. To a solution of ethyl 3-{[5-(biphenyl-4-yl)-1-(biphenyl-4-ylmethyl)-4,6-difluoro-1H-benzimidazol-2-yl]oxy}cyclopentanecarboxylate (0.088 g, 0.140 mmol) and Pd(OH)$_2$ (0.026 g, 0.036 mmol) in 1.5 mL of EtOAc and 0.75 mL of EtOH was added 1,4-cyclohexadiene (0.337 mL, 3.60 mmol). The resulting black suspension was microwaved at 130° C. for 2 h, and then filtered through a Celite™ pad eluting with 100% EtOAc. The resulting filtrate was then concentrated in vacuo. Purification of the resulting residue by reverse phase Gilson™ HPLC (30-100% MeCN/H$_2$O) gave the title compound. LCMS: calculated for C$_{27}$H$_{24}$F$_2$N$_2$O$_3$ 462.49, observed m/e 462.9 (M+H)$^+$ 484.9 (M+Na) (Rt 2.45/4 min).

Step D: 3-{[5-(biphenyl-4-yl)-4,6-difluoro-1H-benzimidazol-2-yl]oxy}cyclo-pentanecarboxylic acid. Ethyl 3-{[5-(biphenyl-4-yl)-4,6-difluoro-1H-benzimidazol-2-yl]oxy}cyclopentanecarboxylate (0.039 g, 0.084 mmol) was dissolved in 1 mL of THF and treated with KOTMS (0.032 g, 0.253 mmol). The reaction mixture was stirred overnight at ambient temperature, and then diluted with EtOAc and washed with 2 N HCl. The layers were separated and the aqueous layer was further extracted with EtOAc. The combined organic layers were washed with brine, dried over Na$_2$SO$_4$, filtered, and concentrated to afford the title compound as a white solid. LCMS: calculated for C$_{25}$H$_{20}$F$_2$N$_2$O$_3$ 434.43, observed m/e 434.9 (M+H)$^+$ (Rt 2.24/4 min). $^1$H NMR (500 MHz, d6-DMSO): δ7.77 (d, 2H), 7.73 (d, 2H), 7.56-7.46 (m, 4H), 7.39 (m, 1H), 7.14 (d, 1H), 5.50 (m, 1H), 2.95 (m, 1H), 2.20-1.80 (m, 6H).

EXAMPLE 18

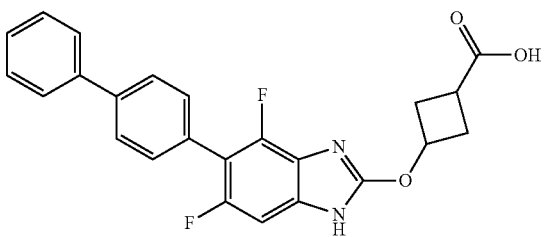 [SMILES: O=C(O)C1CC(Oc2nc3c(F)c(-c4ccc(-c5ccccc5)cc4)c(F)cc3[nH]2)C1]

3-{[5-(biphenyl-4-yl)-4,6-difluoro-1H-benzimidazol-2-yl]oxy}cyclobutanecarboxylic acid Step A: Ethyl 3-{[1-(biphenyl-4-ylmethyl)-4,6-difluoro-5-iodo-1H-benzimidazol-2-yl]oxy}cyclobutanecarboxylate. To a solution of 1-(biphenyl-4-ylmethyl)-4,6-difluoro-5-iodo-2-(methylsulfonyl)-1H-benzimidazole (Intermediate 5, 0.457 g, 0.872 mmol) and 3-hydroxy-cyclobutanecarboxylic acid ethyl ester (Intermediate 12, 0.503 g, 3.49 mmol) in 2.9 mL of DMF was added DBU (0.526 mL, 3.49 mmol) dropwise via syringe. The reaction was heated at 80° C. for 1 h, and then diluted with EtOAc and H$_2$O. The layers were separated and the aqueous layer was extracted with EtOAc. The combined organic layers were washed with brine, dried over Na$_2$SO$_4$, filtered, and concentrated. The resulting crude residue was purified on silica gel (eluted 2-15% then 15% then 15-20% EtOAc/hexanes: gradient elution) to give the desired product. LCMS: calculated for $C_{27}H_{23}F_2IN_2O_3$ 588.38, observed m/e 588.9 (M+H)+ (Rt 2.55/4 min).

Step B: Ethyl 3-{[5-(biphenyl-4-yl)-1-(biphenyl-4-ylmethyl)-4,6-difluoro-1H-benzimidazol-2-yl]oxy}cyclobutanecarboxylate. A solution of ethyl 3-{[1-(biphenyl-4-ylmethyl)-4,6-difluoro-5-iodo-1H-benzimidazol-2-yl]oxy}cyclobutanecarboxylate (0.350 g, 0.595 mmol), biphenylboronic acid (0.130 g, 0.654 mmol), and Pd(PPh$_3$)$_4$ (0.027 g, 0.024 mmol) in 6 mL of DMF was treated with a 1 M solution of K$_2$CO$_3$ (1.20 mL). The resulting yellow solution was heated at 120° C. for 45 min, and then diluted with EtOAc and H$_2$O. The layers were separated and the aqueous layer was extracted with EtOAc. The combined organic layers were washed with brine, dried over Na$_2$SO$_4$, filtered, and concentrated. Purification of the resulting residue by flash chromatography (0-15% then 15-20% then 20% EtOAc/hexanes) provided the desired product as a white solid. LCMS: calculated for $C_{39}H_{32}F_2N_2O_3$ 614.68, observed ink 615.1 (M+H)+ (Rt 2.79/4 min).

Step C: Ethyl 3-{[5-(biphenyl-4-yl)-4,6-difluoro-1H-benzimidazol-2-yl]oxy}cyclobutane carboxylate. To a solution of ethyl 3-{[5-(biphenyl-4-yl)-1-(biphenyl-4-ylmethyl)-4,6-difluoro-1H-benzimidazol-2-yl]oxy}cyclobutanecarboxylate (0.160 g, 0,260 mmol) and Pd(OH)$_2$ (0.048 g, 0.068 mmol) in 2.5 mL of EtOAc and 1.25 mL of EtOH was added 1,4-cyclohexadiene (0.630 mL, 6.70 mmol). The resulting black suspension was microwaved at 130° C. for 2 h. Then the reaction was filtered through a Celite™ pad, washed with 100% EtOAc, and the filtrate was concentrated in vacuo. Purification of the resulting residue by reverse phase Gilson™ HPLC (50-100% MeCN/H$_2$O) afforded the title compound as a white solid. LCMS: calculated for $C_{26}H_{22}F_2N_2O_3$ 448.46, observed m/e 449.0 (M+H)+ (Rt 2.27/4 min).

Step D: 3-{[5-(biphenyl-4-yl)-4,6-difluoro-1H-benzimidazol-2-yl]oxy}cyclo-butanecarboxylic acid. Ethyl 3-{[5-(biphenyl-4-yl)-4,6-difluoro-1H-benzimidazol-2-yl]oxy}cyclobutane carboxylate (0.046 g, 0.102 mmol) was dissolved in 1 mL of THF and treated with KOTMS (0.039 g, 0.308 mmol). The reaction mixture was stirred at ambient temperature overnight, and then diluted with EtOAc and washed with 2 N HCl. The aqueous layer was further extracted with EtOAc, and the combined organic layers were washed with brine, dried over Na$_2$SO$_4$, filtered, and concentrated to give the title compound. LCMS: calculated for $C_{24}H_{18}F_2N_2O_3$ 420.41, observed m/e 420.9 (M+H)+ (Rt 2.07/4 min). $^1$H NMR (500 MHz, d6-DMSO): δ7.77 (d, 2H), 7.73, (d, 2H), 7.55-7.47 (m, 4H), 7.39 (m, 1H), 7.15 (br, 1H), 5.23 (m, 1H), 2.82-2.70 (m, 2H), 2.32-2.25 (m, 2H), 1.98 (m, 1H).

EXAMPLE 19

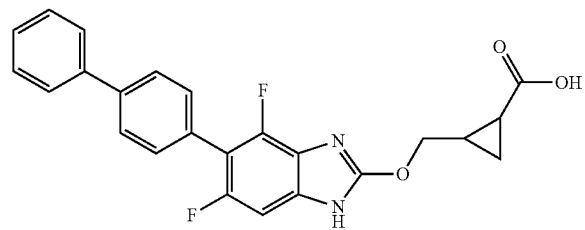 [SMILES: O=C(O)C1CC1COc1nc2c(F)c(-c3ccc(-c4ccccc4)cc3)c(F)cc2[nH]1]

2-({[5-(biphenyl-4-yl)-4,6-difluoro-1H-benzimidazol-2-yl]oxy}methyl)cyclopropane-carboxylic acid Step A: Ethyl 2-({[1-(biphenyl-4-ylmethyl)-4,6-difluoro-5-iodo-1H-benzimidazol-2-yl]oxy}methyl)cyclopropanecarboxylate. To a solution of 1-(biphenyl-4-ylmethyl)-4,6-difluoro-5-iodo-2-(methylsulfonyl)-1H-benzimidazole (Intermediate 5, 0.500 g, 0.954 mmol) and 2-hydroxymethyl-cyclopropanecarboxylic acid ethyl ester (Intermediate 10, 0.550 g, 3.81 mmol) in 3.2 mL of DMF was added DBU (0.575 mL, 3.81 mmol) dropwise via syringe. The reaction was heated at 80° C. for 2 h, and then diluted with EtOAc and H$_2$O. The layers were separated and the aqueous layer was extracted with EtOAc. The combined organic layers were washed with brine, dried over Na$_2$SO$_4$, filtered, and concentrated. The resulting crude residue was purified on silica gel (eluted 2-15% then 15-20% EtOAc/hexanes: gradient elution) to furnish the desired product. LCMS: calculated for $C_{27}H_{23}F_2IN_2O_3$ 588.38, observed m/e 588.9 (M+H)+ (Rt 2.51/4 min).

Step B: Ethyl 2-({[5-(biphenyl-4-yl)-1-(biphenyl-4-ylmethyl)-4,6-difluoro-1H-benzimidazol-2-yl]oxy}methyl)cyclopropanecarboxylate. A solution of Ethyl 2-({[1-(biphenyl-4-ylmethyl)-4,6-difluoro-5-iodo-1H-benzimidazol-2-yl]oxy}methyl)cyclo-propanecarboxylate (0.0440 g, 0.748 mmol), biphenylboronic acid (0.163 g, 0.823 mmol), and Pd(PPh$_3$)$_4$ (0.035 g, 0.030 mmol) in 7.5 mL of DMF was treated with a 1 M solution of K$_2$CO$_3$ (1.50 mL). The resulting yellow solution was heated at 120° C. for 45 min., and then diluted with EtOAc and H$_2$O. The layers were separated and the aqueous layer was extracted with EtOAc. The combined organic layers were washed with brine, dried over Na$_2$SO$_4$, filtered, and concentrated. Purification of the resulting residue by flash chromatography (0% then 0-20% then 20-30% EtOAc/hexanes) afforded the title compound as a white solid. LCMS: calculated for $C_{39}H_{32}F_2N_2O_3$ 614.68, observed m/e 615.1 (M+H)+ (Rt 2.78/4 min).

Step C: Ethyl 2-({[5-(biphenyl-4-yl)-4,6-difluoro-1H-benzimidazol-2-yl]oxy}methyl)cyclopropanecarboxylate. To a solution of ethyl 2-({[5-(biphenyl-4-yl)-1-(biphenyl-4-ylmethyl)-4,6-difluoro-1H-benzimidazol-2-yl]oxy}methyl)cyclopropanecarboxylate (0.270 g, 0.439 mmol) and Pd(OH)$_2$ (0.080 g, 0.114 mmol) in 3.6 mL of EtOAc and 1.8 mL of EtOH was added 1,4-cyclohexadiene (1.06 mL, 11.3 mmol). The resulting black suspension was microwaved at 130° C. for 2 h, and then filtered through a Celite™ pad, and washed with 100% EtOAc. The resulting filtrate was concentrated. Purification of the resulting crude product by reverse phase Gilson™ HPLC (50-100% AcCN/H$_2$O) afforded the desired product. LCMS: calculated for $C_{26}H_{22}F_2N_2O_3$ 448.46, observed m/e 448.9 (M+H)+ (Rt 2.37/4 min).

Step D: 2-({[5-(biphenyl-4-yl)-4,6-difluoro-1H-benzimidazol-2-yl]oxy}methyl)cyclopropanecarboxylic acid. Ethyl 2-({[5-(biphenyl-4-yl)-4,6-difluoro-1H-benzimidazol-2-yl]oxy}methyl)cyclopropanecarboxylate (0.046 g, 0.102 mmol) was dissolved in 1 mL of THF and treated with KOTMS (0.037 g, 0.288 mmol). The reaction mixture was stirred at ambient temperature overnight, and then diluted with EtOAc and washed with 2 N HCl. The acidic aqueous layer was separated and further extracted with EtOAc. The combined organic layers were washed with brine, dried over Na$_2$SO$_4$, filtered, and concentrated to give the title compound. LCMS: calculated for $C_{24}H_{18}F_2N_2O_3$ 420.41, observed m/e 420.9 (M+H)+ (Rt 2.21/4 min). $^1$H NMR (500 MHz, CD3OD): δ7.73-7.64 (m, 4H), 7.51 (d, 2H), 7.48-7.41 (m, 2H), 7.35 (m, 1H), 7.03 (d, 1H), 4.55 (dd, 1H), 4.29 (dd, 1H), 1.95 (m, 1H), 1.75 (m, 1H), 1.28 (m, 1H), 1.08 (m, 1H).

EXAMPLE 20

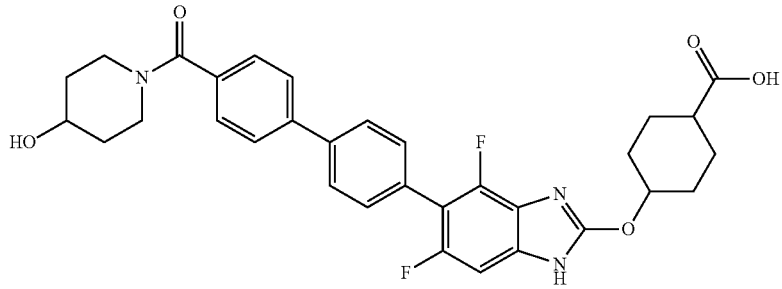 [SMILES: O=C(O)C1CCC(Oc2nc3c(F)c(-c4ccc(-c5ccc(C(=O)N6CCC(O)CC6)cc5)cc4)c(F)cc3[nH]2)CC1]

4-[(4,6-difluoro-5-{4'-[(4-hydroxypiperidin-1-yl)carbonyl]biphenyl-4-yl}-1H-benzimidazol-2-yl)oxy]cyclohexanecarboxylic acid Step A Ethyl 4-{[1-(biphenyl-4-ylmethyl)-5-(4-bromophenyl)-4,6-difluoro-1H-benzimidazol-2-yl]oxy}cyclohexanecarboxylate. The title compound was prepared from 1-(biphenyl-4-ylmethyl)-4,6-difluoro-5-iodo-2-(methylsulfonyl)-1H-benzimidazole (Intermediate 5) according to the procedure described in Example 5, Steps A and B by employing ethyl 4-hydroxycyclohexane carboxylate in place of 3-hydroxy-cyclobutane-carboxylic acid ethyl ester (in Step A). Purification of the crude product by flash chromatography (15-20% EtOAc/hexanes) afforded the title compound.

Step B Ethyl 4-{[1-(biphenyl-4-ylmethyl)-4,6-difluoro-5-{4'-[(4-hydroxypiperidin-1-yl)carbonyl]biphenyl-4-yl}-1H-benzimidazol-2-yl]oxy}cyclohexanecarboxylate. To a yellow solution of (4-hydroxypiperidin-1-yl)[4-(4,4,5,5-tetramethyl-1,3,2-dioxaborolan-2-yl)phenyl]methanone (0.147 g, 0.443 mmol), ethyl 4-{[1-(biphenyl-4-ylmethyl)-5-(4-bromophenyl)-4,6-difluoro-1H-benzimidazol-2-yl]oxy}cyclohexane-carboxylate (0.260 g, 0.403 mmol), and Pd(PPh$_3$)$_4$ (0.028 g, 0.024 mmol) was added 1 M K$_2$CO$_3$ (1.20 mL, 1.20 mmol) dropwise via syringe. The mixture was heated at 120° C. for 45 min, and then diluted with EtOAc and H$_2$O. The aqueous layer was separated and further extracted with EtOAc. The combined organic layers were washed with brine, dried over Na$_2$SO$_4$, filtered, and concentrated. Purification of the resulting residue by flash chromatography (100% EtOAc) afforded the desired compound as a ~2:1 mixture of trans/cis isomers. The cis/trans isomers were separated via reverse phase Gilson™ HPLC (60-100% MeCN/H$_2$O) to afford a faster eluting isomer A and a slower eluting isomer B as white solids.

Step C 4-[(4,6-difluoro-5-{4'-[(4-hydroxypiperidin-1-yl)carbonyl]biphenyl-4-yl}-1H-benzimidazol-2-yl)oxy]cyclohexanecarboxylic acid. To a solution of ethyl 4-{[1-(biphenyl-4-ylmethyl)-4,6-difluoro-5-{4'-[(4-hydroxypiperidin-1-yl)carbonyl]biphenyl-4-yl}-1H-benzimidazol-2-yl]oxy}cyclohexanecarboxylate (isomer B, 0.057 g, 0.074 mmol) and Pd(OH)$_2$ (0.014 g, 0.019 mmol) in 0.8 mL of EtOAc and 0.4 mL of EtOH was added 1,4-cyclohexadiene (0.180 mL, 1.91 mmol). The resulting black suspension was microwaved at 130° C. for 2 h, then filtered through a Celite™ pad, and washed with EtOAc. The resulting filtrate was concentrated in vacuo to give a crude residue. The crude residue was dissolved in 2 mL of THF and treated with KOTMS (0.028 g, 0.222 mmol). The reaction mixture was stirred for 18 h at ambient temperature, and then concentrated. The resulting crude residue was purified by reverse phase Gilson™ HPLC (35-100% MeCN/H$_2$O) to provide the title compound as a white solid. LCMS: calculated for C$_{32}$H$_{31}$F$_2$N$_3$O$_5$ 575.60, observed m/e 576.1 (M+H)$^+$ (Rt 1.99/4 min). $^1$H NMR (500 MHz, CD3OD): 7.80 (d, 2H), 7.76 (d, 2H), 7.55 (d, 2H), 7.52 (d, 2H), 7.05 (d, 1H), 4.98-4.90 (m, 1H), 4.27-4.16 (m, 1H), 3.95-3.86 (m, 1H), 3.79-3.67 (m, 1H), 3.42-3.33 (m, 1H), 2.43-2.34 (m, 1H), 2.34-2.26 (m, 2H), 2.16-2.06 (m, 2H), 2.03-1.90 (m, 2H), 1.90-1.78 (m, 2H), 1.75-1.42 (m, 5H).

EXAMPLE 21

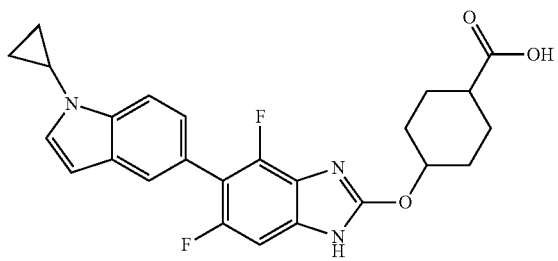 [SMILES: O=C(O)C1CCC(Oc2nc3c(F)c(-c4ccc5c(ccn5C5CC5)c4)c(F)cc3[nH]2)CC1]

4-{[5-(1-Cyclopropyl-1H-indol-5-yl)-4,6-difluoro-1H-benzimidazol-2-yl]oxy}cyclohexanecarboxylic acid Step A Ethyl 4-{[1-(biphenyl-4-ylmethyl)-4,6-difluoro-5-(1H-indol-5-yl)-1H-benzimidazol-2-yl]oxy}cyclohexanecarboxylate. To a yellow solution of 5-indoleboronic acid pinacol ester (0.232 g, 0.954 mmol), ethyl 4-{[1-(biphenyl-4-ylmethyl)-4,6-difluoro-5-iodo-1H-benzimidazol-2-yl]oxy}cyclohexanecarboxylate (0.490 g, 0.795 mmol) and Pd(PPh$_3$)$_4$ (0.055 g, 0.048 mmol) in. DMF (8 mL) was added 1 M K$_2$CO$_3$ (2.4 mL, 2.4 mmol) dropwise via syringe. The mixture was heated at 120° C. for 40 min, and then diluted with EtOAc and H$_2$O. The layers were separated and the aqueous layer was further extracted with EtOAc. The combined organic layers were washed with brine, dried over Na$_2$SO$_4$, filtered, and concentrated. Purification of the resulting residue via preparative TLC using 30% EtOAc/hexanes afforded the desired compound. LCMS: calculated for C$_{37}$H$_{33}$F$_2$N$_3$O$_3$ 605.67, observed m/e 606.1 (M+H)$^+$629.0 (M+Na) (Rt 2.80/4 min).

Step B Ethyl 4-{[1-(biphenyl-4-ylmethyl)-5-(1-cyclopropyl-1H-indol-5-yl)-4,6-difluoro-1H-benzimidazol-2-yl]

oxy}cyclohexanecarboxylate. A 10 mL flask was charged with ethyl 4-{[1-(biphenyl-4-ylmethyl)-4,6-difluoro-5-(1H-indol-5-yl)-1H-benzimidazol-2-yl]oxy}cyclohexanecarboxylate (0.080 g, 0.132 mmol), DMAP (0.048 g, 0.396 mmol), cyclopropylboronic acid (0.023 g, 0.264 mmol), and Cu(OAc)$_2$ (4.8 mg, 0.026 mmol) under a nitrogen atmosphere. Toluene (1.3 mL) was added and the resulting suspension was treated with a 0.6 M solution of NaHMDS in toluene (0.220 mL, 0.132 mmol) dropwise via syringe. Dry air was purged into the reaction vessel, and the reaction was heated at 95° C. overnight. The dark reaction mixture was then cooled to ambient temperature and treated with 20 mL of 1 N HCl. The aqueous layer was separated and extracted with EtOAc (2×25 mL). The combined organic layers were washed with brine, dried over Na$_2$SO$_4$, filtered, and concentrated. Purification of the resulting crude residue by preparative TLC (25% EtOAc/hexanes) furnished the title compound as a pale yellow residue. LCMS: calculated for C$_{40}$H$_{37}$F$_2$N$_3$O$_3$ 645.74, observed rule 646.2 (M+H)$^+$ (Rt 3.03/4 min).

Step C Ethyl 4-{[5-(1-cyclopropyl-1H-indol-5-yl)-4,6-difluoro-1H-benzimidazol-2-yl]oxy}cyclohexanecarboxylate. To a solution of ethyl 4-{[1-(biphenyl-4-ylmethyl)-5-(1-cyclopropyl-1H-indol-5-yl)-4,6-difluoro-1H-benzimidazol-2-yl]oxy}cyclohexane-carboxylate (0.080 g, 0.124 mmol) and Pd(OH)$_2$ (0.023 g, 0.032 mmol) in 1.65 mL of EtOAc and 0.83 mL of EtOH was added 1,4-cyclohexadiene (0.300 mL, 3.19 mmol). The resulting black suspension was microwaved at 130° C. for 2 h, then filtered through a Celite™ pad, and washed with 100% EtOAc. The resulting filtrate was concentrated in vacuo. Purification of the resulting crude residue by preparative TLC (40% EtOAc/hexanes) afforded the title compound. LCMS: calculated for C$_{27}$H$_{27}$F$_2$N$_3$O$_3$ 479.52, observed m/e 480.1 (M+11)$^+$ (Rt 2.58/4 min).

Step D 4-{[5-(1-Cyclopropyl-1H-indol-5-yl)-4,6-difluoro-1H-benzimidazol-2-yl]oxy}cyclohexanecarboxylic acid. Ethyl 4-{[5-(1-cyclopropyl-1H-indol-5-yl)-4,6-difluoro-1H-benzimidazol-2-yl]oxy}cyclohexanecarboxylate (0.046 g, 0.96 mmol) was dissolved in 1 mL of THF and treated with 37 mg of KOTMS (0.037 g, 0.288 mmol). The reaction mixture was stirred at ambient temperature overnight. The mixture was then diluted with EtOAc and washed with 2 N HCl. The aqueous layer was separated and further extracted with EtOAc. The combined organic layers were washed with brine, dried over Na$_2$SO$_4$, filtered, and concentrated to give the title compound. LCMS: calculated for C$_{25}$H$_{23}$F$_2$N$_3$O$_3$ 451.46, observed m/e 451.92 (MAI)$^+$ (Rt 2.42/4 min). $^1$H NMR (500 MHz, CD3OD): δ7.62 (d, 1H), 7.56 (brs, 1H), 7.25-7.20 (m, 2H), 7.00-6.92 (br, 1H), 6.42 (d, 1H), 4.92 (m, 1H), 3.41 (m, 1H), 2.37 (m, 1H), 2.34-2.27 (m, 2H), 2.15-2.07 (m, 2H), 1.73-1.55 (m, 4H), 1.13-1.08 (m, 2H), 1.03-0.98 (m, 2H).

Examples 22-24 in Table 2 were prepared following the procedures described in Example 5, Steps A, B, and C by using 1-(biphenyl-4-ylmethyl)-4,6-difluoro-5-iodo-2-(methylsulfonyl)-1H-benzimidazole (Intermediate 5) and by substituting the appropriate boronic acid or boronate ester from the Intermediates, or from commercial sources; and by substituting the appropriate cycloalkanols from the Intermediates, or from commercial sources. Examples 25-26 were similarly prepared following Example 5, Steps A, B, and C from Intermediate 7 and employing the deprotection strategy outlined in Example 6, Step B.

TABLE 2

Compounds prepared according to the methods described in Examples 5 and 6.

| Example Number | Structure | HPLC-mass spectrum m/e |
|---|---|---|
| 22 | 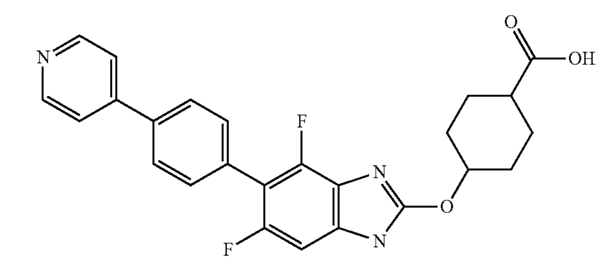 [SMILES: O=C(O)C1CCC(Oc2nc3c(F)c(-c4ccc(-c5ccncc5)cc4)c(F)cc3[nH]2)CC1] | 450.1 |
| 23 | 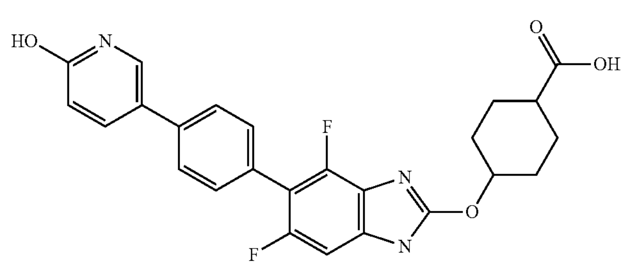 [SMILES: O=C(O)C1CCC(Oc2nc3c(F)c(-c4ccc(-c5ccc(O)nc5)cc4)c(F)cc3[nH]2)CC1] | 466.0 |

TABLE 2-continued

Compounds prepared according to the methods described in Examples 5 and 6.

| Example Number | Structure | HPLC-mass spectrum m/e |
|---|---|---|
| 24 | 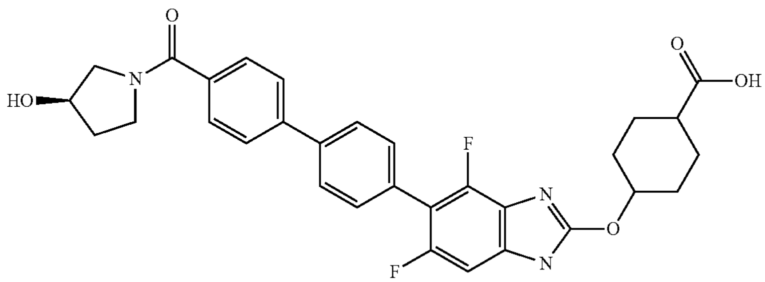 [SMILES: O=C(O)C1CCC(Oc2nc3c(F)c(-c4ccc(-c5ccc(C(=O)N6CC[C@@H](O)C6)cc5)cc4)c(F)cc3[nH]2)CC1] | 562.1 |
| 25 | 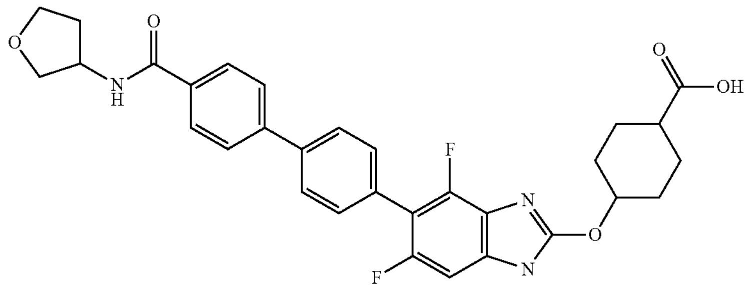 [SMILES: O=C(NC1CCOC1)c1ccc(-c2ccc(-c3c(F)cc4[nH]c(OC5CCC(C(=O)O)CC5)nc4c3F)cc2)cc1] | 562.2 |
| 26 | 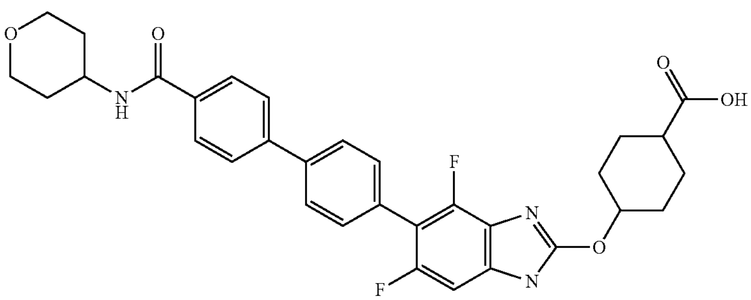 [SMILES: O=C(NC1CCOCC1)c1ccc(-c2ccc(-c3c(F)cc4[nH]c(OC5CCC(C(=O)O)CC5)nc4c3F)cc2)cc1] | 576.2 |

BIOLOGICAL EXAMPLE 1

AMPKSAMSF (in vitro AMPK Activation Assay)

The recombinant human AMPK complex 1 (containing α1β1γ1) was obtained from baculovirus expression system. Recombinant viruses were generated by cotransfection of AMPK/pBacPak9 clones with Baculogold baculovirus DNA (Pharmingen) in *spodoptera frugiperda* 21 cells according to the manufacturer's instructions. Each round of virus amplification was performed for 5 days in Grace's medium containing 10% serum. Virus that had been subjected to three rounds of amplification was used for all protein production procedures. To express the AMPK complex, sf21 cells were adapted to serum free medium (SF900 II, Invitrogen) by sequential dilution from serum containing stocks into SF900II medium and maintained in shaker flasks at 90 rpm at 27° C. The recombinant AMPK enzyme complex was produced by triple infection, one recombinant virus for each of the subunits, in sf21 cells under serum free conditions. Cells were infected in log phase, $1 \times 10^6$ cells/ml, at a multiplicity of infection of Cells were harvested by centrifugation at 10,000×g for 15 minutes after 72 hours of infection with viruses. The insect cell pellet from 2 liters of culture was resuspended in 50 ml lysis buffer (20 mM Tris-HCl, 50 mM NaCl, 50 mM NaF, 30 mM Na PPi, 0.25 M sucrose, 10 mM $ZnCl_2$, 2 mM DTT, 0.4 mg/ml digitonin) and subjected to two cycles of freeze-thaw lysis in a dry-ice ethanol bath. Insoluble material was removed by centrifugation at 10,000×g and the supernatant was fractionated with use of polyethylene glycol (PEG). The protein fraction precipitating between 2.5 and 6% PEG was used for further purification using a Blue-Sepharose step (Zhou et al, *J. Clin. Invest.* 108, 1167-1174, 2001).

The in vitro AMPK activation assay is performed in a volume of 30 µl in a 384-well plate. Enzyme reactions were assembled in the microtiter plate by adding 15 µl of 2× enzyme in assay buffer (20 mM HEPES, pH 7.3, 5 mM $MgCl_2$, 3 mM DTT, 0.01% Brij 35 and CamK Kinase, to activate AMPK) to wells which contained either DMSO or compound. The reaction was initiated with the addition of 15 p. 12× substrate mixture containing 200 µM ATP, and 3.0 µM fluorescently labeled SAMS (5-FAM-HMRSAMS-GLHLVKRR-COOH) in assay buffer. After 45-minute incubation at 25° C., the reaction was stopped by the addition of 70 µl stop buffer (100 mM HEPES, pH 7.3, 40 mM EDTA, 0.015% Brij 35). Phosphorylated 5-FAM SAMS product is assessed using a Caliper EZ Reader LabChip microfluidics reader. Product conversion is determined by calculating the peak heights of the substrate and product and reporting the product/(product+substrate) peak ratio. The 10-point titration data were expressed as maximum AMP activation. The results were plotted using 4 parameter fit and the inflection point reflecting 50% of the maximum activation was reported as the $EC_{50}$. The % maximum AMP activation for selected compounds is provided in the table below.

The compounds of present invention, including the compounds of Examples 1-26, were tested in the in vitro AMPK activation assay using recombinant human AMPK complex 1 (containing α1β1γ1) and found to have greater than 50% maximum AMP activation of human AMPK complex 1 (containing α1β1γ1), and $EC_{50}$ values of less than 10 micromolar. Preferred compounds of the present invention were found to have $EC_{50}$ values of less than 0.1 micromolar in the in vitro AMPK activation assay using recombinant human AMPK complex 1.

Maximum AMP Activation for Selected Compounds

| Example No. | % Maximum AMP Activation of human AMPK Complex 1 | $EC_{50}$ (nM) |
|---|---|---|
| 15 | 653 | 10 |
| 16 | 617 | 6 |
| 17 | 593 | 13 |
| 18 | 538 | 14 |
| 19 | 631 | 17 |
| 20 | 642 | 10 |
| 21 | 504 | 4 |

BIOLOGICAL EXAMPLE 2

Phosphoroylation of Acetyl CoA Carboxylase by AMPK Activators in db/+ Mice:

To assess the potential for AMPK activators to increase the phosphorylation of Acetyl COA Carboxylase (ACC) in liver and skeletal muscle, db/+ mice were dosed with AMPK activators at either 2 or 7 h prior to evaluation where phosphorylated ACC (p-ACC)/total ACC levels were compared in the tissues of vehicle and compound treated mice. Briefly, mice were anesthetized using gas anesthesia with 1-4% isoflurane administered to effect via nose cone. Once anesthetized, samples of liver and skeletal muscle (gastrocnemius) are removed, snap frozen in liquid nitrogen, and homogenized. Homogenates are analyzed for protein concentration and equal amounts of protein are assayed for total and phosphorylated ACC (p-ACC) levels using Meso Scale Discovery's Multi-array assay kit. MSD assay plates contain an electrode surface that is coated with streptavidin. Protein sample binds to streptavidin. The primary ACC or p-ACC specific antibody binds to protein and a secondary antibody labeled with MSD SULFO-TAG then binds to the primary antibody. The electrode surface of the MSD plate responds to an electrical stimulus and causes the SULFO-TAG labels bound to ACC and p-ACC to emit a light signal in proportion to the amount of p-ACC or total ACC present. The ratio of p-ACC/total ACC levels are determined for each sample and the ratio of p-ACC/total ACC levels for mice treated with AMPK activators is significantly elevated compared to the ratio of those treated with the vehicle control (significant elevations are described as differences where p<0.05).

BIOLOGICAL EXAMPLE 3

Inhibition of Fatty Acid Synthesis (FAS) by AMPK Activators in db/+ Mice:

To determine the effect of AMPK activators on Fatty Acid Synthesis (FAS) in the liver, the effect of oral pre-dosing of compounds on the amount of $^3H$ incorporated into hepatic triglyceride is determined as described by Sakurai T, Miyazawa S, Shindo Y, and T. Hashimoto (Biochim Biophys Acta. 1974 Sep. 19; 360 (3):275-88). Briefly, mice (db/+, Jackson Laboratory, Maine) are orally dosed with AMPK activators at time=−8 h. Then at time=−1 h, mice are injected with 0.5 ml of 0.15 M NaCl containing 0.2 mCi of $^3H$ water per 100 g of body weight. At time 0, mice are sacrificed via cervical dislocation and livers are harvested for FAS analysis. To analyze livers for FAS, samples of liver are heated at 90° C. for 5 hours in a 4 M KOH/50% ethanol solution. Then the alkaline hydrolysate of liver is extracted with hexane and acidified to a pH<2 with 10 M $H_2SO_4$. The fatty acids of liver, are then extracted from acidified hydrolysate with additional hexane, dried down with a stream of warm air, then re-suspended in scintillation fluid, and counted on a beta counter. The amount of fatty acids synthesized per gram of liver is calculated based on the amount of $^3H$ incorporated into hepatic triglyceride. The amount of $^3H$ radiolabelled fatty acids synthesized in mice with treated with an AMPK activator is significantly less than the amount of $^3H$ radiolabelled fatty acids synthesized in the control mice.

BIOLOGICAL EXAMPLE 4

In Vivo Study for Therapy with an AMPK Activator in Mice (Glucose Tolerance Test):

DIO mice are treated simultaneously with an effective dose of an AMPK-activated protein kinase activator.

Materials and Methods: Male C57BL/6NT mice (Taconic, 16-18 weeks old at the beginning of the drug administration) are used. Mice are given water and high fat diet D12492 (Research Diet Inc.) ad libitum. They are kept in an animal room which is maintained at 23±2 C temperature, 55±15% relative humidity and on a 12-hr light-dark cycle (7:00-19:00) during a quarantine and acclimatization period of 1 week. Animals are then administered vehicle (5 ml/kg of 0.5% methylcellulose in distilled water) by oral gavage twice-daily at 9 AM and 5 PM. After 9 days, stable body weight is observed. The following day (day −1), the mice are fasted for 4 hours and tail bled to determine the glucose and insulin levels. Animals are sorted into groups based on plasma glucose, insulin levels and body weight (n=8). The body weight and food in the hopper are recorded on day 0 before compound dosing is initiated. One of the groups is orally administered vehicle while the second group is administered an AMPK-activated protein kinase activator of the present invention at a dose of 30 mg/kg (5 ml/kg) twice-daily for 12 days by gavage. Body weight and food intake are measured every other day. On day 5, the animals are fasted 4 hours for measuring plasma glucose and insulin levels after morning dosing. At day 12, body weight and food intake are measured and animals receive their last morning dose. Mice again are fasted 4 hours, blood is collected at a set time point (t=0 min), and then challenged with dextrose orally (2 g/kg) Plasma glucose and insulin levels are determined from tail bleeds taken at 20 and 90 minutes after dextrose challenge. The plasma glucose and insulin excursion profile from t=0 to t=90 min is used to integrate an area under the curve (AUC) for each treatment. Percent inhibition values for each treatment are generated from the AUC data normalized to the C57BL/6NT mice feed with D7012. Preferred compounds of the present invention significantly reduce day 12 glucose and/or insulin AUC during the Oral Glucose Tolerance Test after an oral dose in the range of 0.1 to 100 mg/kg.

BIOLOGICAL EXAMPLE 5

Acute Food Intake Studies in Diet Induced Obese (DIO) Mice: General Procedure

Adult DIO mice are used in these studies. After at least 2 days of acclimation to the vivarium conditions (controlled humidity and temperature, lights on for 12 hours out of 24 hours) food (D12492 (Research Diet Inc.) is removed from rodent cages. An AMPK activator of the present invention or the vehicle is administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the AMPK activator is compared to the effect of the vehicle. The food intake of mice treated with an AMPK activator is significantly less than the food intake of control mice.

BIOLOGICAL EXAMPLE 6

Chronic Weight Reduction Studies in Diet Induced Obese (DIO) Mice: General Procedure Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

While the invention has been described and illustrated with reference to certain particular embodiments thereof, those skilled in the art will appreciate that various changes, modifications and substitutions can be made therein without departing from the spirit and scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

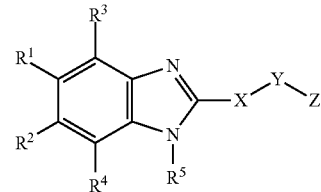

(I)

or a pharmaceutically acceptable salt thereof, wherein:
X is selected from:
(1) —O—,
(2) —O—$CH_2$—,
(3) —S—,
(4) —S—$CH_2$—,
(5) —$NR^d$—,
(6) —$NR^d$—$CH_2$—,
(7) —$CH_2$—, and
(8) —$CH_2$—$CH_2$—,
wherein each $CH_2$ is unsubstituted or substituted with 1 or 2 substituents selected from: hydroxy, halogen, —$C_{1-6}$alkyl, —$CO_2C_{1-6}$alkyl, and —$COC_{1-6}$alkyl;
Y is selected from:
(1) —$C_{3-7}$cycloalkyl, and
(2) —$C_{3-6}$cycloheteroalkyl,
wherein cycloalkyl and cycloheteroalkyl are unsubstituted or substituted with 1, 2, 3 or 4 substituents selected from $R^b$;
Z is selected from:
(1) —$(CH_2)_n CO_2 H$,
(2) —$(CH_2)_n CO_2 R^i$,
(3) —$(CH_2)_n NHCOR^i$,
(4) —$(CH_2)_n SO_2 NHC(O)R^i$,
(5) —$(CF_{12})_n NHSO_2 R^i$,
(6) —$(CH_2)_n C(O)NHSO_2 R^i$,
(7) heteroaryl, and
(8) —$C_{2-10}$cycloheteroalkyl,
wherein each $CH_2$ is unsubstituted or substituted with 1 or 2 substituents selected from $C_{1-6}$alkyl, and —OH, and wherein each cycloheteroalkyl and heteroaryl is unsubstituted or substituted with 1, 2, 3 or 4 substituents selected from $R^c$;
each $R^1$ and $R^2$ is independently selected from:
(1) halogen,
(2) —$(CH_2)_p$aryl,
(3) biphenyl, and
(4) —$(CH_2)_p$heteroaryl,
wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, and wherein each biphenyl, aryl and heteroaryl is unsubstituted or substituted with 1, 2, 3 or 4 substituents independently selected from $R^a$, provided that one and only one of $R^1$ and $R^2$ is halogen;
$R^3$ and $R^4$ are each independently selected from:
(1) hydrogen,
(2) halogen,
(3) —$C_{1-6}$alkyl,
(4) —$C_{2-6}$alkenyl,
(5) —$C_{2-6}$alkynyl,
(6) —CN,
(7) —$CF_3$,
(8) —$OC_{1-6}$alkyl,
(9) —$SO_2C_{1-6}$alkyl,

(10) —SO$_2$NHC$_{1-6}$alkyl, and
(11) —C(O)NHC$_{1-6}$alkyl,
wherein each alkyl is unsubstituted or substituted with 1, 2 or 3 halogens;

R$^5$ is selected from:
(1) hydrogen,
(2) —C$_{1-6}$alkyl,
(3) —CH$_2$CO$_2$H, and
(4) —CH$_2$CO$_2$C$_{1-6}$alkyl;

each R$^a$ is independently selected from the group consisting of:
(1) hydrogen,
(2) halogen,
(3) —(CH$_2$)$_m$OH,
(4) —(CH$_2$)$_m$N(R$^j$)$_2$,
(5) —(CH$_2$)$_m$CN,
(6) —C$_{1-6}$alkyl,
(7) —(CH$_2$)$_m$CF$_3$,
(8) —(CH$_2$)$_m$OCF$_3$,
(9) —(CF$_{12}$)$_m$SC$_{1-6}$alkyl,
(10) —(CH$_2$)$_m$S(O)$_2$C$_{1-6}$alkyl,
(11) —(CH$_2$)$_m$S(O)$_2$N(C$_{1-6}$alkyl)$_2$,
(12) —(CH$_2$)$_m$C(O)N(R$^j$)$_2$,
(13) —(CH$_2$)$_m$N(R$^j$)C(O)R$^f$,
(14) —(CH$_2$)$_m$C(O)R$^f$,
(15) —(CH$_2$)$_m$CO$_2$R$^f$,
(16) —(CH$_2$)$_m$OC(O)R$^f$,
(17) —(CH$_2$)$_m$C$_{3-7}$cycloalkyl,
(18) —(CH$_2$)$_m$C$_{3-7}$cycloalkenyl,
(19) —(CH$_2$)$_m$C$_{2-6}$cycloheteroalkyl,
(20) —(CH$_2$)$_m$C$_{2-6}$cycloheteroalkenyl,
(21) —(CH$_2$)$_m$aryl, and
(22) —(CH$_2$)$_m$heteroaryl, wherein each CH$_2$ is unsubstituted or substituted with 1 or 2 substituents selected from: oxo, —(CH$_2$)$_{0-3}$OH, —CN, —C$_{1-6}$ alkyl, —OC$_{1-6}$alkyl, halogen, —CH$_2$F, —CHF$_2$, —CF$_3$, and —CO$_2$C$_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —(CH$_2$)$_{0-3}$OH, —CN, —C$_{1-6}$ alkyl, —OC$_{1-6}$alkyl, halogen, —CH$_2$F, —CHF$_2$, —CF$_3$, and —CO$_2$C$_{1-6}$alkyl;

each R$^b$ is independently selected from:
(1) hydrogen,
(2) —C$_{1-6}$alkyl,
(3) aryl,
(4) heteroaryl,
(5) —C$_{3-6}$cycloalkyl,
(6) —C$_{3-6}$cycloalkenyl,
(7) —C$_{3-6}$cycloheteroalkyl,
(8) halogen,
(9) —OH,
(10) —OC$_{1-6}$alkyl,
(11) —CF$_3$,
(12) —CN, and
(13) —SO$_2$C$_{1-6}$alkyl, wherein each alkyl, aryl, heteroaryl, cycloalkyl, cycloalkenyl and cycloheteroalkyl is unsubstituted or substituted with 1, 2 or 3 halogens;

each R$^c$ is independently selected from:
(1) hydrogen,
(2) halogen,
(3) oxo,
(4) —(CH$_2$)$_r$OH,
(5) —(CH$_2$)$_r$N(R$^e$)$_2$,
(6) —(CH$_2$)$_r$CN,
(7) —C$_{1-6}$alkyl,
(8) —CF$_3$,
(9) —(CH$_2$)$_r$C$_{3-7}$cycloalkyl, and
(10) —(CH$_2$)$_r$C$_{2-6}$cycloheteroalkyl, wherein each CH$_2$ is unsubstituted or substituted with 1 or 2 substituents selected from: oxo, —OH, —CN, —C$_{1-6}$alkyl, —OC$_{1-6}$alkyl, halogen, —CH$_2$F, —CHF$_2$, and —CF$_3$, and wherein alkyl, cycloalkyl, and cycloheteroalkyl are unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$;

each R$^d$ is independently selected from:
(1) hydrogen, and
(2) C$_{1-6}$alkyl;

each R$^e$ is independently selected from:
(1) hydrogen, and
(2) C$_{1-6}$alkyl, wherein alkyl is unsubstituted or substituted with 1, 2, 3 or 4 substituents selected from: —OH, oxo, halogen, C$_{1-6}$alkyl, and —OC$_{1-6}$alkyl;

each R$^f$ is independently selected from:
(1) C$_{1-6}$alkyl,
(2) C$_{4-7}$cycloalkyl,
(3) C$_{4-7}$cycloalkenyl,
(4) C$_{3-7}$cycloheteroalkyl,
(5) C$_{3-7}$cycloheteroalkenyl,
(6) aryl, and
(7) heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —C$_{1-6}$alkyl, —OC$_{1-6}$alkyl, halogen, —CH$_2$F, —CHF$_2$, and —CF$_3$;

each R$^i$ is independently selected from:
(1) hydrogen,
(2) C$_{1-6}$alkyl,
(3) C$_{4-7}$cycloalkyl,
(4) C$_{4-7}$cycloalkenyl,
(5) C$_{3-7}$cycloheteroalkyl,
(6) C$_{3-7}$cycloheteroalkenyl,
(7) aryl, and
(8) heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —OCOC$_{1-6}$alkyl, and —OCO$_2$C$_{1-6}$alkyl;

each R$^j$ is independently selected from:
(1) hydrogen,
(2) —C$_{1-6}$alkyl,
(3) —C$_{3-6}$cycloalkyl, and
(4) —C$_{3-6}$cycloheteroalkyl, wherein alkyl, cycloalkyl and cycloheteroalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

n is 0, 1, 2, 3 or 4;
m is 0, 1, 2, 3 or 4;
p is 0, 1, 2, or 3; and
r is 0, 1 or 2.

2. The compound according to claim 1, wherein X is selected from:
(1) —O—, and
(2) —O—CH$_2$—, wherein each CH₂ is unsubstituted or substituted with 1 or 2 substituents selected from: hydroxy, halogen, —C$_{1-6}$alkyl, —CO$_2$C$_{1-6}$alkyl, and —COC$_{1-6}$alkyl; or a pharmaceutically acceptable salt thereof.

3. The compound according to claim 1, wherein R¹ is independently selected from:
(1) phenyl,
(2) biphenyl, and
(3) heteroaryl,
wherein each phenyl, biphenyl and heteroaryl is unsubstituted or substituted with 1, 2, 3 or 4 substituents independently selected from R$^a$; or a pharmaceutically acceptable salt thereof.

4. The compound according to claim 1, wherein R¹ is biphenyl, wherein biphenyl is unsubstituted or substituted with 1, 2 or 3 substituents independently selected from R$^a$; or a pharmaceutically acceptable salt thereof.

5. The compound according to claim 4, wherein R² is halogen; or a pharmaceutically acceptable salt thereof.

6. The compound according to claim 1, wherein Y is —C$_{3-7}$ cycloalkyl, wherein cycloalkyl is unsubstituted or substituted with 1, 2, 3 or 4 substituents selected from R$^b$; or a pharmaceutically acceptable salt thereof.

7. The compound according to claim 6, wherein Y is selected from the group consisting of:
(1) cyclopropyl,
(2) cyclobutyl,
(3) cyclopentyl, and
(4) cyclohexyl,
wherein each cyclopropyl, cyclobutyl, cyclopentyl, and cyclohexyl is unsubstituted or substituted with 1, 2 or 3 substituents selected from R$^b$; or a pharmaceutically acceptable salt thereof.

8. The compound according to claim 7, wherein Y is selected from the group consisting of:
(1) cyclohexyl, and
(2) cyclobutyl,
wherein each cyclohexyl and cyclobutyl is unsubstituted or substituted with 1, 2 or 3 substituents selected from R$^b$; or a pharmaceutically acceptable salt thereof.

9. The compound according to claim 1, wherein RS is hydrogen;
or a pharmaceutically acceptable salt thereof.

10. The compound according to claim 1, wherein Z is selected from the group consisting of:
(1) —(CH$_2$)$_n$CO$_2$H,
(2) —(CH$_2$)$_n$NHCOR$^i$,
(3) —(CH$_2$)$_n$NHSO$_2$R$^i$,
(4) —(CH$_2$)$_n$C(O)NHSO$_2$R$^i$,
(5) heteroaryl, and
(6) —C$_{2-10}$cycloheteroalkyl,
wherein each CH$_2$ is unsubstituted or substituted with 1 or 2 substituents selected from C$_{1-6}$alkyl, and —OH, and wherein each cycloheteroalkyl and heteroaryl is unsubstituted or substituted with 1, 2, 3 or 4 substituents selected from R$^c$; or a pharmaceutically acceptable salt thereof.

11. The compound according to claim 10, wherein Z is —CO$_2$H; or a pharmaceutically acceptable salt thereof.

12. The compound according to claim 1, wherein R³ and R⁴ are each independently selected from:
(1) hydrogen, and
(2) halogen;
or a pharmaceutically acceptable salt thereof.

13. The compound according to claim 12, wherein R³ is hydrogen or halogen, and R⁴ is hydrogen; or a pharmaceutically acceptable salt thereof.

14. The compound according to claim 1 wherein:
X is selected from:
(1) —O—, and
(2) —O—CH$_2$—;
Y is selected from the group consisting of:
(1) cyclopropyl,
(2) cyclobutyl,
(3) cyclopentyl, and
(4) cyclohexyl,
wherein each cyclopropyl, cyclobutyl, cyclopentyl, and cyclohexyl is unsubstituted or substituted with 1, 2 or 3 substituents selected from R$^b$;
Z is —CO$_2$H;
R¹ is independently selected from:
(1) phenyl,
(2) biphenyl, and
(3) heteroaryl,
wherein each phenyl, biphenyl and heteroaryl is unsubstituted or substituted with 1, 2, 3 or 4 substituents independently selected from R$^a$;
R² is halogen;
R³ and R⁴ are each independently selected from:
(1) hydrogen, and
(2) halogen; and
R⁵ is hydrogen;
or a pharmaceutically acceptable salt thereof.

15. The compound according to claim 1 wherein:
X is selected from:
(1) —O—, and
(2) —O—CH$_2$—;
Y is selected from the group consisting of:
(1) cyclohexyl, and
(2) cyclobutyl,
wherein each cyclohexyl and cyclobutyl is unsubstituted or substituted with 1, 2 or 3 substituents selected from R$^b$;
Z is —CO$_2$H;
R¹ is biphenyl, wherein biphenyl is unsubstituted or substituted with 1, 2 or 3 substituents independently selected from R$^a$;
R² is halogen;
R³ is hydrogen or halogen;
R⁴ is hydrogen; and
R⁵ is hydrogen;
or a pharmaceutically acceptable salt thereof.

16. The compound according to claim 1, selected from:

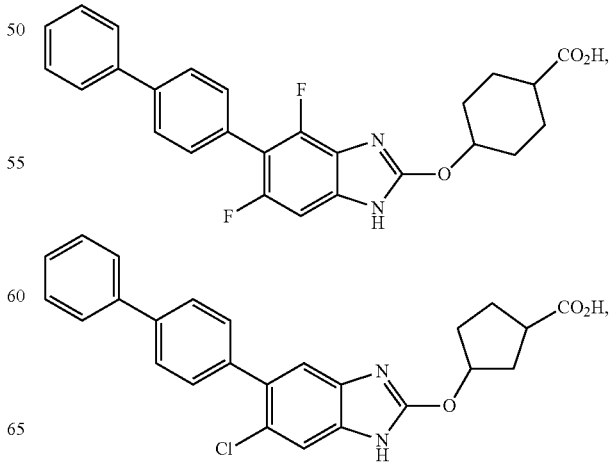

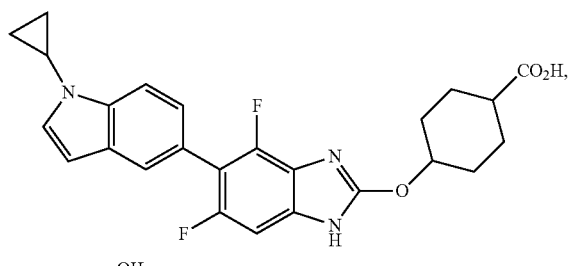
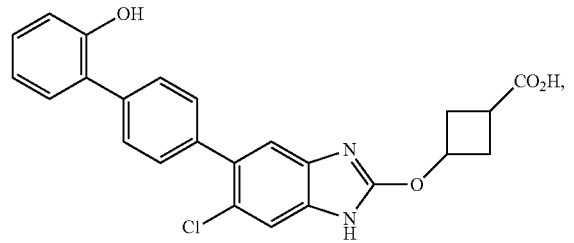
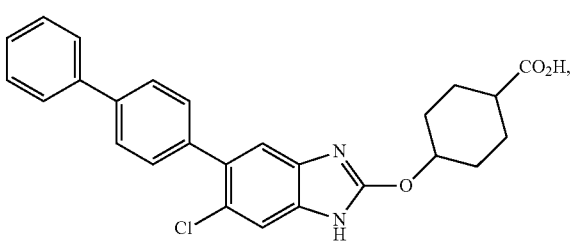 [SMILES: O=C(O)C1CCC(Oc2nc3c(F)c(-c4ccc(-c5ccccc5)cc4)c(F)cc3[nH]2)CC1]
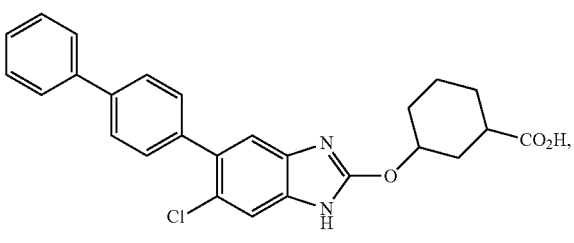
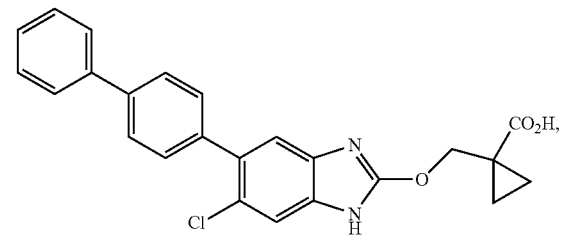
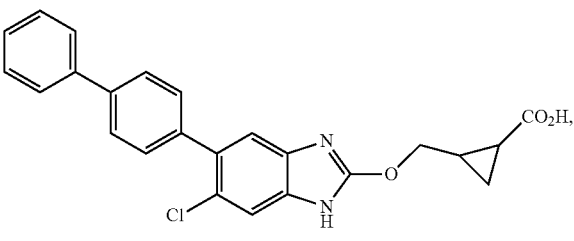
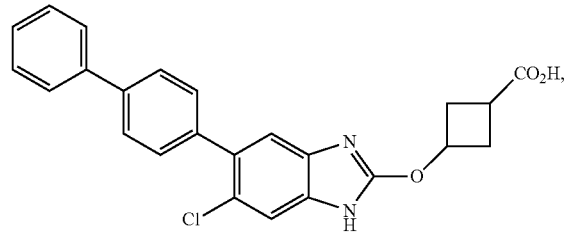
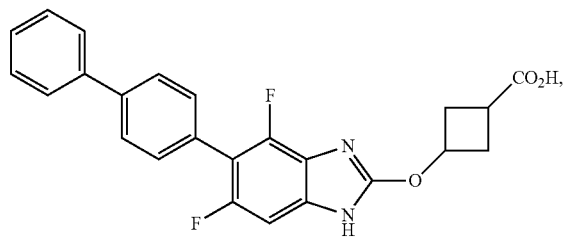
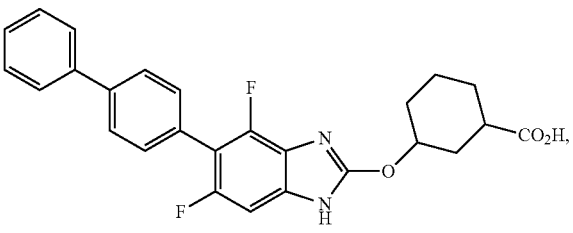
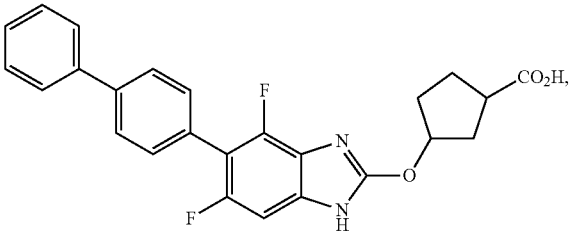
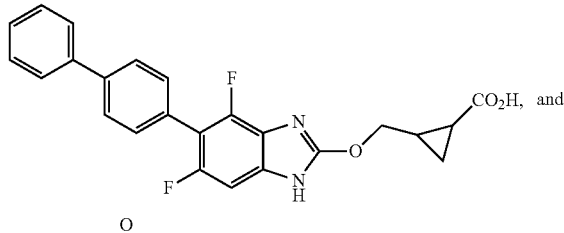
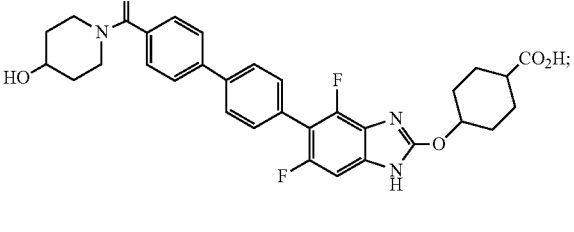
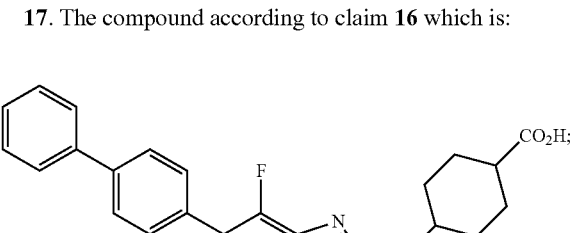
or a pharmaceutically acceptable salt thereof
17. The compound according to claim 16 which is:
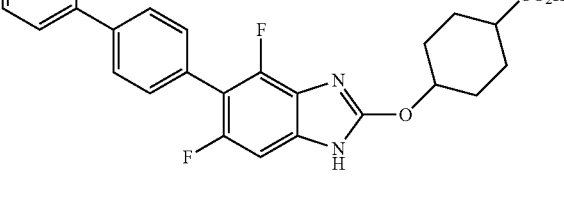
or pharmaceutically acceptable salt thereof 18. The compound according to claim 16 which is:

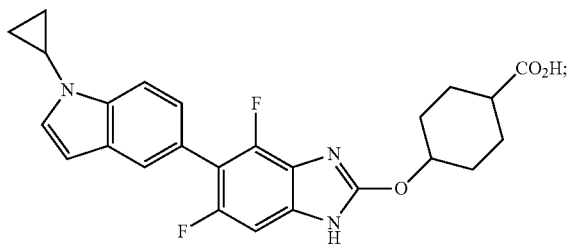 [SMILES: O=C(O)C1CCC(Oc2nc3c(F)c(-c4ccc5c(ccn5C5CC5)c4)c(F)cc3[nH]2)CC1]

or pharmaceutically acceptable salt thereof

19. The compound according to claim 16 which is:

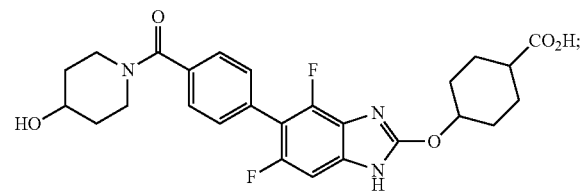 [SMILES: O=C(O)C1CCC(Oc2nc3c(F)c(-c4ccc(C(=O)N5CCC(O)CC5)cc4)c(F)cc3[nH]2)CC1]

or pharmaceutically acceptable salt thereof

20. The compound according to claim 16 which is:

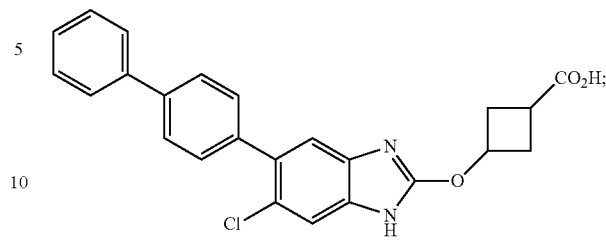

or pharmaceutically acceptable salt thereof

21. A composition comprising a compound according to claim 1 and a pharmaceutically acceptable carrier.

22. A composition comprising a compound according to claim 1 and a compound selected from simvastatin, ezetimibe, taranabant and sitagliptin; and a pharmaceutically acceptable carrier.

23. A method of treating a disorder, condition or disease responsive to the activation of AMP-activated protein kinase in a patient in need thereof comprising administration of a therapeutically effective amount of a compound according to claim 1, wherein the disorder, condition, or disease is Type 2 diabetes.

* * * * *